US012644121B2

(12) United States Patent
Khalili et al.

(10) Patent No.: US 12,644,121 B2
(45) Date of Patent: *Jun. 2, 2026

(54) HIV-1 ERADICATION STRATEGY EMPLOYING NANOFORMULATED ANTI-RETROVIRAL DRUGS AND GENE EDITING AGENTS

(71) Applicants: Temple University—of the Commonwealth System of Higher Education, Philadelphia, PA (US); Board of Regents of the University of Nebraska, Lincoln, NE (US)

(72) Inventors: Kamel Khalili, Bala Cynwyd, PA (US); Howard E. Gendelman, Omaha, NE (US); Benson Edagwa, Omaha, NE (US)

(73) Assignees: Temple University—of the Commonwealth System of Higher Education, Philadelphia, PA (US); Board of Regents of the University of Nebraska, Lincoln, NE (US)

( * ) Notice: Subject to any disclaimer, the term of this patent is extended or adjusted under 35 U.S.C. 154(b) by 329 days.

This patent is subject to a terminal disclaimer.

(21) Appl. No.: 16/605,922

(22) PCT Filed: Apr. 9, 2018

(86) PCT No.: PCT/US2018/026716
§ 371 (c)(1),
(2) Date: Oct. 17, 2019

(87) PCT Pub. No.: WO2018/194876
PCT Pub. Date: Oct. 25, 2018

(65) Prior Publication Data
US 2020/0140865 A1      May 7, 2020

Related U.S. Application Data

(60) Provisional application No. 62/524,218, filed on Jun. 23, 2017, provisional application No. 62/486,237, filed on Apr. 17, 2017.

(51) Int. Cl.
*C12N 15/113*      (2010.01)
*A61K 31/513*      (2006.01)
(Continued)

(52) U.S. Cl.
CPC ........ *C12N 15/1132* (2013.01); *A61K 31/513* (2013.01); *A61P 31/18* (2018.01);
(Continued)

(58) Field of Classification Search
CPC .. C12N 2310/20; C12N 15/111; A61K 48/00; A61P 31/12
See application file for complete search history.

(56) References Cited

U.S. PATENT DOCUMENTS

| | | | | |
|---|---|---|---|---|
| 9,925,248 B2 * | 3/2018 | Khalili | .................... | A61P 31/00 |
| 11,273,209 B2 * | 3/2022 | Khalili | .................... | C12N 9/22 |

(Continued)

FOREIGN PATENT DOCUMENTS

| | | | | |
|---|---|---|---|---|
| WO | WO-2016154016 A2 * | 9/2016 | ............. | A61K 45/06 |
| WO | 2017058658 A2 | 4/2017 | | |

OTHER PUBLICATIONS

Edagwa et al., "Long-Acting Slow Effective Release Antiretroviral Therapy," Expert Opinion on Drug Delivery, 14:11, pp. 1281-1291, 2017.
(Continued)

*Primary Examiner* — Terra C Gibbs
(74) *Attorney, Agent, or Firm* — Fox Rothschild LLP; Nicholas Zachariades

(57) ABSTRACT
Methods of eliminating a retrovirus from a subject utilize nanoformulated anti-retroviral compounds and gene editing agents. Compositions comprise at least one anti-retroviral compounds, at least one gene-editing agent, or combinations thereof.

14 Claims, 41 Drawing Sheets

Specification includes a Sequence Listing.

(51) Int. Cl.
    *A61P 31/18*      (2006.01)
    *C12N 15/10*      (2006.01)
    *A61K 45/06*      (2006.01)
    *B82Y 5/00*       (2011.01)

(52) U.S. Cl.
    CPC ............ *C12N 15/102* (2013.01); *A61K 45/06*
                     (2013.01); *B82Y 5/00* (2013.01)

(56)                    References Cited

U.S. PATENT DOCUMENTS

| | | | |
|---|---|---|---|
| 11,285,193 B2 * | 3/2022 | Khalili | ................... A61K 45/06 |
| 11,298,411 B2 * | 4/2022 | Khalili | ................... A61P 31/12 |
| 2015/0232883 A1 | 8/2015 | Dahlman et al. | |
| 2016/0017301 A1 | 1/2016 | Khalili et al. | |

OTHER PUBLICATIONS

Dash et al., "Long-Acting NanoART Elicits Potent Antiretroviral and Neuroprotective Responses in HIV-1 Infected Humanized Mice," AIDS, 26:17, pp. 2135-2144, 2012.
Nowacek et al., "Nanoformulated Antiretroviral Combinations Extend Drug Release and Antiretroviral Responses in HIV-1 Infected Macrophages: Implications for NeuroAIDS Therapeutics," J Neuroimmune Pharmacol, 5(4): 592-601, 2010.
International Search Report from corresponding International Application No. PCT/US2018/026716 dated Jul. 5, 2018, 2 pages.

* cited by examiner

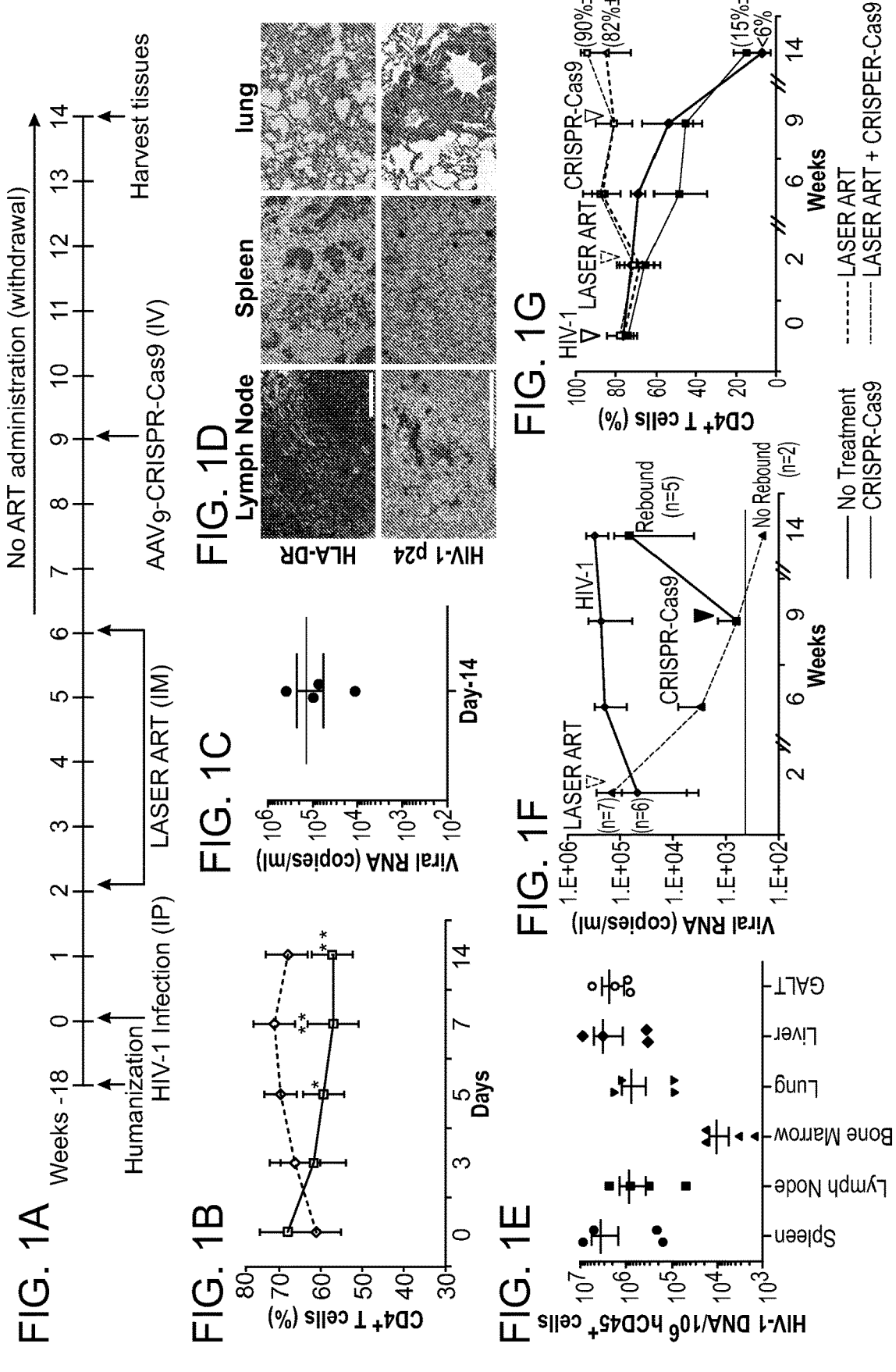

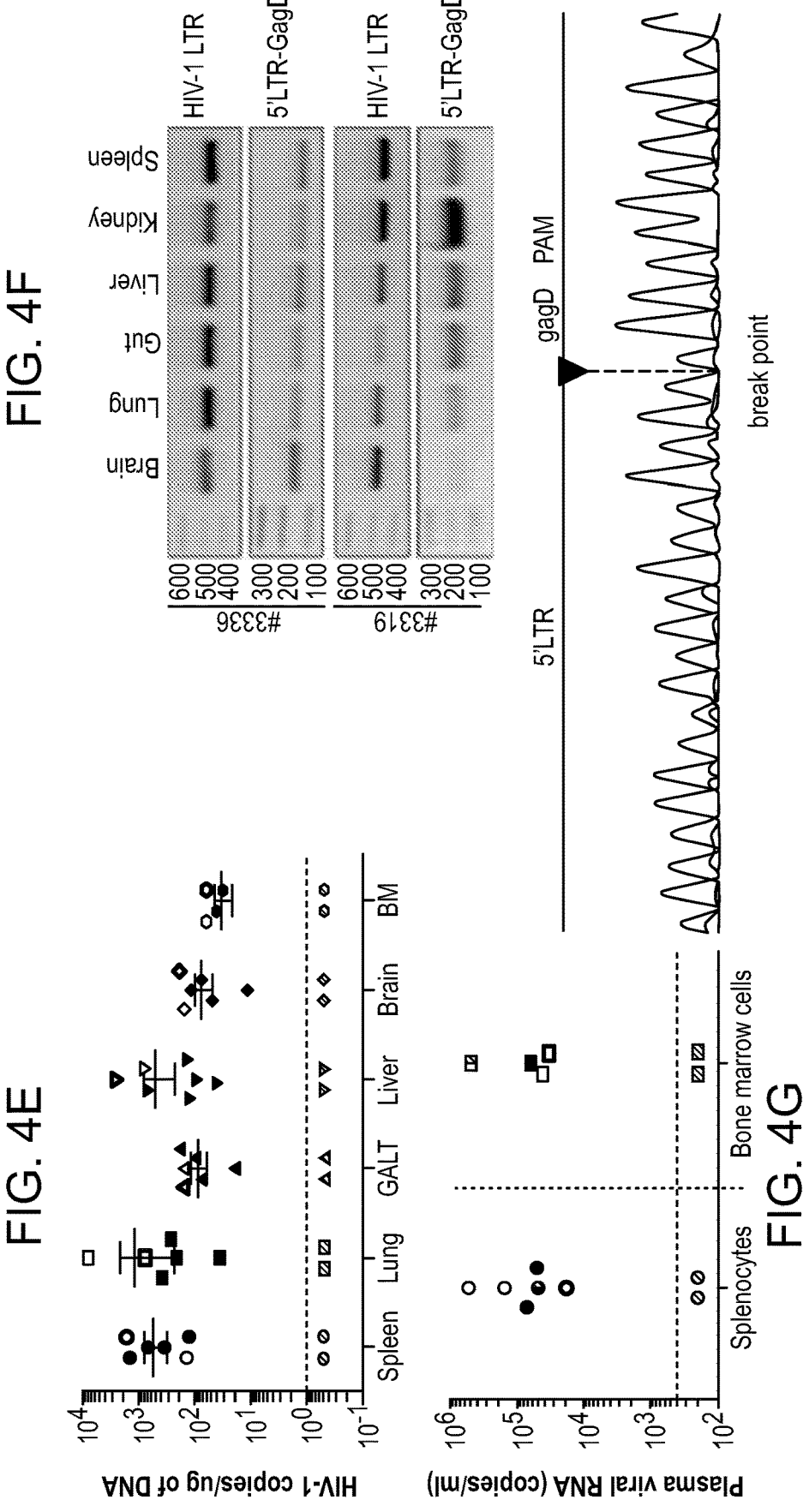

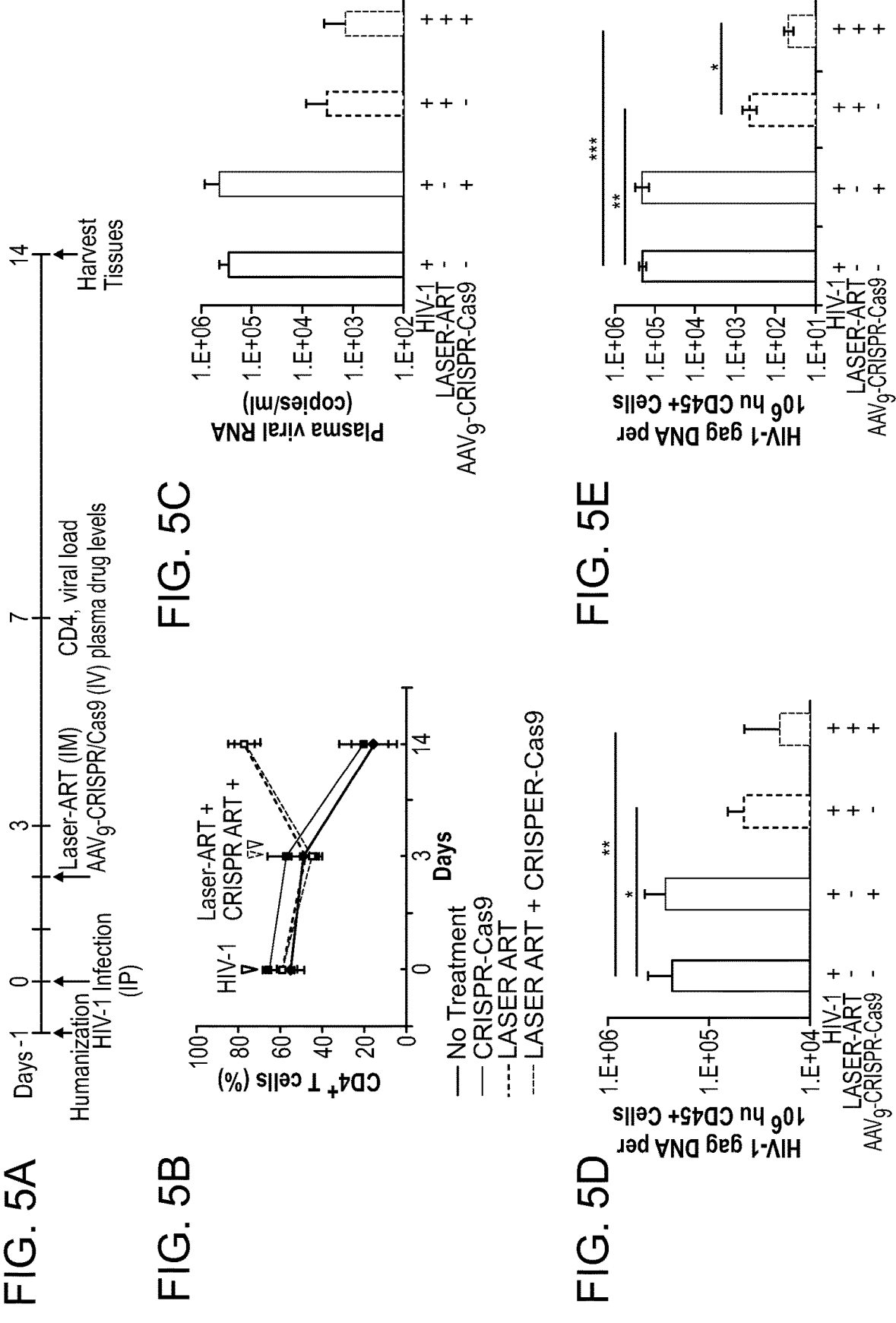

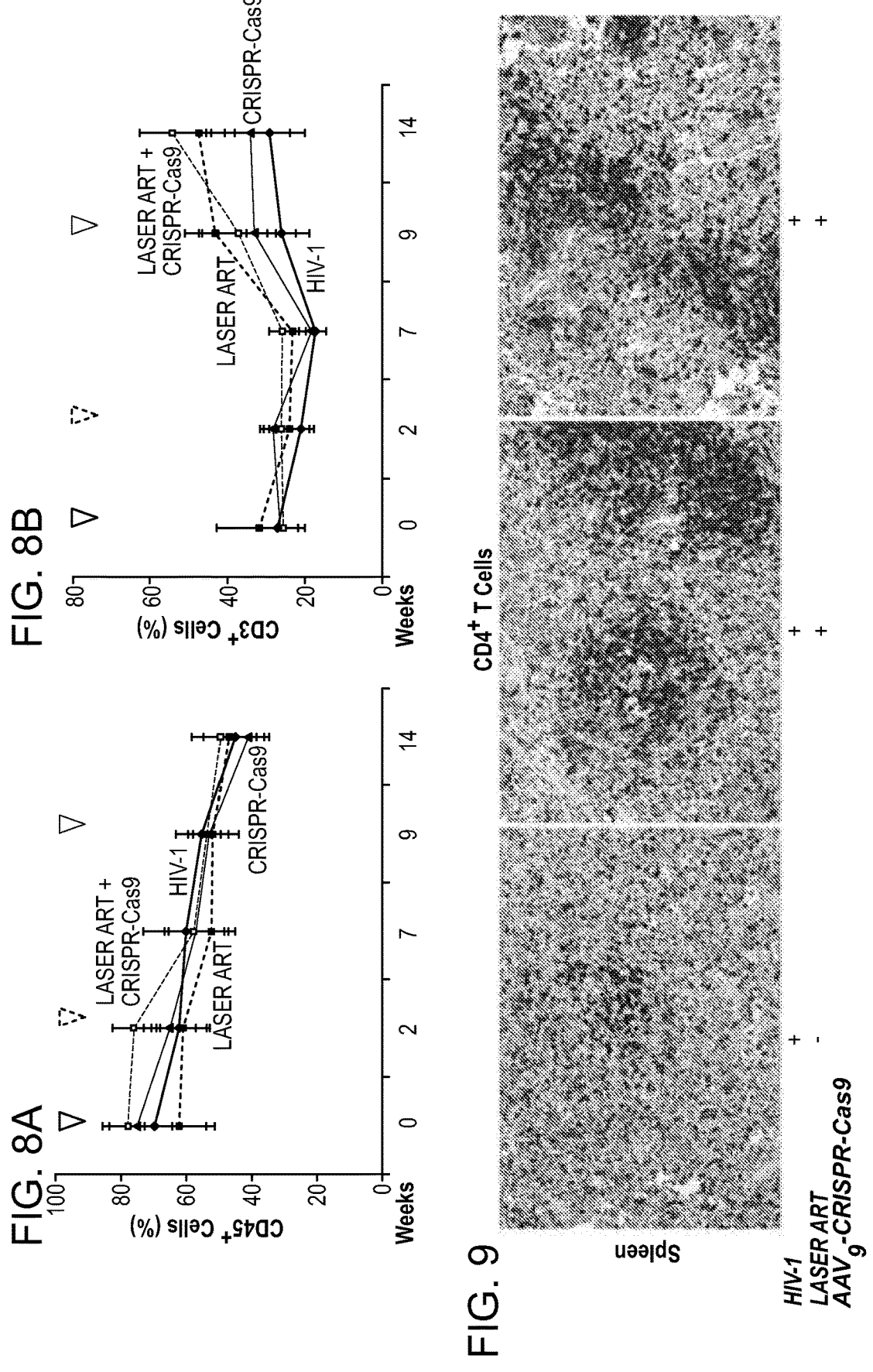

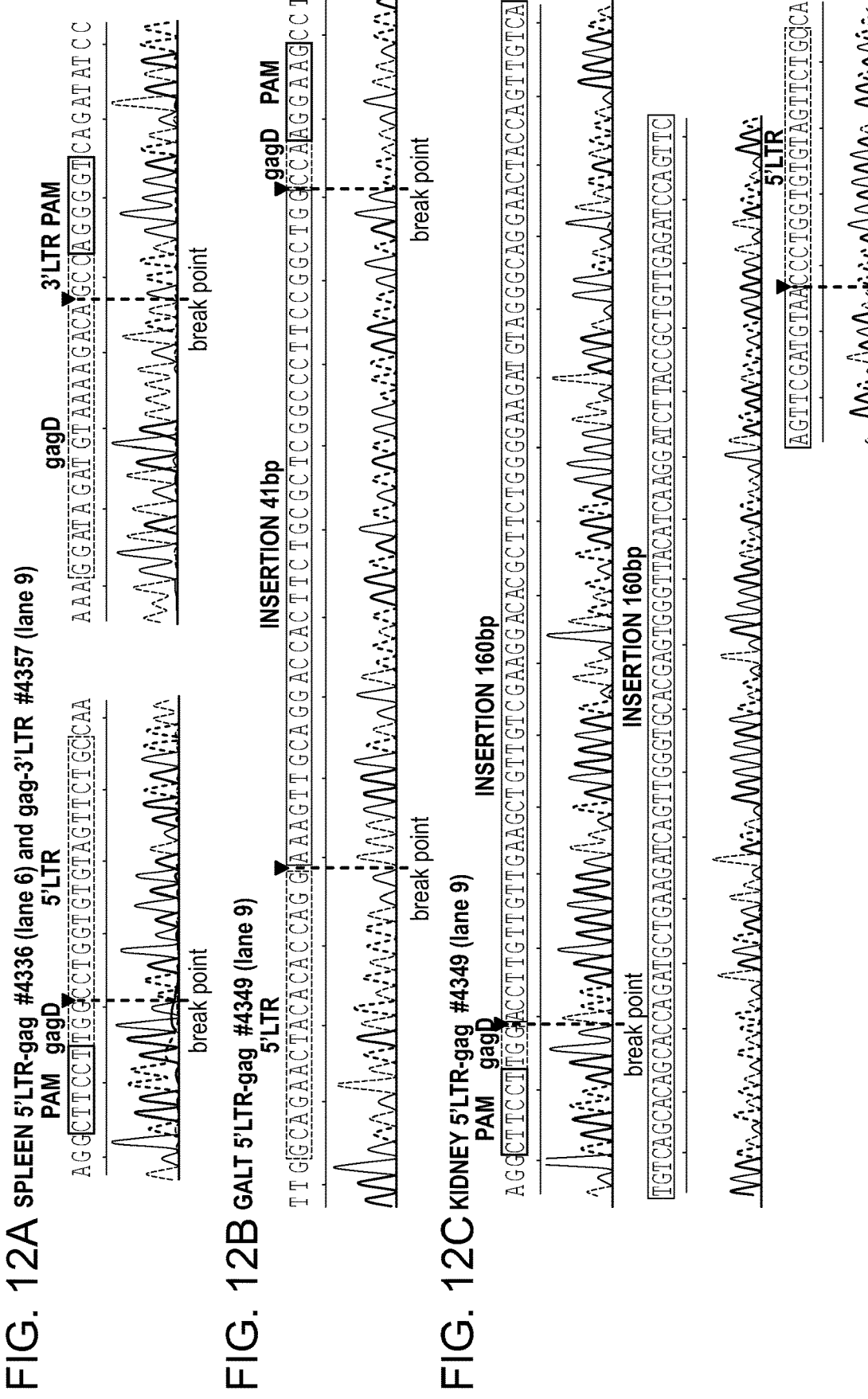
FIG. 12A SPLEEN 5'LTR-gag #4336 (lane 6) and gag-3'LTR #4357 (lane 9)
FIG. 12B GALT 5'LTR-gag #4349 (lane 9)
FIG. 12C KIDNEY 5'LTR-gag #4349 (lane 9)

GALT 5'LTR-gag #4346 (lane 6)

break point

GALT gag-3'LTR #4346 (lane 6)

break point

KIDNEY 5'LTR-gag #4350 (lane 10)

break point

KIDNEY gag-3'LTR #4348 (lane 6)

break point

LUNG 5'LTR-gag #4358 (lane 4)

break point

LUNG gag-3'LTR #4346 (lane 6)

break point

LIVER 5'LTR-gag #4357 (lane 3)

break point

LIVER gag-3'LTR- #4348 (lane 8)

break point

BRAIN 5'LTR-gag #4348 (lane 8)

break point

BRAIN gag-3'LTR- #4355 (lane 1)

break point

SPLEEN gag-3'LTR  #4356 (lane 2)

SPLEEN gag-3'LTR  #4375 (lane 12)

KIDNEY 5'LTR-gag  #4347 (lane 7)

FIG. 14A

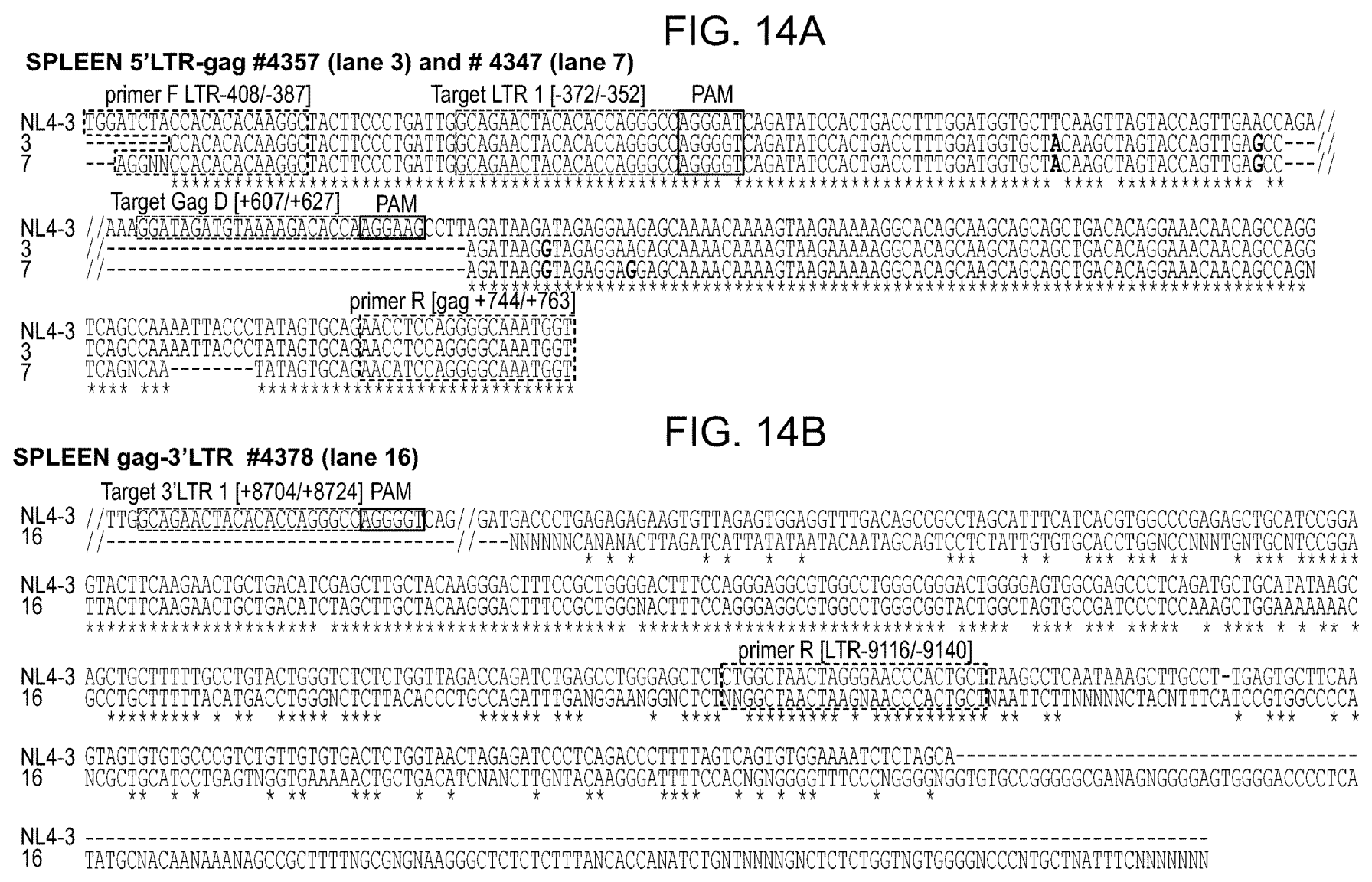

SPLEEN 5'LTR-gag #4357 (lane 3) and # 4347 (lane 7)

[Sequence alignment figure with labels: primer F LTR-408/-387], Target LTR 1 [-372/-352], PAM, Target Gag D [+607/+627], PAM, primer R [gag +744/+763], for NL4-3, 3, 7]

FIG. 14B

SPLEEN gag-3'LTR #4378 (lane 16)

[Sequence alignment figure with labels: Target 3'LTR 1 [+8704/+8724] PAM, primer R [LTR-9116/-9140], for NL4-3, 16]

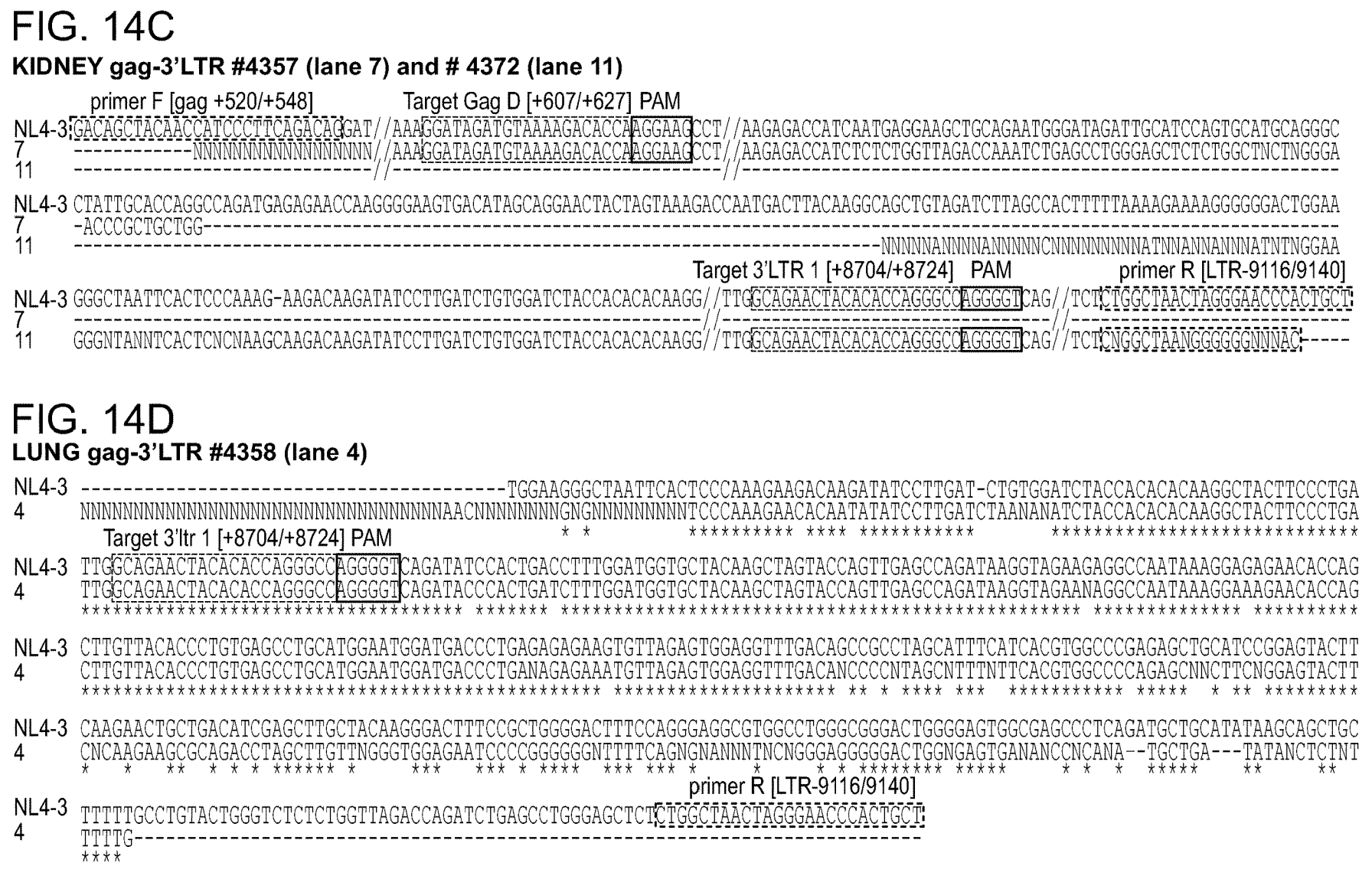

FIG. 14C
KIDNEY gag-3'LTR #4357 (lane 7) and # 4372 (lane 11)

primer F [gag +520/+548]    Target Gag D [+607/+627] PAM

NL4-3
7
11

Target 3'LTR 1 [+8704/+8724]    PAM    primer R [LTR-9116/9140]

NL4-3
7
11

FIG. 14D
LUNG gag-3'LTR #4358 (lane 4)

NL4-3
4

Target 3'ltr 1 [+8704/+8724] PAM

NL4-3
4 primer R [LTR-9116/9140]

LIVER gag-3'LTR #3536 (lane 13) and # 4378 (lane 16)

primer F [gag +520/+546]          Target Gag D [+607/+627]     PAM

```
NL4-3    GACAGCTACAACCATCCCTTCAGACACAGAT//AAAGGATAGATGTAAAAGACACCAAGGAAGCCT//TGCAAATGTTAAA//GAAAATCTATAAAA//
2        --------------------------------NNNNNN//AAAGGATANNNNTTNAAANACACCAGGAGTCCT//------------//GAAAATCTATA---//
16top    ---------------------------------NNNNN//AAAGGATAAATAGTAAAAGACACCAAGGAAGCCT//TGCAAATGTTAAA//GAAAATCTATA---//
16bottom ---------------------------------NNNNN//AAAGGATAAATGTAAAAGACACCAAGGAAGCCT//TGCAAATGTT---//-----//
                                                 *  *  ***********  *  *   ***********  *    ****   **********
```

Target 3'LTR 1 [+8704/+8724]     PAM                              primer R [LTR - 9116/-9140]

```
NL4-3    //TTGGCAGAACTACACACCAGGGCCAGGGGTCAG//GGAGTGGCGAGCC//GGAGCTCTCTGGCTAACTAGGGAACCCACTGCT
2        //------------------------------CAG//------------//GNACCTCTCTGGCTAANNANGNAACCCACTGTG
16top    //------------------------------CAG//------------//---GCTCTCTGGCTAACTAGGGAACCCACTGNG
16bottom //------------------------------CAG//-----GTGGCGAGCC//GGAGCTCTCTGGCTAACTAGGGAACCCACTGCT
                                                            *  *****************  *  *  **********
```

FIG. 14F

BRAIN gag-3'LTR #4349 (lane 9)

primer F [gag +520/+548]          Target Gag D [+607/+627]     PAM

```
NL4-3 //ACAGCTACAACCATCCCTTCAGACACAGAT//AAAGGATAGATGTAAAAGACACCAAGGAAGCCT//AGACCATCAA//AGACCATCAA//
9     //----------------NNNNNNNNNN----//AAAGGATAGNNNTNNAAGACACCAGGAAGCCT//AGACCAT----//-------//
                                             *  *********  *  ***********       ********
``` primer R [LTR-9116/-9140]

```
NL4-3 //GGTCTCTCTGGTTAGACCAGATCTGAGCCTCTGGGAGCCT   Target 3'LTR 1 [+8704/+8724]     PAM
9     //----CTCTCTGGTTAGACCAGATCTGAGCCTCTGGGAGCCT   //TTGGCAGAACTACACACCAGGGCCAGGGGT//CAG//
          ******************************************
```

Chromosome Information
Read Coverage
InDel Density
SNP Density
Proportion of HomozygousSNP
CNVInference
SVInference

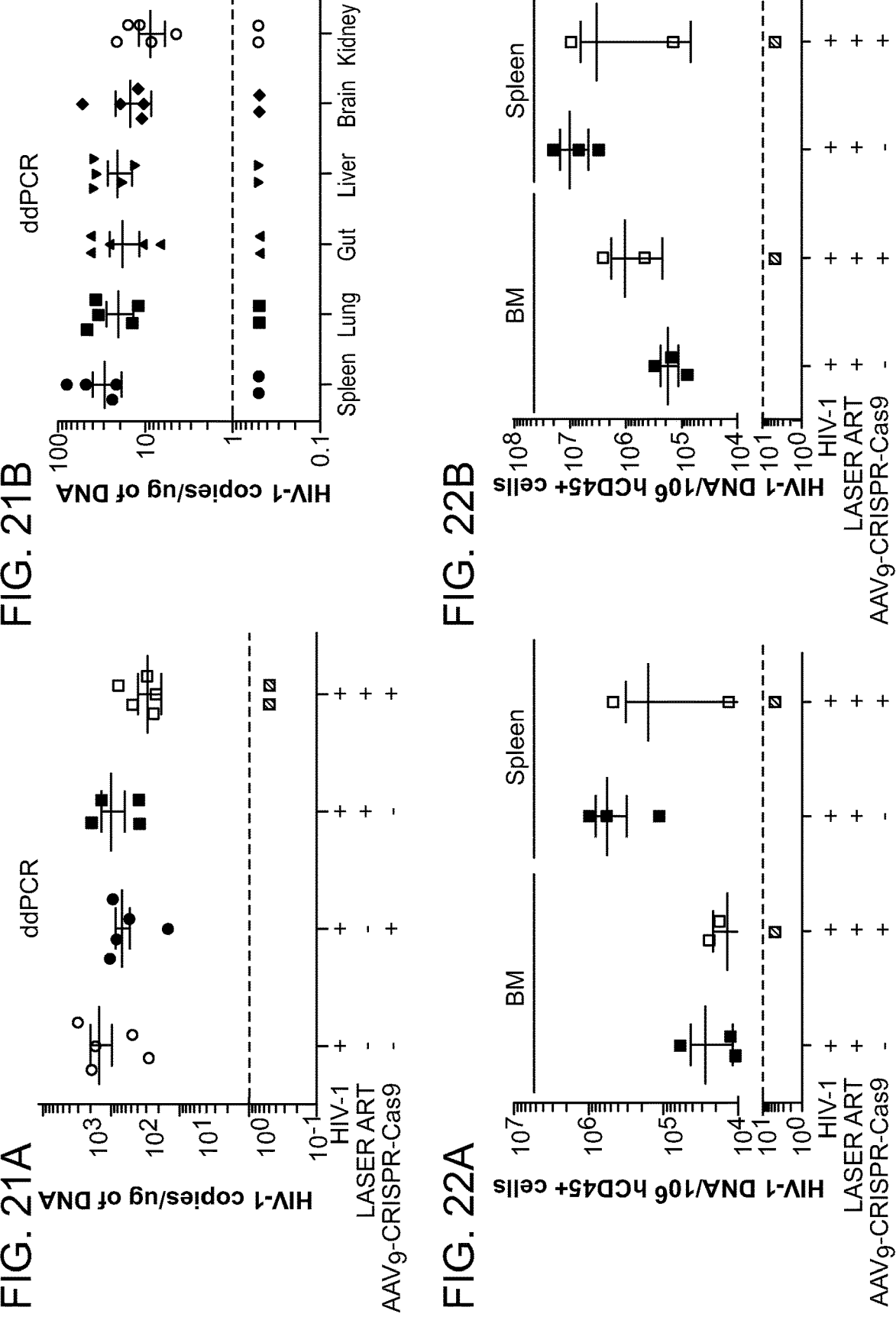

Liver

Gating Strategy

SEQUENCE LISTING

```
<160> NUMBER OF SEQ ID NOS: 310

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcagcccaga agtaataccc atgt                                              24

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cactgtgttt agcatggtgt tt                                                22

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aattgcggcc gctggaaggg ctaatttggt ccc                                    33

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtcacttcc ccttggttct ctc                                               23
```

```
<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaaagaattc gtggatctac cacacacaag gc                                     32

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaaaggatcc accatttgcc cctggaggtt                                        30

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaaagcgaaa gtaaagccag aggagat                                           27

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acacaacaga cgggcacaca ctactt                                            26

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaaagaattc gacagctaca accatccctt cagacag                                37

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaaaggatcc agcagtgggt tccctagtta gccag                                  35
```

-continued

```
<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttggcagaac tacacaccag gg                                                22

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccgagagctc ccaggctcag atct                                              24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttagcagaac tacacaccag ggcc                                              24

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gctgcttata tgtagcatct gag                                               23

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cccttggacc cagaggttct                                                   20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgagcacttt cttgccatga                                                   20

<210> SEQ ID NO 17
```

<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cccttggacc cagcggtact                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gttatcacct tcttgccatg                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tccagcagag acagggcaag                                               20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgccaaattc ctgcttgatc cc                                            22

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
cgcccaccaa caggcggcct taactg                                        26

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tccttgggat gttgatgatc t                                             21

<210> SEQ ID NO 23
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tggcccaaac attatgtacc                                                 20

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
tggtggttgc ttctttccac aca                                             23

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cccttggacc cagaggttct                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cgagcacttt cttgccatga                                                 20

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
gcgagcatct gtccactcct gatgctgtta tgggcgctcg c                         41

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcagaactac acaccagggc c                                               21

<210> SEQ ID NO 29
<211> LENGTH: 21
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 29
ggatagatgt aaaagacacc a                                          21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cgccaacaag ttgacgagat                                            20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tcgactacaa cctgctgacc                                            20

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggtgggcttc ttctgctt                                              18

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctacaatgag ctgcgtgtgg c                                          21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
caggtccaga cgcaggatgg c                                          21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gagtgacctt cccaaattgc                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atggtgaggt gagggatgag                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cagactctga tgggtggcag                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gctaaggaga gagggtggga                                              20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccaagtggcc ctcagattac a                                            21

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tcattcaccc caaatcctac gg                                           22

<210> SEQ ID NO 41
<211> LENGTH: 20
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 41
cattaaccac ctggggaaca                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tctcagaccc aggaatgtca                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gaggactctc cagccaaagg                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gagctggggg tcttagagga                                              20

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tgcaccagcc aaaacttagg a                                            21

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tctaattagg tggcagcacg tt                                           22

<210> SEQ ID NO 47
<211> LENGTH: 26
<212> TYPE: DNA
<213> ORGANISM: Homo sapiens

<400> SEQUENCE: 47

-continued

```
tctaaactcc acaccagggc catgaa                                    26

<210> SEQ ID NO 48
<211> LENGTH: 26
<212> TYPE: DNA
<213> ORGANISM: Homo sapiens

<400> SEQUENCE: 48
tcagatctcc acaccagagc cacgag                                    26

<210> SEQ ID NO 49
<211> LENGTH: 26
<212> TYPE: DNA
<213> ORGANISM: Homo sapiens

<400> SEQUENCE: 49
acaggccaac ccaccagggc ccagag                                    26

<210> SEQ ID NO 50
<211> LENGTH: 26
<212> TYPE: DNA
<213> ORGANISM: Homo sapiens

<400> SEQUENCE: 50
gtaggactac gcaccagggc aaagag                                    26

<210> SEQ ID NO 51
<211> LENGTH: 26
<212> TYPE: DNA
<213> ORGANISM: Homo sapiens

<400> SEQUENCE: 51
acaaaagtac acaccagagc ctgggg                                    26

<210> SEQ ID NO 52
<211> LENGTH: 26
<212> TYPE: DNA
<213> ORGANISM: Homo sapiens

<400> SEQUENCE: 52
tgtgaactac gccccagggc ctggaa                                    26

<210> SEQ ID NO 53
<211> LENGTH: 26
<212> TYPE: DNA
<213> ORGANISM: Homo sapiens

<400> SEQUENCE: 53
acagagctga gcaccagggc ccaggg                                    26

<210> SEQ ID NO 54
<211> LENGTH: 26
<212> TYPE: DNA
<213> ORGANISM: Homo sapiens

<400> SEQUENCE: 54
ccagttctcc accccagggc catgga                                    26

<210> SEQ ID NO 55
<211> LENGTH: 26
<212> TYPE: DNA
<213> ORGANISM: Homo sapiens
```

<400> SEQUENCE: 55
ccagagctgc ttaccagggc catgga                                              26

<210> SEQ ID NO 56
<211> LENGTH: 26
<212> TYPE: DNA
<213> ORGANISM: Homo sapiens

<400> SEQUENCE: 56
acagcactcc ccaccagggc ttgggg                                              26

<210> SEQ ID NO 57
<211> LENGTH: 26
<212> TYPE: DNA
<213> ORGANISM: Homo sapiens

<400> SEQUENCE: 57
acagaacgtc acaccagggt caggag                                              26

<210> SEQ ID NO 58
<211> LENGTH: 26
<212> TYPE: DNA
<213> ORGANISM: Homo sapiens

<400> SEQUENCE: 58
acaaaactag acagcagggc caggag                                              26

<210> SEQ ID NO 59
<211> LENGTH: 26
<212> TYPE: DNA
<213> ORGANISM: Homo sapiens

<400> SEQUENCE: 59
tgagcacttc acagcagggc cgggaa                                              26

<210> SEQ ID NO 60
<211> LENGTH: 26
<212> TYPE: DNA
<213> ORGANISM: Homo sapiens

<400> SEQUENCE: 60
gcagcactac acatcagggc taagaa                                              26

<210> SEQ ID NO 61
<211> LENGTH: 26
<212> TYPE: DNA
<213> ORGANISM: Homo sapiens

<400> SEQUENCE: 61
ccgcaactcc acagcagggc caggga                                              26

<210> SEQ ID NO 62
<211> LENGTH: 26
<212> TYPE: DNA
<213> ORGANISM: Homo sapiens

<400> SEQUENCE: 62
ctagaggaac acaccagggc ctggga                                              26

<210> SEQ ID NO 63
<211> LENGTH: 26
<212> TYPE: DNA
<213> ORGANISM: Homo sapiens

<400> SEQUENCE: 63
acagccccag acaccagggc ctggag                                      26

<210> SEQ ID NO 64
<211> LENGTH: 26
<212> TYPE: DNA
<213> ORGANISM: Homo sapiens

<400> SEQUENCE: 64
ccaggtctac ccagcagggc caggag                                      26

<210> SEQ ID NO 65
<211> LENGTH: 26
<212> TYPE: DNA
<213> ORGANISM: Homo sapiens

<400> SEQUENCE: 65
acaggagggc acaccagggc ccagga                                      26

<210> SEQ ID NO 66
<211> LENGTH: 26
<212> TYPE: DNA
<213> ORGANISM: Homo sapiens

<400> SEQUENCE: 66
acagaaataa acaccagggc ttcggg                                      26

<210> SEQ ID NO 67
<211> LENGTH: 26
<212> TYPE: DNA
<213> ORGANISM: Homo sapiens

<400> SEQUENCE: 67
gcagaactgc agaccagggg ctgggg                                      26

<210> SEQ ID NO 68
<211> LENGTH: 26
<212> TYPE: DNA
<213> ORGANISM: Homo sapiens

<400> SEQUENCE: 68
ccagagcacc aaaccagggc ccagga                                      26

<210> SEQ ID NO 69
<211> LENGTH: 26
<212> TYPE: DNA
<213> ORGANISM: Homo sapiens

<400> SEQUENCE: 69
gcagagctcc ccaccagggg caggga                                      26

<210> SEQ ID NO 70
<211> LENGTH: 26
<212> TYPE: DNA
<213> ORGANISM: Homo sapiens

<400> SEQUENCE: 70
acaggcccac actccagggc ccagaa                                      26

<210> SEQ ID NO 71
<211> LENGTH: 26
<212> TYPE: DNA

<213> ORGANISM: Homo sapiens

<400> SEQUENCE: 71
gcagtgccac actccagggc cttggg                                    26

<210> SEQ ID NO 72
<211> LENGTH: 26
<212> TYPE: DNA
<213> ORGANISM: Homo sapiens

<400> SEQUENCE: 72
gcaggagtag gcaccagggc cctgag                                    26

<210> SEQ ID NO 73
<211> LENGTH: 26
<212> TYPE: DNA
<213> ORGANISM: Homo sapiens

<400> SEQUENCE: 73
gcagcaccac acaccaggcc caggag                                    26

<210> SEQ ID NO 74
<211> LENGTH: 26
<212> TYPE: DNA
<213> ORGANISM: Homo sapiens

<400> SEQUENCE: 74
gcagagctag ccaccagggc ttagga                                    26

<210> SEQ ID NO 75
<211> LENGTH: 26
<212> TYPE: DNA
<213> ORGANISM: Homo sapiens

<400> SEQUENCE: 75
gcagagctcc agcccagggc ctgggg                                    26

<210> SEQ ID NO 76
<211> LENGTH: 26
<212> TYPE: DNA
<213> ORGANISM: Homo sapiens

<400> SEQUENCE: 76
ggggaaatac acatcagggc caggaa                                    26

<210> SEQ ID NO 77
<211> LENGTH: 26
<212> TYPE: DNA
<213> ORGANISM: Homo sapiens

<400> SEQUENCE: 77
agagaatttc acaacagggc cctgaa                                    26

<210> SEQ ID NO 78
<211> LENGTH: 26
<212> TYPE: DNA
<213> ORGANISM: Homo sapiens

<400> SEQUENCE: 78
acaaacctac agaccagagc ccaggg                                    26

<210> SEQ ID NO 79
<211> LENGTH: 26

<212> TYPE: DNA
<213> ORGANISM: Homo sapiens

<400> SEQUENCE: 79
catgagctac acaccaggac caggag                                        26

<210> SEQ ID NO 80
<211> LENGTH: 26
<212> TYPE: DNA
<213> ORGANISM: Homo sapiens

<400> SEQUENCE: 80
gaaaaactac agaccaggga caaggg                                        26

<210> SEQ ID NO 81
<211> LENGTH: 26
<212> TYPE: DNA
<213> ORGANISM: Homo sapiens

<400> SEQUENCE: 81
ccagaactca gccccagggc cctggg                                        26

<210> SEQ ID NO 82
<211> LENGTH: 26
<212> TYPE: DNA
<213> ORGANISM: Homo sapiens

<400> SEQUENCE: 82
gctggcctac acaccaggcc cagg003                                       26

<210> SEQ ID NO 83
<211> LENGTH: 26
<212> TYPE: DNA
<213> ORGANISM: Homo sapiens

<400> SEQUENCE: 83
cctgaaccac accccagggc tcaggg                                        26

<210> SEQ ID NO 84
<211> LENGTH: 26
<212> TYPE: DNA
<213> ORGANISM: Homo sapiens

<400> SEQUENCE: 84
gcagaacacc aagccagggc caggaa                                        26

<210> SEQ ID NO 85
<211> LENGTH: 26
<212> TYPE: DNA
<213> ORGANISM: Homo sapiens

<400> SEQUENCE: 85
gaatagctac acactagggc catgga                                        26

<210> SEQ ID NO 86
<211> LENGTH: 26
<212> TYPE: DNA
<213> ORGANISM: Homo sapiens

<400> SEQUENCE: 86
gaagaaccac aaaacagggc ccagaa                                        26

<210> SEQ ID NO 87

-continued

```
<211> LENGTH: 26
<212> TYPE: DNA
<213> ORGANISM: Homo sapiens

<400> SEQUENCE: 87
atagtactac actcctgggc ctcgag                                          26

<210> SEQ ID NO 88
<211> LENGTH: 26
<212> TYPE: DNA
<213> ORGANISM: Homo sapiens

<400> SEQUENCE: 88
gaagaacaac acagcagggc agagag                                          26

<210> SEQ ID NO 89
<211> LENGTH: 26
<212> TYPE: DNA
<213> ORGANISM: Homo sapiens

<400> SEQUENCE: 89
ccagaaacac ccaccagtgc ccggga                                          26

<210> SEQ ID NO 90
<211> LENGTH: 26
<212> TYPE: DNA
<213> ORGANISM: Homo sapiens

<400> SEQUENCE: 90
ccagagctgc agacccgggc cccggg                                          26

<210> SEQ ID NO 91
<211> LENGTH: 26
<212> TYPE: DNA
<213> ORGANISM: Homo sapiens

<400> SEQUENCE: 91
ccagaccgag acaccagggg cggggg                                          26

<210> SEQ ID NO 92
<211> LENGTH: 26
<212> TYPE: DNA
<213> ORGANISM: Homo sapiens

<400> SEQUENCE: 92
ccagatctag actccagggc agtgag                                          26

<210> SEQ ID NO 93
<211> LENGTH: 26
<212> TYPE: DNA
<213> ORGANISM: Homo sapiens

<400> SEQUENCE: 93
tcagagctag actccagggc tggggg                                          26

<210> SEQ ID NO 94
<211> LENGTH: 26
<212> TYPE: DNA
<213> ORGANISM: Homo sapiens

<400> SEQUENCE: 94
ggagaactta acaccaggtc cctggg                                          26
```

<210> SEQ ID NO 95
<211> LENGTH: 26
<212> TYPE: DNA
<213> ORGANISM: Homo sapiens

<400> SEQUENCE: 95
ccagcaccac agagcagggc ctggga                                    26

<210> SEQ ID NO 96
<211> LENGTH: 26
<212> TYPE: DNA
<213> ORGANISM: Homo sapiens

<400> SEQUENCE: 96
ccagcaccac agagcagggc ctggga                                    26

<210> SEQ ID NO 97
<211> LENGTH: 26
<212> TYPE: DNA
<213> ORGANISM: Homo sapiens

<400> SEQUENCE: 97
agaaaaatgt aaaagacacc ttggaa                                    26

<210> SEQ ID NO 98
<211> LENGTH: 26
<212> TYPE: DNA
<213> ORGANISM: Homo sapiens

<400> SEQUENCE: 98
ttatacattt gaaagacacc aaagaa                                    26

<210> SEQ ID NO 99
<211> LENGTH: 26
<212> TYPE: DNA
<213> ORGANISM: Homo sapiens

<400> SEQUENCE: 99
ggataaatgg gaaagacacc agggga                                    26

<210> SEQ ID NO 100
<211> LENGTH: 26
<212> TYPE: DNA
<213> ORGANISM: Homo sapiens

<400> SEQUENCE: 100
tcttagactt aaaagacacc attgaa                                    26

<210> SEQ ID NO 101
<211> LENGTH: 26
<212> TYPE: DNA
<213> ORGANISM: Homo sapiens

<400> SEQUENCE: 101
acattgaatt aaaagacacc atagag                                    26

<210> SEQ ID NO 102
<211> LENGTH: 26
<212> TYPE: DNA
<213> ORGANISM: Homo sapiens

<400> SEQUENCE: 102
ggatagagcc aaaagacacc aaagag                                    26

```
<210> SEQ ID NO 103
<211> LENGTH: 26
<212> TYPE: DNA
<213> ORGANISM: Homo sapiens

<400> SEQUENCE: 103
aaatagctct taaagacacc agcgaa                                        26

<210> SEQ ID NO 104
<211> LENGTH: 26
<212> TYPE: DNA
<213> ORGANISM: Homo sapiens

<400> SEQUENCE: 104
agatcaatgt aaaagtcacc atcgaa                                        26

<210> SEQ ID NO 105
<211> LENGTH: 26
<212> TYPE: DNA
<213> ORGANISM: Homo sapiens

<400> SEQUENCE: 105
ttttagatgt aaaagacatc agggag                                        26

<210> SEQ ID NO 106
<211> LENGTH: 26
<212> TYPE: DNA
<213> ORGANISM: Homo sapiens

<400> SEQUENCE: 106
tgataaatga aacagacacc agagga                                        26

<210> SEQ ID NO 107
<211> LENGTH: 26
<212> TYPE: DNA
<213> ORGANISM: Homo sapiens

<400> SEQUENCE: 107
gaaaagattt aagagacacc aaagag                                        26

<210> SEQ ID NO 108
<211> LENGTH: 26
<212> TYPE: DNA
<213> ORGANISM: Homo sapiens

<400> SEQUENCE: 108
agggagatct aagagacacc agagag                                        26

<210> SEQ ID NO 109
<211> LENGTH: 26
<212> TYPE: DNA
<213> ORGANISM: Homo sapiens

<400> SEQUENCE: 109
atgcagatgt aacagacacc agggaa                                        26

<210> SEQ ID NO 110
<211> LENGTH: 26
<212> TYPE: DNA
<213> ORGANISM: Homo sapiens

<400> SEQUENCE: 110
gtatggatgt taaagactcc attgag                                        26
```

-continued

<210> SEQ ID NO 111
<211> LENGTH: 26
<212> TYPE: DNA
<213> ORGANISM: Homo sapiens

<400> SEQUENCE: 111
cggtagattt taaagactcc aaagag                                                 26

<210> SEQ ID NO 112
<211> LENGTH: 26
<212> TYPE: DNA
<213> ORGANISM: Homo sapiens

<400> SEQUENCE: 112
agagagatat taaagacccc agtgaa                                                 26

<210> SEQ ID NO 113
<211> LENGTH: 26
<212> TYPE: DNA
<213> ORGANISM: Homo sapiens

<400> SEQUENCE: 113
ggataaatgt gaaagacatc atagaa                                                 26

<210> SEQ ID NO 114
<211> LENGTH: 26
<212> TYPE: DNA
<213> ORGANISM: Homo sapiens

<400> SEQUENCE: 114
agaaggagga aaaagacacc agggag                                                 26

<210> SEQ ID NO 115
<211> LENGTH: 26
<212> TYPE: DNA
<213> ORGANISM: Homo sapiens

<400> SEQUENCE: 115
taataggtag aaaagacacc agtgaa                                                 26

<210> SEQ ID NO 116
<211> LENGTH: 26
<212> TYPE: DNA
<213> ORGANISM: Homo sapiens

<400> SEQUENCE: 116
ccaaagatga aaaagacacc cgagaa                                                 26

<210> SEQ ID NO 117
<211> LENGTH: 26
<212> TYPE: DNA
<213> ORGANISM: Homo sapiens

<400> SEQUENCE: 117
ttataaatgc aaaagacacc catgaa                                                 26

<210> SEQ ID NO 118
<211> LENGTH: 26
<212> TYPE: DNA
<213> ORGANISM: Homo sapiens

<400> SEQUENCE: 118
ggctgggtga aaaagacacc atggaa                                    26

<210> SEQ ID NO 119
<211> LENGTH: 26
<212> TYPE: DNA
<213> ORGANISM: Homo sapiens

<400> SEQUENCE: 119
ggacagatgt gaaagagacc aaagga                                    26

<210> SEQ ID NO 120
<211> LENGTH: 26
<212> TYPE: DNA
<213> ORGANISM: Homo sapiens

<400> SEQUENCE: 120
tgatgcaagt aacagacacc atggga                                    26

<210> SEQ ID NO 121
<211> LENGTH: 26
<212> TYPE: DNA
<213> ORGANISM: Homo sapiens

<400> SEQUENCE: 121
caatagttgt tcaagacacc agtgaa                                    26

<210> SEQ ID NO 122
<211> LENGTH: 26
<212> TYPE: DNA
<213> ORGANISM: Homo sapiens

<400> SEQUENCE: 122
agaaagatac agaagacacc agggag                                    26

<210> SEQ ID NO 123
<211> LENGTH: 26
<212> TYPE: DNA
<213> ORGANISM: Homo sapiens

<400> SEQUENCE: 123
tgagacttgt acaagacacc acgggg                                    26

<210> SEQ ID NO 124
<211> LENGTH: 26
<212> TYPE: DNA
<213> ORGANISM: Homo sapiens

<400> SEQUENCE: 124
agattgttgg taaagacacc acagag                                    26

<210> SEQ ID NO 125
<211> LENGTH: 26
<212> TYPE: DNA
<213> ORGANISM: Homo sapiens

<400> SEQUENCE: 125
ggaaagttat aaaagacacc ggggaa                                    26

<210> SEQ ID NO 126
<211> LENGTH: 26
<212> TYPE: DNA
<213> ORGANISM: Homo sapiens

<400> SEQUENCE: 126

-continued

```
ccattgatct aaaagtcacc actgga                                      26

<210> SEQ ID NO 127
<211> LENGTH: 26
<212> TYPE: DNA
<213> ORGANISM: Homo sapiens

<400> SEQUENCE: 127
aaatacctgt aagagacacc actgag                                      26

<210> SEQ ID NO 128
<211> LENGTH: 26
<212> TYPE: DNA
<213> ORGANISM: Homo sapiens

<400> SEQUENCE: 128
tggtagattt ataagacacc gtaggg                                      26

<210> SEQ ID NO 129
<211> LENGTH: 26
<212> TYPE: DNA
<213> ORGANISM: Homo sapiens

<400> SEQUENCE: 129
gaatggatgt gaaaggcacc actgaa                                      26

<210> SEQ ID NO 130
<211> LENGTH: 26
<212> TYPE: DNA
<213> ORGANISM: Homo sapiens

<400> SEQUENCE: 130
aaataaatgt gaaagtcacc acagaa                                      26

<210> SEQ ID NO 131
<211> LENGTH: 26
<212> TYPE: DNA
<213> ORGANISM: Homo sapiens

<400> SEQUENCE: 131
agatggatgg catagacacc acgggg                                      26

<210> SEQ ID NO 132
<211> LENGTH: 26
<212> TYPE: DNA
<213> ORGANISM: Homo sapiens

<400> SEQUENCE: 132
tgaaagatct taaagccacc aaagga                                      26

<210> SEQ ID NO 133
<211> LENGTH: 26
<212> TYPE: DNA
<213> ORGANISM: Homo sapiens

<400> SEQUENCE: 133
gagtagatct aaaagacagc aaggaa                                      26

<210> SEQ ID NO 134
<211> LENGTH: 26
<212> TYPE: DNA
<213> ORGANISM: Homo sapiens
```

<400> SEQUENCE: 134
tcatatgtgt aaaagacaca aaggag                                        26

<210> SEQ ID NO 135
<211> LENGTH: 26
<212> TYPE: DNA
<213> ORGANISM: Homo sapiens

<400> SEQUENCE: 135
ggttagcggg aaaagacacc acaggg                                        26

<210> SEQ ID NO 136
<211> LENGTH: 26
<212> TYPE: DNA
<213> ORGANISM: Homo sapiens

<400> SEQUENCE: 136
ggttagcggg aaaagacacc acaggg                                        26

<210> SEQ ID NO 137
<211> LENGTH: 26
<212> TYPE: DNA
<213> ORGANISM: Homo sapiens

<400> SEQUENCE: 137
ggttagcggg aaaagacacc acaggg                                        26

<210> SEQ ID NO 138
<211> LENGTH: 26
<212> TYPE: DNA
<213> ORGANISM: Homo sapiens

<400> SEQUENCE: 138
ggttagcggg aaaagacacc acaggg                                        26

<210> SEQ ID NO 139
<211> LENGTH: 26
<212> TYPE: DNA
<213> ORGANISM: Homo sapiens

<400> SEQUENCE: 139
ggttagcggg aaaagacacc acaggg                                        26

<210> SEQ ID NO 140
<211> LENGTH: 26
<212> TYPE: DNA
<213> ORGANISM: Homo sapiens

<400> SEQUENCE: 140
ggattcatgc aaaagacact ataggg                                        26

<210> SEQ ID NO 141
<211> LENGTH: 26
<212> TYPE: DNA
<213> ORGANISM: Homo sapiens

<400> SEQUENCE: 141
agaaatatct aaaagacaac aaagag                                        26

<210> SEQ ID NO 142
<211> LENGTH: 26
<212> TYPE: DNA
<213> ORGANISM: Homo sapiens

```
<400> SEQUENCE: 142
ggaaaggagc aaaagacacc agaggg                                           26

<210> SEQ ID NO 143
<211> LENGTH: 26
<212> TYPE: DNA
<213> ORGANISM: Homo sapiens

<400> SEQUENCE: 143
agattcattt aaaagacaac aaagaa                                           26

<210> SEQ ID NO 144
<211> LENGTH: 26
<212> TYPE: DNA
<213> ORGANISM: Homo sapiens

<400> SEQUENCE: 144
agagatatgt ataagacaca atagga                                           26

<210> SEQ ID NO 145
<211> LENGTH: 26
<212> TYPE: DNA
<213> ORGANISM: Homo sapiens

<400> SEQUENCE: 145
agatagaaat gaaagacact agtgaa                                           26

<210> SEQ ID NO 146
<211> LENGTH: 26
<212> TYPE: DNA
<213> ORGANISM: Homo sapiens

<400> SEQUENCE: 146
tgataaatgg gaatgacacc agagag                                           26

<210> SEQ ID NO 147
<211> LENGTH: 27
<212> TYPE: DNA
<213> ORGANISM: Human immunodeficiency virus 1

<400> SEQUENCE: 147
gcagaactac acaccagggc cagggat                                          27

<210> SEQ ID NO 148
<211> LENGTH: 27
<212> TYPE: DNA
<213> ORGANISM: Homo sapiens

<400> SEQUENCE: 148
acagcactcc ccaccagggc ttggggg                                          27

<210> SEQ ID NO 149
<211> LENGTH: 27
<212> TYPE: DNA
<213> ORGANISM: Homo sapiens

<400> SEQUENCE: 149
acaaacctac agaccagagc ccagggt                                          27

<210> SEQ ID NO 150
<211> LENGTH: 27
<212> TYPE: DNA
```

```
<213> ORGANISM: Homo sapiens

<400> SEQUENCE: 150
ccagaccgag acaccagggg cggggga                                              27

<210> SEQ ID NO 151
<211> LENGTH: 27
<212> TYPE: DNA
<213> ORGANISM: Human immunodeficiency virus 1

<400> SEQUENCE: 151
ggatagatgt aaaagacacc aaggaag                                             27

<210> SEQ ID NO 152
<211> LENGTH: 27
<212> TYPE: DNA
<213> ORGANISM: Homo sapiens

<400> SEQUENCE: 152
ccaaagatga aaaagacacc cgagaaa                                             27

<210> SEQ ID NO 153
<211> LENGTH: 27
<212> TYPE: DNA
<213> ORGANISM: Homo sapiens

<400> SEQUENCE: 153
tgagacttgt acaagacacc acggggc                                             27

<210> SEQ ID NO 154
<211> LENGTH: 27
<212> TYPE: DNA
<213> ORGANISM: Homo sapiens

<400> SEQUENCE: 154
agaaaaatgt aaaagacacc ttggaaa                                             27

<210> SEQ ID NO 155
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gcagactaca caccaggcca aggaagcct                                           29

<210> SEQ ID NO 156
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
aaaggataga tgtaaaagac agccaggggt c                                        31

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 157
ggcagaacta cacaccaggg ccaggggtca                                          30

<210> SEQ ID NO 158
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ttggcagaac tacacaccag ggccagggat cag                                      33

<210> SEQ ID NO 159
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
aaaggataga tgtaaaagac accaaggaag cct                                      33

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
tcggcagaac tacacaccag g                                                   21

<210> SEQ ID NO 161
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ccaaggaagc ct                                                             12

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ttggcagaac tacacaccag g                                                   21

<210> SEQ ID NO 163
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 163
aaaggataga tgtaaaagac accaaggaag cct                                    33

<210> SEQ ID NO 164
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ttggcagaac tacacaccag ggccaggggt cagatatcc                              39

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
aaaggataga tgtaaaagac a                                                 21

<210> SEQ ID NO 166
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
gccaggggtc agatatcc                                                     18

<210> SEQ ID NO 167
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gccagggatc agatatcc                                                     18

<210> SEQ ID NO 168
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
aaaggataga tgtaaaagac ac                                                22

<210> SEQ ID NO 169
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 169
ttggcagaac tacacaccag ggccagggat cag                                          33

<210> SEQ ID NO 170
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
aaaggataga tgtaaaagac accaaggaag cct                                          33

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ttggcagaac tacacaccag g                                                       21

<210> SEQ ID NO 172
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ccaaggaagc ct                                                                 12

<210> SEQ ID NO 173
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
aaagtagcag gaccacttct gcgctcggcc cttccggctg gccaaggaag cct                    53

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ttggcagaac tccgcaccag g                                                       21

<210> SEQ ID NO 175
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175

```
aaaggataga tgtaaaagac accaaggaag cct                                   33

<210> SEQ ID NO 176
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ttggcagaac tacacaccag ggccaggggt cagatatcc                             39

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
aaaggataga tgtaaaagac a                                                21

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gccaggggtc agatatcc                                                    18

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a, c, t, g, unknown or other

<400> SEQUENCE: 179
aaaggataga tgnaaaagac a                                                21

<210> SEQ ID NO 180
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
ttggcagaac tacacaccag ggccagggat cag                                   33

<210> SEQ ID NO 181
<211> LENGTH: 33
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 181
aaaggataga tgtaaaagac accaaggaag cct                                    33

<210> SEQ ID NO 182
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ttggcagaac tacaca                                                       16

<210> SEQ ID NO 183
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ccaaggaagc ct                                                           12

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ttggcagaac tacacaccag g                                                 21

<210> SEQ ID NO 185
<211> LENGTH: 172
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
gttacatcga actggatctc aacagcggta agatccttga tgtaacccac tcgtgcaccc        60
aactgatctt cagcatctgg tgctgtgctg acaactggta gttcctgccc tacatcttcc       120
ccagaagcgt gtccttcgac aacagcttca acaacaaggt ccaaggaagc ct              172

<210> SEQ ID NO 186
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
aaaggataga tgtaaaagac accaaggaag cct                                    33

<210> SEQ ID NO 187
<211> LENGTH: 39
<212> TYPE: DNA

-continued

<213> ORGANISM: Artificial Sequence
<220> FEATURE:
<223> OTHER INFORMATION: Description of Artificial Sequence: Synthetic
      oligonucleotide

<400> SEQUENCE: 187
ttggcagaac tacacaccag ggccaggggt cagatatcc                    39

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
aaaggataga tgtaaaagac a                                        21

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 189
gccaggggtc anatatcc                                            18

<210> SEQ ID NO 190
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gccagggatc agatatcc                                            18

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
aaaggataga tgtaaaaaac a                                        21

<210> SEQ ID NO 192
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ggcagaacta cacaccaggc caaggaagcc t                             31

```
<210> SEQ ID NO 193
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ttggcagaac tacacaccag ggccagggat cagatatcca ctgacctttg gatg            54

<210> SEQ ID NO 194
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
catccggagt actacaaaga ctgctgaca                                        29

<210> SEQ ID NO 195
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gccctcagat gctacatata agcagc                                           26

<210> SEQ ID NO 196
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ttagcagaac tacacaccag ggccaggggt cagatatcca ctgac                      45

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
tacttcaaga actgctgaca                                                  20

<210> SEQ ID NO 198
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ggggtcagat atccactgac tacttcaaga actgctgaca                            40

<210> SEQ ID NO 199
```

-continued

```
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
ttagcagaac tacacaccag ggccagggat cagatatcca ctgacctttg gatg          54

<210> SEQ ID NO 200
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
catccggagt acttcaagaa ctgctgaca                                      29

<210> SEQ ID NO 201
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
gccctcagat cctgcatata agcagc                                         26

<210> SEQ ID NO 202
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
ttagcagaac tacacaccag ggccagggat cagatatcca ctgac                    45

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
tacttcaaga actgctgaca                                                20

<210> SEQ ID NO 204
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
gccctcagat gctacatata agcagc                                         26

<210> SEQ ID NO 205
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ttagcagaac tacacaccag ggccagggat cagatatcca                               40

<210> SEQ ID NO 206
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
gggatcagat atccactgac tacttcaaga actgctgaca                               40

<210> SEQ ID NO 207
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
gggatcagat atcca                                                         15

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
tacttcaaga actgctgaca                                                    20

<210> SEQ ID NO 209
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
aggcttcctt ggcctggtgt gtagttctgc caa                                     33

<210> SEQ ID NO 210
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
aaaggataga tgtaaaagac agccaggggt cagatatcc                               39

<210> SEQ ID NO 211
<211> LENGTH: 74
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 211
ttggcagaac tacacaccag gaaagttgca ggaccacttc tgcgctcggc ccttccggct        60
ggccaaggaa gcct                                                          74

<210> SEQ ID NO 212
<211> LENGTH: 202
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212
aggcttcctt ggaccttgtt gttgaagctg ttgtcgaagg acacgcttct ggggaagatg        60
tagggcagga actaccagtt gtcatgtcag cacagcacca gatgctgaag atcagttggg       120
tgcacgagtg ggttacatca aggatcttac cgctgttgag atccagttca gttcgatgta       180
accctggtgt gtagttctgc ca                                                202

<210> SEQ ID NO 213
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
aggcttcctt ggcctggtgt gtagttctgc caa                                     33

<210> SEQ ID NO 214
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
aaaggataga tgtaaaagac agccaggggt cag                                     33

<210> SEQ ID NO 215
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
aggcttcctt ggcctggtgt gtagttctgc caa                                     33

<210> SEQ ID NO 216
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base -continued

```
<222> LOCATION: (33)..(33)
<223> OTHER INFORMATION: a, c, t, g, unknown or other

<400> SEQUENCE: 216
aaaggataga tgtaaaagac agccaggggt can                                 33

<210> SEQ ID NO 217
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
aggcttcctt ggcctggtgt gtagttctgc caa                                 33

<210> SEQ ID NO 218
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
aaaggataga tgtaaaagac agccagggat cag                                 33

<210> SEQ ID NO 219
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
aggcttcctt ggcctggtgt gtagttctgc caa                                 33

<210> SEQ ID NO 220
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
aaaggataga tgtaaaagac agccaggggt cag                                 33

<210> SEQ ID NO 221
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
aggcttcctt ggcctggtgt gtagttctgc caa                                 33

<210> SEQ ID NO 222
<211> LENGTH: 33
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 222
aaaggataga tgtaaaagac agccaggggt cag                                       33

<210> SEQ ID NO 223
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
aaaggataga tgtaaaagac aatatcc                                             27

<210> SEQ ID NO 224
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
aaaggataga tgtaaaagac acaaggag                                            28

<210> SEQ ID NO 225
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
aggcttcctt ggtgtgtagt tctgccaa                                            28

<210> SEQ ID NO 226
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226
tggatctacc acacacaagg ctacttccct gattggcaga actacacacc agggccaggg       60
atcagatatc cactgacctt tggatggtgc ttcaagttag taccagttga accaga          116

<210> SEQ ID NO 227
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 227
ccacacacaa ggctacttcc ctgattggca gaactacaca ccagggccag gggtcagata       60
tccactgacc tttggatggt gctacaagct agtaccagtt gagcc                      105

<210> SEQ ID NO 228
<211> LENGTH: 110
<212> TYPE: DNA

```
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(5)
<223> OTHER INFORMATION: a, c, t, g, unknown or other

<400> SEQUENCE: 228
aggnnccaca cacaaggcta cttccctgat tggcagaact acacaccagg gccaggggtc      60
agatatccac tgacctttgg atggtgctac aagctagtac cagttgagcc                110

<210> SEQ ID NO 229
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 229
aaaggataga tgtaaaagac accaaggaag ccttagataa gatagaggaa gagcaaaaca      60
aaagtaagaa aaaggcacag caagcagcag ctgacacagg aaacaacagc caggtcagcc     120
aaaattaccc tatagtgcag aacctccagg ggcaaatggt                           160

<210> SEQ ID NO 230
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230
agataaggta gaggaagagc aaaacaaaag taagaaaaag gcacagcaag cagcagctga      60
cacaggaaac aacagccagg tcagccaaaa ttaccctata gtgcagaacc tccaggggca     120
aatggt                                                               126

<210> SEQ ID NO 231
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (80)..(80)
<223> OTHER INFORMATION: a, c, t, g, unknown or other
<220> FEATURE:
<221> NAME/KEY: modified_base
<222> LOCATION: (85)..(85)
<223> OTHER INFORMATION: a, c, t, g, unknown or other

<400> SEQUENCE: 231
agataaggta gaggaggagc aaaacaaaag taagaaaaag gcacagcaag cagcagctga      60
cacaggaaac aacagccagn tcagncaata tagtgcagaa catccagggg caaatggt       118

<210> SEQ ID NO 232
<211> LENGTH: 33
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 232
ttggcagaac tacacaccag ggccaggggt cag                                    33

<210> SEQ ID NO 233
<211> LENGTH: 404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233
gatgaccctg agagagaagt gttagagtgg aggtttgaca gccgcctagc atttcatcac      60
gtggcccgag agctgcatcc ggagtacttc aagaactgct gacatcgagc ttgctacaag     120
ggactttccg ctggggactt tccagggagg cgtggcctgg gcgggactgg ggagtggcga     180
gccctcagat gctgcatata agcagctgct ttttgcctgt actgggtctc tctggttaga     240
ccagatctga gcctgggagc tctctggcta actagggaac ccactgctta agcctcaata     300
aagcttgcct tgagtgcttc aagtagtgtg tgcccgtctg ttgtgtgact ctggtaacta     360
gagatccctc agaccctttt agtcagtgtg gaaaatctct agca                      404

<210> SEQ ID NO 234
<211> LENGTH: 546
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(6)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (62)..(62)
<223> OTHER INFORMATION: a, c, t, g, unknown or other
<220> FEATURE:
<221> NAME/KEY: modified_base
<222> LOCATION: (65)..(67)
<223> OTHER INFORMATION: a, c, t, g, unknown or other
<220> FEATURE:
<221> NAME/KEY: modified_base
<222> LOCATION: (70)..(70)
<223> OTHER INFORMATION: a, c, t, g, unknown or other
<220> FEATURE:
<221> NAME/KEY: modified_base
<222> LOCATION: (74)..(74)
<223> OTHER INFORMATION: a, c, t, g, unknown or other
<220> FEATURE:
<221> NAME/KEY: modified_base
<222> LOCATION: (133)..(133)
<223> OTHER INFORMATION: a, c, t, g, unknown or other
<220> FEATURE:
<221> NAME/KEY: modified_base
<222> LOCATION: (224)..(224)
<223> OTHER INFORMATION: a, c, t, g, unknown or other
<220> FEATURE:
<221> NAME/KEY: modified_base
<222> LOCATION: (248)..(248)
<223> OTHER INFORMATION: a, c, t, g, unknown or other

```
<220> FEATURE:
<221> NAME/KEY: modified_base
<222> LOCATION: (253)..(253)
<223> OTHER INFORMATION: a, c, t, g, unknown or other
<220> FEATURE:
<221> NAME/KEY: modified_base
<222> LOCATION: (256)..(256)
<223> OTHER INFORMATION: a, c, t, g, unknown or other
<220> FEATURE:
<221> NAME/KEY: modified_base
<222> LOCATION: (261)..(262)
<223> OTHER INFORMATION: a, c, t, g, unknown or other
<220> FEATURE:
<221> NAME/KEY: modified_base
<222> LOCATION: (274)..(274)
<223> OTHER INFORMATION: a, c, t, g, unknown or other
<220> FEATURE:
<221> NAME/KEY: modified_base
<222> LOCATION: (286)..(286)
<223> OTHER INFORMATION: a, c, t, g, unknown or other
<220> FEATURE:
<221> NAME/KEY: modified_base
<222> LOCATION: (294)..(298)
<223> OTHER INFORMATION: a, c, t, g, unknown or other
<220> FEATURE:
<221> NAME/KEY: modified_base
<222> LOCATION: (303)..(303)
<223> OTHER INFORMATION: a, c, t, g, unknown or other
<220> FEATURE:
<221> NAME/KEY: modified_base
<222> LOCATION: (321)..(321)
<223> OTHER INFORMATION: a, c, t, g, unknown or other
<220> FEATURE:
<221> NAME/KEY: modified_base
<222> LOCATION: (337)..(337)
<223> OTHER INFORMATION: a, c, t, g, unknown or other
<220> FEATURE:
<221> NAME/KEY: modified_base
<222> LOCATION: (358)..(358)
<223> OTHER INFORMATION: a, c, t, g, unknown or other
<220> FEATURE:
<221> NAME/KEY: modified_base
<222> LOCATION: (360)..(360)
<223> OTHER INFORMATION: a, c, t, g, unknown or other
<220> FEATURE:
<221> NAME/KEY: modified_base
<222> LOCATION: (365)..(365)
<223> OTHER INFORMATION: a, c, t, g, unknown or other
<220> FEATURE:
<221> NAME/KEY: modified_base
<222> LOCATION: (383)..(383)
<223> OTHER INFORMATION: a, c, t, g, unknown or other
<220> FEATURE:
<221> NAME/KEY: modified_base
<222> LOCATION: (385)..(385)
<223> OTHER INFORMATION: a, c, t, g, unknown or other
<220> FEATURE:
<221> NAME/KEY: modified_base
<222> LOCATION: (396)..(396)
<223> OTHER INFORMATION: a, c, t, g, unknown or other
<220> FEATURE:
<221> NAME/KEY: modified_base
<222> LOCATION: (401)..(401)
<223> OTHER INFORMATION: a, c, t, g, unknown or other
<220> FEATURE:
<221> NAME/KEY: modified_base
<222> LOCATION: (418)..(418)
<223> OTHER INFORMATION: a, c, t, g, unknown or other
<220> FEATURE:
<221> NAME/KEY: modified_base
<222> LOCATION: (421)..(421)
<223> OTHER INFORMATION: a, c, t, g, unknown or other
<220> FEATURE:
<221> NAME/KEY: modified_base
<222> LOCATION: (446)..(446)
<223> OTHER INFORMATION: a, c, t, g, unknown or other
<220> FEATURE:
<221> NAME/KEY: modified_base
<222> LOCATION: (451)..(451)
```

```
<223> OTHER INFORMATION: a, c, t, g, unknown or other
<220> FEATURE:
<221> NAME/KEY: modified_base
<222> LOCATION: (455)..(455)
<223> OTHER INFORMATION: a, c, t, g, unknown or other
<220> FEATURE:
<221> NAME/KEY: modified_base
<222> LOCATION: (466)..(466)
<223> OTHER INFORMATION: a, c, t, g, unknown or other
<220> FEATURE:
<221> NAME/KEY: modified_base
<222> LOCATION: (470)..(470)
<223> OTHER INFORMATION: a, c, t, g, unknown or other
<220> FEATURE:
<221> NAME/KEY: modified_base
<222> LOCATION: (472)..(472)
<223> OTHER INFORMATION: a, c, t, g, unknown or other
<220> FEATURE:
<221> NAME/KEY: modified_base
<222> LOCATION: (489)..(489)
<223> OTHER INFORMATION: a, c, t, g, unknown or other
<220> FEATURE:
<221> NAME/KEY: modified_base
<222> LOCATION: (495)..(495)
<223> OTHER INFORMATION: a, c, t, g, unknown or other
<220> FEATURE:
<221> NAME/KEY: modified_base
<222> LOCATION: (501)..(501)
<223> OTHER INFORMATION: a, c, t, g, unknown or other
<220> FEATURE:
<221> NAME/KEY: modified_base
<222> LOCATION: (503)..(506)
<223> OTHER INFORMATION: a, c, t, g, unknown or other
<220> FEATURE:
<221> NAME/KEY: modified_base
<222> LOCATION: (508)..(508)
<223> OTHER INFORMATION: a, c, t, g, unknown or other
<220> FEATURE:
<221> NAME/KEY: modified_base
<222> LOCATION: (518)..(518)
<223> OTHER INFORMATION: a, c, t, g, unknown or other
<220> FEATURE:
<221> NAME/KEY: modified_base
<222> LOCATION: (525)..(525)
<223> OTHER INFORMATION: a, c, t, g, unknown or other
<220> FEATURE:
<221> NAME/KEY: modified_base
<222> LOCATION: (529)..(529)
<223> OTHER INFORMATION: a, c, t, g, unknown or other
<220> FEATURE:
<221> NAME/KEY: modified_base
<222> LOCATION: (534)..(534)
<223> OTHER INFORMATION: a, c, t, g, unknown or other
<220> FEATURE:
<221> NAME/KEY: modified_base
<222> LOCATION: (540)..(546)
<223> OTHER INFORMATION: a, c, t, g, unknown or other

<400> SEQUENCE: 234
nnnnnncana nacttagatc attatataat acaatagcag tcctctattg tgtgcacctg      60
gnccnnntgn tgcntccgga ttacttcaag aactgctgac atctagcttg ctacaaggga     120
ctttccgctg ggnactttcc agggaggcgt ggcctgggcg gtactggcta gtgccgatcc     180
ctccaaagct ggaaaaaaac gcctgctttt tacatgacct gggnctctta caccctgcca     240
gatttgangg aanggnctct nnggctaact aagnaaccca ctgctnaatt cttnnnnnct     300
acntttcatc cgtggcccca ncgctgcatc ctgagtnggt gaaaaactgc tgacatcnan     360
cttgntacaa gggattttcc acngnggggt ttcccngggg nggtgtgccg ggggcganag     420 ngggagtgg  ggaccctca tatgcnacaa naaanagccg cttttngcgn gnaagggctc     480
tctctttanc accanatctg ntnnnngnct ctctggtngt ggggncccnt gctnatttcn     540 nnnnnn                                                               546
```

```
<210> SEQ ID NO 235
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gacagctaca accatccctt cagacaggat                                        30

<210> SEQ ID NO 236
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
aaaggataga tgtaaaagac accaaggaag cct                                    33

<210> SEQ ID NO 237
<211> LENGTH: 249
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 237
aagagaccat caatgaggaa gctgcagaat gggatagatt gcatccagtg catgcagggc       60
ctattgcacc aggccagatg agagaaccaa ggggaagtga catagcagga actactagta      120
aagaccaatg acttacaagg cagctgtaga tcttagccac tttttaaaag aaaaggggggg     180 actggaaggg ctaattcact cccaaagaag acaagatatc cttgatctgt ggatctacca      240
cacacaagg                                                             249

<210> SEQ ID NO 238
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (53)..(53)
<223> OTHER INFORMATION: a, c, t, g, unknown or other
<220> FEATURE:
<221> NAME/KEY: modified_base
<222> LOCATION: (56)..(56)
<223> OTHER INFORMATION: a, c, t, g, unknown or other

<400> SEQUENCE: 238
aagagaccat ctctctggtt agaccaaatc tgagcctggg agctctctgg ctnctnggga       60
acccgctgct gg                                                          72

<210> SEQ ID NO 239
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<221> NAME/KEY: modified_base
<222> LOCATION: (1)..(5)
<223> OTHER INFORMATION: a, c, t, g, unknown or other
<220> FEATURE:
<221> NAME/KEY: modified_base
<222> LOCATION: (7)..(10)
<223> OTHER INFORMATION: a, c, t, g, unknown or other
<220> FEATURE:
<221> NAME/KEY: modified_base
<222> LOCATION: (12)..(16)
<223> OTHER INFORMATION: a, c, t, g, unknown or other
<220> FEATURE:
<221> NAME/KEY: modified_base
<222> LOCATION: (18)..(26)
<223> OTHER INFORMATION: a, c, t, g, unknown or other
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: modified_base
<222> LOCATION: (35)..(37)
<223> OTHER INFORMATION: a, c, t, g, unknown or other
<220> FEATURE:
<221> NAME/KEY: modified_base
<222> LOCATION: (40)..(40)
<223> OTHER INFORMATION: a, c, t, g, unknown or other
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: modified_base
<222> LOCATION: (50)..(50)
<223> OTHER INFORMATION: a, c, t, g, unknown or other
<220> FEATURE:
<221> NAME/KEY: modified_base
<222> LOCATION: (53)..(54)
<223> OTHER INFORMATION: a, c, t, g, unknown or other
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (63)..(63)
<223> OTHER INFORMATION: a, c, t, g, unknown or other

<400> SEQUENCE: 239
nnnnnannnn annnnncnnn nnnnnnatnn annannnatn tnggaagggn tanntcactc        60
ncnaagcaag acaagatatc cttgatctgt ggatctacca cacacaagg                   109

<210> SEQ ID NO 240
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
ttggcagaac tacacaccag ggccaggggt cag                                    33

<210> SEQ ID NO 241
<211> LENGTH: 28
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 241
tctctggcta actagggaac ccactgct                                                28

<210> SEQ ID NO 242
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (19)..(21)
<223> OTHER INFORMATION: a, c, t, g, unknown or other

<400> SEQUENCE: 242
tctcnggcta anggggggnn nac                                                     23

<210> SEQ ID NO 243
<211> LENGTH: 518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 243
tggaagggct aattcactcc caaagaagac aagatatcct tgatctgtgg atctaccaca         60
cacaaggcta cttccctgat tggcagaact acacaccagg gccaggggtc agatatccac        120
tgacctttgg atggtgctac aagctagtac cagttgagcc agataaggta gaagaggcca        180
ataaaggaga gaacaccagc ttgttacacc ctgtgagcct gcatggaatg gatgaccctg        240
agagagaagt gttagagtgg aggtttgaca gccgcctagc atttcatcac gtggcccgag        300
agctgcatcc ggagtacttc aagaactgct gacatcgagc ttgctacaag ggactttccg        360
ctggggactt tccagggagg cgtggcctgg gcgggactgg ggagtggcga gccctcagat        420
gctgcatata agcagctgct ttttgcctgt actgggtctc tctggttaga ccagatctga        480
gcctgggagc tctctggcta actagggaac ccactgct                                 518

<210> SEQ ID NO 244
<211> LENGTH: 480
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(34)
<223> OTHER INFORMATION: a, c, t, g, unknown or other
<220> FEATURE:
<221> NAME/KEY: modified_base
<222> LOCATION: (38)..(45)
<223> OTHER INFORMATION: a, c, t, g, unknown or other
<220> FEATURE:
<221> NAME/KEY: modified_base
<222> LOCATION: (47)..(47)

-continued

```
<223> OTHER INFORMATION: a, c, t, g, unknown or other
<220> FEATURE:
<221> NAME/KEY: modified_base
<222> LOCATION: (49)..(57)
<223> OTHER INFORMATION: a, c, t, g, unknown or other
<220> FEATURE:
<221> NAME/KEY: modified_base
<222> LOCATION: (89)..(89)
<223> OTHER INFORMATION: a, c, t, g, unknown or other
<220> FEATURE:
<221> NAME/KEY: modified_base
<222> LOCATION: (91)..(91)
<223> OTHER INFORMATION: a, c, t, g, unknown or other
<220> FEATURE:
<221> NAME/KEY: modified_base
<222> LOCATION: (215)..(215)
<223> OTHER INFORMATION: a, c, t, g, unknown or other
<220> FEATURE:
<221> NAME/KEY: modified_base
<222> LOCATION: (283)..(283)
<223> OTHER INFORMATION: a, c, t, g, unknown or other
<220> FEATURE:
<221> NAME/KEY: modified_base
<222> LOCATION: (312)..(312)
<223> OTHER INFORMATION: a, c, t, g, unknown or other
<220> FEATURE:
<221> NAME/KEY: modified_base
<222> LOCATION: (317)..(317)
<223> OTHER INFORMATION: a, c, t, g, unknown or other
<220> FEATURE:
<221> NAME/KEY: modified_base
<222> LOCATION: (322)..(322)
<223> OTHER INFORMATION: a, c, t, g, unknown or other
<220> FEATURE:
<221> NAME/KEY: modified_base
<222> LOCATION: (326)..(326)
<223> OTHER INFORMATION: a, c, t, g, unknown or other
<220> FEATURE:
<221> NAME/KEY: modified_base
<222> LOCATION: (345)..(346)
<223> OTHER INFORMATION: a, c, t, g, unknown or other
<220> FEATURE:
<221> NAME/KEY: modified_base
<222> LOCATION: (351)..(351)
<223> OTHER INFORMATION: a, c, t, g, unknown or other
<220> FEATURE:
<221> NAME/KEY: modified_base
<222> LOCATION: (362)..(362)
<223> OTHER INFORMATION: a, c, t, g, unknown or other
<220> FEATURE:
<221> NAME/KEY: modified_base
<222> LOCATION: (387)..(387)
<223> OTHER INFORMATION: a, c, t, g, unknown or other
<220> FEATURE:
<221> NAME/KEY: modified_base
<222> LOCATION: (409)..(409)
<223> OTHER INFORMATION: a, c, t, g, unknown or other
<220> FEATURE:
<221> NAME/KEY: modified_base
<222> LOCATION: (417)..(417)
<223> OTHER INFORMATION: a, c, t, g, unknown or other
<220> FEATURE:
<221> NAME/KEY: modified_base
<222> LOCATION: (419)..(419)
<223> OTHER INFORMATION: a, c, t, g, unknown or other
<220> FEATURE:
<221> NAME/KEY: modified_base
<222> LOCATION: (421)..(423)
<223> OTHER INFORMATION: a, c, t, g, unknown or other
<220> FEATURE:
<221> NAME/KEY: modified_base
<222> LOCATION: (425)..(425)
<223> OTHER INFORMATION: a, c, t, g, unknown or other
<220> FEATURE:
<221> NAME/KEY: modified_base
<222> LOCATION: (427)..(427)
<223> OTHER INFORMATION: a, c, t, g, unknown or other
<220> FEATURE:
<221> NAME/KEY: modified_base
```

```
<222> LOCATION: (442)..(442)
<223> OTHER INFORMATION: a, c, t, g, unknown or other
<220> FEATURE:
<221> NAME/KEY: modified_base
<222> LOCATION: (449)..(449)
<223> OTHER INFORMATION: a, c, t, g, unknown or other
<220> FEATURE:
<221> NAME/KEY: modified_base
<222> LOCATION: (451)..(451)
<223> OTHER INFORMATION: a, c, t, g, unknown or other
<220> FEATURE:
<221> NAME/KEY: modified_base
<222> LOCATION: (454)..(454)
<223> OTHER INFORMATION: a, c, t, g, unknown or other
<220> FEATURE:
<221> NAME/KEY: modified_base
<222> LOCATION: (457)..(457)
<223> OTHER INFORMATION: a, c, t, g, unknown or other
<220> FEATURE:
<221> NAME/KEY: modified_base
<222> LOCATION: (469)..(469)
<223> OTHER INFORMATION: a, c, t, g, unknown or other
<220> FEATURE:
<221> NAME/KEY: modified_base
<222> LOCATION: (474)..(474)
<223> OTHER INFORMATION: a, c, t, g, unknown or other

<400> SEQUENCE: 244
nnnnnnnnnn nnnnnnnnnn nnnnnnnnnn nnnnaacnnn nnnnngngnn nnnnnnntcc        60
caaagaacac aatatatcct tgatctaana natctaccac acacaaggct acttccctga       120
ttggcagaac tacacaccag ggccaggggt cagataccca ctgatctttg gatggtgcta       180
caagctagta ccagttgagc cagataaggt agaanaggcc aataaaggaa agaacaccag       240
cttgttacac cctgtgagcc tgcatggaat ggatgaccct ganagagaaa tgttagagtg       300
gaggtttgac anccccntag cntttnttca cgtggcccca gagcnncttc nggagtactt       360
cncaagaagc gcagacctag cttgttnggg tggagaatcc ccgggggggnt tttcagngna       420 nnntncnggg aggggggactg gngagtgana nccncanatg ctgatatanc tctnttttttg      480
```

```
<210> SEQ ID NO 245
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
gacagctaca accatccctt cagacaggat                                        30
```

```
<210> SEQ ID NO 246
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
aaaggataga tgtaaaagac accaaggaag cct                                    33
```

```
<210> SEQ ID NO 247
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 247
tgcaaatgtt aaa                                                                           13

<210> SEQ ID NO 248
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gaaatctata aaa                                                                           13

<210> SEQ ID NO 249
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(11)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other

<400> SEQUENCE: 249
aaaggatann nttnaaanac acccaggagt cct                                                     33

<210> SEQ ID NO 250
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
aaaggataat agtaaaagac accaaggaag cct                                                     33

<210> SEQ ID NO 251
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
gaaatctata                                                                              10

<210> SEQ ID NO 252
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252

-continued aaaggataaa tgtaaaagac accaaggaag cct                              33

<210> SEQ ID NO 253
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
tgcaaatgtt                                                        10

<210> SEQ ID NO 254
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ttggcagaac tacacaccag ggccaggggt cag                             33

<210> SEQ ID NO 255
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
ggagtggcga gcc                                                    13

<210> SEQ ID NO 256
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
ggagctctct ggctaactag ggaacccact gct                             33

<210> SEQ ID NO 257
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (17)..(18)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 257
gnacctctct ggctaannan gnaacccact gtg                                    33

<210> SEQ ID NO 258
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(29)
<223> OTHER INFORMATION: a, c, t, g, unknown or other

<400> SEQUENCE: 258
gctctctggc taactaggga acccactgng                                        30

<210> SEQ ID NO 259
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
gtggcgagcc                                                              10

<210> SEQ ID NO 260
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
acagctacaa ccatcccttc agacaggat                                         29

<210> SEQ ID NO 261
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
aaaggataga tgtaaaagac accaaggaag cctt                                   34

<210> SEQ ID NO 262
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
agaccatcaa                                                              10

<210> SEQ ID NO 263
<211> LENGTH: 33
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 263
ttggcagaac tacacaccag ggccaggggt cag                                  33

<210> SEQ ID NO 264
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(12)
<223> OTHER INFORMATION: a, c, t, g, unknown or other
<220> FEATURE:
<221> NAME/KEY: modified_base
<222> LOCATION: (14)..(15)
<223> OTHER INFORMATION: a, c, t, g, unknown or other

<400> SEQUENCE: 264
aaaggatagn nntnnaagac accaaggaag cct                                  33

<210> SEQ ID NO 265
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
ggtctctctg gttagaccag atctgagcct gggagctctc tggctaacta gggaacccac    60
tgct                                                                 64

<210> SEQ ID NO 266
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ctctctggtt agaccagatc tgagcctggg agctctctgg ctaactaggg aacccactgc    60
t                                                                    61

<210> SEQ ID NO 267
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
tggaagggct aatttggtcc caaaaaa                                         27

<210> SEQ ID NO 268
<211> LENGTH: 37
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 268
ttggcagaac tacacaccag ggccagggat cagatat                                37

<210> SEQ ID NO 269
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
accagatctg agcctgggag ctctctg                                           27

<210> SEQ ID NO 270
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
tggaagggct aattcactcc caacgaa                                           27

<210> SEQ ID NO 271
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
accagatctg agcctgggag ctctcgg                                           27

<210> SEQ ID NO 272
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ttggcagaac tacacaccag ccagggatca gatat                                  35

<210> SEQ ID NO 273
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
ttggcagaac tacacaccag ggatcagata t                                      31

<210> SEQ ID NO 274
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 274
ttggcagaac tacacaccag gccagggatc agatat                              36

<210> SEQ ID NO 275
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ttggcagaac tacacaccag gccagggatc agatat                              36

<210> SEQ ID NO 276
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
ttggcagaac tacacaccag gtat                                           24

<210> SEQ ID NO 277
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ttggcagaac tacacacgcc agggatcaga tat                                 33

<210> SEQ ID NO 278
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ttggcagaac tacacaccag ccagggatca gatat                               35

<210> SEQ ID NO 279
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 279
ttggcagaac tacacaccag gcaatggaaa gtccctattg gcgttactat gggaacatac   60
gtcattattg acgtcaatgg gcgggggtcg ttgggcggtc agccaggcgg gccatttacc   120
gtaagttatg taacgcggaa ctccatatat gggctatgaa ctaatgaccc cgtaattgat   180
tactattaat aactagtcaa taatcaatgt caacgcctcg agtctagagg ccgcaggaac   240
ccctagtgat ggagttggcc actccctctc tgcgcgctcg ctcgctcact gaggccgggc   300
gaccaaaggt cgcccggggc cagggatcag atat                                334
```

```
<210> SEQ ID NO 280
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 280
ttggcagaac tacacaccag gaaaggtcgc ccgacgcccg ggcggcctca gtgagcgagc      60
gagcgcgcag ctgcctgcag gacatgtgag caaaaggcca gcgccaggga tcagatat        118

<210> SEQ ID NO 281
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281
ttggcagaac tacacaccag gaaaggtcgc ccgacgcccg ggcggcctca gtgagcgggc      60
gagcgcgcag ctgcctgcag gacatgtgag caaaaggcca gcgccaggga tcagatat        118

<210> SEQ ID NO 282
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 282
ttggcagaac tacacaccag gaaaggtcgc ccgacgcccg ggcggcctca gtgagcgggc      60
gagcgcgcag ctgcctgcag gacatgtgag caaaaggcca gcgccaggga tcagatat        118

<210> SEQ ID NO 283
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ttggcagaac tacacaccag ggccagggat cag                                    33

<210> SEQ ID NO 284
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ttggcagaac tacacaccag ggccagggat cag                                    33

<210> SEQ ID NO 285
<211> LENGTH: 27
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 285
ttggcagaac tacacaccag ggatcag                                            27

<210> SEQ ID NO 286
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
ttggcagaac tacacaccag gccagggatc ag                                      32

<210> SEQ ID NO 287
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
ttggcagaac tacacacgcc aggatcag                                           29

<210> SEQ ID NO 288
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
ttggcagaac tacacaccag ccagggatca g                                       31

<210> SEQ ID NO 289
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
ttggcagaac tacacacgcc aggatcag                                           29

<210> SEQ ID NO 290
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
ttggcagaac tacacaccag ccagggatca g                                       31

<210> SEQ ID NO 291
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
gtcacagcac tccccaccag ggcttggggg caa                                33

<210> SEQ ID NO 292
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
gtcacagcac tccccaccag ggcttggggg caa                                33

<210> SEQ ID NO 293
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
actaccctgg gctctggtct gtaggtttgt agt                                33

<210> SEQ ID NO 294
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
actaccctgg gctctggtct gtaggtttgt agt                                33

<210> SEQ ID NO 295
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
gaacttcatg gccctggtgt ggagtttaga gtt                                33

<210> SEQ ID NO 296
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
gaacttcatg gccctggtgt ggagtttaga gtt                                33

<210> SEQ ID NO 297
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 297
aggccaaaga tgaaaaagac acccgagaaa ctt                            33

<210> SEQ ID NO 298
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
aggccaaaga tgaaaaagac acccgagaaa ctt                            33

<210> SEQ ID NO 299
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
taatgagact tgtacaagac accacggggc tt                             32

<210> SEQ ID NO 300
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
taatgagact tgtacaagac accacggggc tt                             32

<210> SEQ ID NO 301
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
tgcagaaaaa tgtaaaagac accttggaaa aa                             32

<210> SEQ ID NO 302
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
tgcagaaaaa tgtaaaagac accttggaaa aa                             32

<210> SEQ ID NO 303
<211> LENGTH: 27
<212> TYPE: DNA
<213> ORGANISM: Human immunodeficiency virus 1

<400> SEQUENCE: 303
gcagaactac acaccagggc cagggat                                   27
```

<210> SEQ ID NO 304
<211> LENGTH: 27
<212> TYPE: DNA
<213> ORGANISM: Human immunodeficiency virus 1

<400> SEQUENCE: 304
ggatagatgt aaaagacacc aaggaag                                           27

<210> SEQ ID NO 305
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
aaagtagcag gaccacttct gcgctcggcc cttccggctg g                           41

<210> SEQ ID NO 306
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 306
gttacatcga actggatctc aacagcggta agatccttga tgtaacccac tcgtgcaccc       60
aactgatctt cagcatctgg tgctgtgctg acaactggta gttcctgccc tacatcttcc      120
ccagaagcgt gtccttcgac aacagcttca acaacaaggt                            160

<210> SEQ ID NO 307
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 307
caatggaaag tccctattgg cgttactatg ggaacatacg tcattattga cgtcaatggg       60
cgggggtcgt tgggcggtca gccaggcggg ccatttaccg taagttatgt aacgcggaac      120
tccatatatg ggctatgaac taatgacccc gtaattgatt actattaata actagtcaat      180
aatcaatgtc aacgcctcga gtctagaggc cgcaggaacc cctagtgatg gagttggcca      240
ctccctctct gcgcgctcgc tcgctcactg aggccgggcg accaaaggtc gcccggg         297

<210> SEQ ID NO 308
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
aaaggtcgcc cgacgcccgg gcggcctcag tgagcgagcg agcgcgcagc tgcctgcagg       60
acatgtgagc aaaaggccag c                                                81

<210> SEQ ID NO 309
<211> LENGTH: 81

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
aaaggtcgcc cgacgcccgg gcggcctcag tgagcgggcg agcgcgcagc tgcctgcagg        60
acatgtgagc aaaaggccag c                                                  81

<210> SEQ ID NO 310
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
aaaggtcgcc cgacgcccgg gcggcctcag tgagcgggcg agcgcgcagc tgcctgcagg        60
acatgtgagc aaaaggccag c                                                  81
```

HIV-1 ERADICATION STRATEGY EMPLOYING NANOFORMULATED ANTI-RETROVIRAL DRUGS AND GENE EDITING AGENTS

CROSS REFERENCE TO RELATED APPLICATIONS

This application is the U.S. National Stage Application, filed under 35 U.S.C. § 371, of PCT International Patent Application No. PCT/US2018/026716, filed Apr. 9, 2018, which claims the benefit of U.S. Provisional Application 62/486,237 filed on Apr. 17, 2017 and U.S. Provisional Application 62/524,218, filed Jun. 23, 2017, the entire contents of which are incorporated herein by reference in its entirety.

STATEMENT REGARDING FEDERALLY SPONSORED RESEARCH

This invention was made with government support under P30 MH092177 and R01 MH115860 awarded by the National Institutes of Health. The government has certain rights in this invention.

INCORPORATION BY REFERENCE OF SEQUENCE LISTING

The instant application contains a Sequence Listing which has been submitted electronically in ASCII format and is hereby incorporated by reference in its entirety. Said ASCII copy, created on Jul. 5, 2022, is named 348382_00101_SL.txt and is 77,770 bytes in size.

FIELD OF THE INVENTION

A combination therapy for the elimination and eradication of a retrovirus, for example, HIV, from an infected subject. In particular, the therapeutic approach utilizes long-acting slow effective release antiretroviral therapy (called LASER ART) and a gene editing agent.

BACKGROUND

The elimination of the human immunodeficiency virus (HIV) from its viral reservoirs is a requirement for disease cure. Cure is defined as undetectable viremia measured in time periods of years in the absence of antiretroviral therapy (ART).

SUMMARY

Embodiments of the invention are directed to a combination therapy comprising antiretroviral therapy (ART) along with gene editing.

In certain embodiments, a method of eradicating a retrovirus in a subject, comprises administering to a patient a composition comprising a therapeutically effective amount of at least one antiretroviral agent and/or a composition comprising a therapeutically effective amount of at least one gene editing agent. In certain embodiments, the antiretroviral or anti-viral agent is formulated as a long-acting slow effective release (LASER) antiretroviral agent. In certain embodiments, the at least one antiretroviral or anti-viral agent agent is nanoformulated. In certain embodiments, the at least one antiretroviral or anti-viral agent comprises: myristoylated dolutegravir, lamivudine, abacavir, rilpivirine or combinations thereof.

In certain embodiments, at least one antiretroviral agent is administered to the subject prior to administering the at least one gene editing agent. In certain embodiments, the at least one antiretroviral agent and at least one gene-editing agent are co-administered. In certain embodiments, the at least one antiretroviral agent and at least one gene-editing agent are administered sequentially.

In certain embodiments, the at least one gene editing agent comprises: an isolated nucleic acid sequence encoding a Clustered Regularly Interspaced Short Palindromic Repeat (CRISPR)-associated endonuclease/Cas (CRISPR/Cas) and at least one guide RNA (gRNA), the gRNA being complementary to a target nucleic acid sequence in a retroviral genome.

In certain embodiments, the CRISPR/Cas fusion protein comprises catalytically deficient Cas protein (dCas), orthologs, homologs, mutants variants or fragments thereof.

In certain embodiments, the at least one gRNA includes at least a first gRNA that is complementary to a target sequence in the integrated retroviral DNA; and a second gRNA that is complementary to another target sequence in the integrated retroviral DNA, whereby the intervening sequences between the two gRNAs are removed.

In certain embodiments, the isolated nucleic acid is included in at least one expression vector. In certain embodiments, the expression vector comprises a lentiviral vector, an adenoviral vector, or an adeno-associated virus vector. In certain embodiments the vector is an adeno-associated vector, e.g. $AAV_9$.

In certain embodiments, the retrovirus is a human immunodeficiency virus (HIV).

In certain embodiments, the target sequences comprise one or more nucleic acid sequences in HIV comprising: long terminal repeat (LTR) nucleic acid sequences, nucleic acid sequences encoding structural proteins, non-structural proteins or combinations thereof.

In certain embodiments, the sequences encoding structural proteins comprise nucleic acid sequences encoding: Gag, Gag-Pol precursor, Pro (protease), Reverse Transcriptase (RT), integrase (In), Env or combinations thereof. In certain embodiments, the sequences encoding non-structural proteins comprise nucleic acid sequences encoding: regulatory proteins, accessory proteins or combinations thereof. In certain embodiments, the regulatory proteins comprise: Tat, Rev or combinations thereof. In certain embodiments, the accessory proteins comprise Nef, Vpr, Vpu, Vif or combinations thereof.

In certain embodiments, a gRNA comprises at least one nucleic acid sequence set forth in Tables 1-5 or combinations of gRNAs.

In certain embodiments, a composition further comprises a therapeutically effective amount of a non-nucleoside reverse transcriptase inhibitor (NNRTI), and/or a nucleoside reverse transcriptase inhibitor (NRTI) and/or a protease inhibitor. In certain embodiments, the NNRTI comprises: etravirine, efavirenz, nevirapine, rilpivirine, delavirdine, or nevirapine. In certain embodiments, the NRTI comprises: lamivudine, zidovudine, emtricitabine, abacavir, zalcitabine, dideoxycytidine, azidothymidine, tenofovir disoproxil fumarate, didanosine (ddI EC), dideoxyinosine, stavudine, abacavir sulfate or combinations thereof. In certain embodiments, a protease inhibitor comprises: amprenavir, tipranavir, indinavir, saquinavir mesylate, lopinavir and ritonavir (LPV/RTV), Fosamprenavir Calcium (FOS-APV), ritonavir, darunavir, atazanavir sulfate, nelfinavir mesylate or combinations thereof.

In certain embodiments, the pharmaceutical composition comprising a therapeutically effective amount of a nanoformulated long-acting slow effective release antiretroviral agent. In certain embodiments, the nanoformulated antiretroviral agent comprises: myristoylated dolutegravir, lamivudine, abacavir, rilpivirine or combinations thereof. In certain embodiments, the pharmaceutical composition comprises at least one an isolated nucleic acid sequence encoding a Clustered Regularly Interspaced Short Palindromic Repeat (CRISPR)-associated endonuclease; at least one isolated nucleic acid sequence encoding at least one guide RNA (gRNA) that is complementary to a target sequence in retroviral DNA; said isolated nucleic acid sequences being included in at least one expression vector. In certain embodiments the pharmaceutical composition comprise the gene-editing agent.

In certain embodiments, the integrated retroviral DNA is human immunodeficiency virus (HIV) DNA, and said at least one gRNA includes a first gRNA that is complementary to a first target sequence in the HIV DNA, and a second gRNA that is complementary to a second target sequence in the HIV DNA.

Other aspects are described infra.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element. Thus, recitation of "a cell", for example, includes a plurality of the cells of the same type. Furthermore, to the extent that the terms "including", "includes", "having", "has", "with", or variants thereof are used in either the detailed description and/or the claims, such terms are intended to be inclusive in a manner similar to the term "comprising."

"About" as used herein when referring to a measurable value such as an amount, a temporal duration, and the like, is meant to encompass variations of +/−20%, +/−10%, +/−5%, +/−1%, or +/−0.1% from the specified value, as such variations are appropriate to perform the disclosed methods. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

The term "anti-viral agent" or "anti-retroviral agent" as used herein, refers to any molecule that is used for the treatment of a virus and include agents which alleviate any symptoms associated with the virus, for example, anti-pyretic agents, anti-inflammatory agents, chemotherapeutic agents, and the like. An antiviral agent includes, without limitation: antibodies, aptamers, adjuvants, anti-sense oligonucleotides, chemokines, cytokines, immune stimulating agents, immune modulating agents, B-cell modulators, T-cell modulators, NK cell modulators, antigen presenting cell modulators, enzymes, siRNA's, ribavirin, protease inhibitors, helicase inhibitors, polymerase inhibitors, helicase inhibitors, neuraminidase inhibitors, nucleoside reverse transcriptase inhibitors, non-nucleoside reverse transcriptase inhibitors, purine nucleosides, chemokine receptor antagonists, interleukins, or combinations thereof. The term also refers to non-nucleoside reverse transcriptase inhibitors (NNRTIs), nucleoside reverse transcriptase inhibitors (NRTIs), analogs, variants etc.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "eradication" of a retrovirus, e.g. human immunodeficiency virus (HIV), as used herein, means that that virus is unable to replicate, the genome is deleted, fragmented, degraded, genetically inactivated, or any other physical, biological, chemical or structural manifestation, that prevents the virus from being transmissible or infecting any other cell or subject resulting in the clearance of the virus in vivo. In some cases, fragments of the viral genome may be detectable, however, the virus is incapable of replication, or infection etc. The presence or absence of the HIV virus can be determined via any means, such as for example, p24 detection or lack thereof, etc.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes: a recombinant DNA which is part of a hybrid gene encoding additional polypeptide sequence, complementary DNA (cDNA), linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like.

The nucleic acid sequences may be "chimeric," that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide. These sequences typically comprise at least one region wherein the sequence is modified in order to exhibit one or more desired properties.

Unless otherwise specified, a "nucleotide sequence encoding" an amino acid sequence includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Optional" or "optionally" means that the subsequently described event or circumstance can or cannot occur, and that the description includes instances where the event or circumstance occurs and instances where it does not.

As used in this specification and the appended claims, the term "or" is generally employed in its sense including "and/or" unless the content clearly dictates otherwise.

"Parenteral" administration of an immunogenic composition includes, e.g., subcutaneous (s.c.), intravenous (i.v.), intramuscular (i.m.), or intrasternal injection, or infusion techniques.

The terms "patient" or "individual" or "subject" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

The term "percent sequence identity" or having "a sequence identity" refers to the degree of identity between any given query sequence and a subject sequence.

As used herein, a "pharmaceutically acceptable" component/carrier etc. is one that is suitable for use with humans and/or animals without undue adverse side effects (such as toxicity, irritation, and allergic response) commensurate with a reasonable benefit/risk ratio.

The term "target nucleic acid" sequence refers to a nucleic acid (often derived from a biological sample), to which the oligonucleotide is designed to specifically hybridize. The target nucleic acid has a sequence that is complementary to the nucleic acid sequence of the corresponding oligonucleotide directed to the target. The term target nucleic acid may refer to the specific subsequence of a larger nucleic acid to which the oligonucleotide is directed or to the overall sequence (e.g., gene or mRNA). The difference in usage will be apparent from context.

To "treat" a disease as the term is used herein, means to reduce the frequency or severity of at least one sign or symptom of a disease or disorder experienced by a subject. Treatment of a disease or disorders includes the eradication of a virus.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. Accordingly, "treating" or "treatment" of a state, disorder or condition includes: (1) eradicating the virus; (2) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (3) inhibiting the state, disorder or condition, i.e., arresting, reducing or delaying the development of the disease or a relapse thereof (in case of maintenance treatment) or at least one clinical or subclinical symptom thereof, or (4) relieving the disease, i.e., causing regression of the state, disorder or condition or at least one of its clinical or subclinical symptoms. The benefit to an individual to be treated is either statistically significant or at least perceptible to the patient or to the physician.

As defined herein, a "therapeutically effective" amount of a compound or agent (i.e., an effective dosage) means an amount sufficient to produce a therapeutically (e.g., clinically) desirable result. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

Where any amino acid sequence is specifically referred to by a Swiss Prot. or GENBANK Accession number, the sequence is incorporated herein by reference. Information associated with the accession number, such as identification of signal peptide, extracellular domain, transmembrane domain, promoter sequence and translation start, is also incorporated herein in its entirety by reference.

Genes: All genes, gene names, and gene products disclosed herein are intended to correspond to homologs from any species for which the compositions and methods disclosed herein are applicable. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, are intended to encompass homologous and/or orthologous genes and gene products from other species.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

BRIEF DESCRIPTION OF THE DRAWINGS

FIGS. 1A-1G show the viral and immune profiles from sequential LASER ART and $AAV_9$-CRISPR-Cas9 treatments of HIV-1 infected humanized mice. FIG. 1A: After infection at week 0 and confirmation of VL, mice were administered 45 mg/kg nanoformulated myristoylated DTG (NMDTG), nanoformulated RPV (NRPV) and 40 mg/kg NM3TC, NMABC. Three weeks after the last LASER ART treatment, a single IV dose of $AAV_9$-CRISPR-Cas9 ($10^{12}$GC units) was administered and left without antiretroviral drugs for an additional five weeks. FIG. 1B: Evaluation of human $CD4^+$ T cell numbers in humanized mice by flow cytometry tests on days 0, 3, 5, 7, and 14 of infection. FIG. 1C: Viral load assessment by determining viral RNA copies in plasma at day-14 after HIV-1 $NL_{4-3}$ infection and prior to LASER ART treatment. FIG. 1D: Detection of human cells and viral infection in various tissues at day-14 after infection. Stains of human HLA-DR in lymph nodes, spleen, and lung show significant human immune cell reconstitution in infected animals. Replicate slides demonstrate HIV-1 $p24^+$ stained cells in tissue sections. FIG. 1E: Detection of HIV-1 DNA by semi-nested real-time q-PCR assay in different tissues of HIV-1 infected animals at day-14 of infection. FIG. 1F: Evaluation of viral load shows that after administration of $AAV_9$-CRISPR-Cas9, two out of seven mice showed no evidence for viral rebound at week-14. Viral load in untreated animals remained high during the course of study. FIG. 1G: FACS analyses of human $CD4^+$ T cells are shown with increased numbers in the LASER ART and $AAV_9$-CRISPR-Cas9 groups. A one-way ANOVA and Bonferroni's post-hoc tests for multiple comparisons and a two-tailed Student's 1-test was used for statistical analyses in FIG. 1B. *P<0.05, **P<0.01.

FIG. 2A: Schematic illustration of HIV-1$_{NL4-3}$ DNA highlighting the positions of gRNA LTR1 and gRNA Gag D target sites, their

Figure 2A:
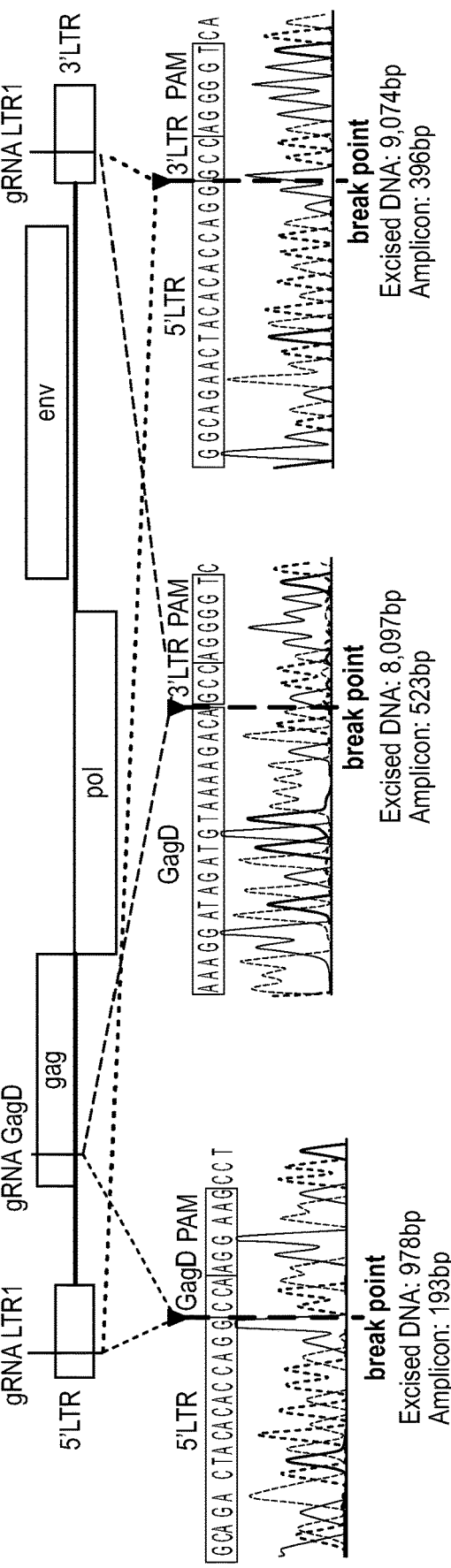
FIGS. 2A-2C show the excision of the viral DNA fragments by CRISPR-Cas9 in tissues from HIV-1 infected humanized mice treated with LASER ART.
Figure 2B:
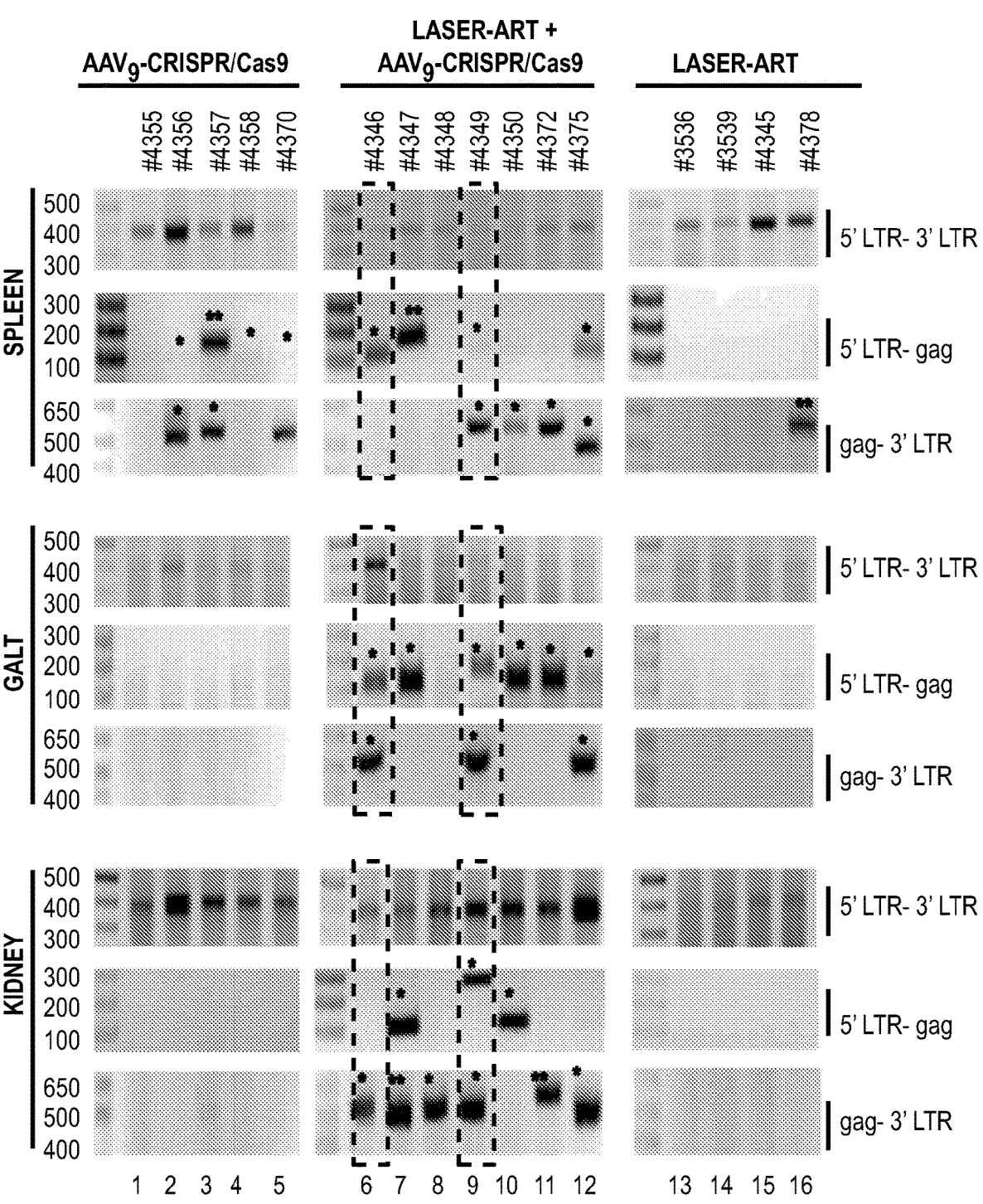
Figure 2C:
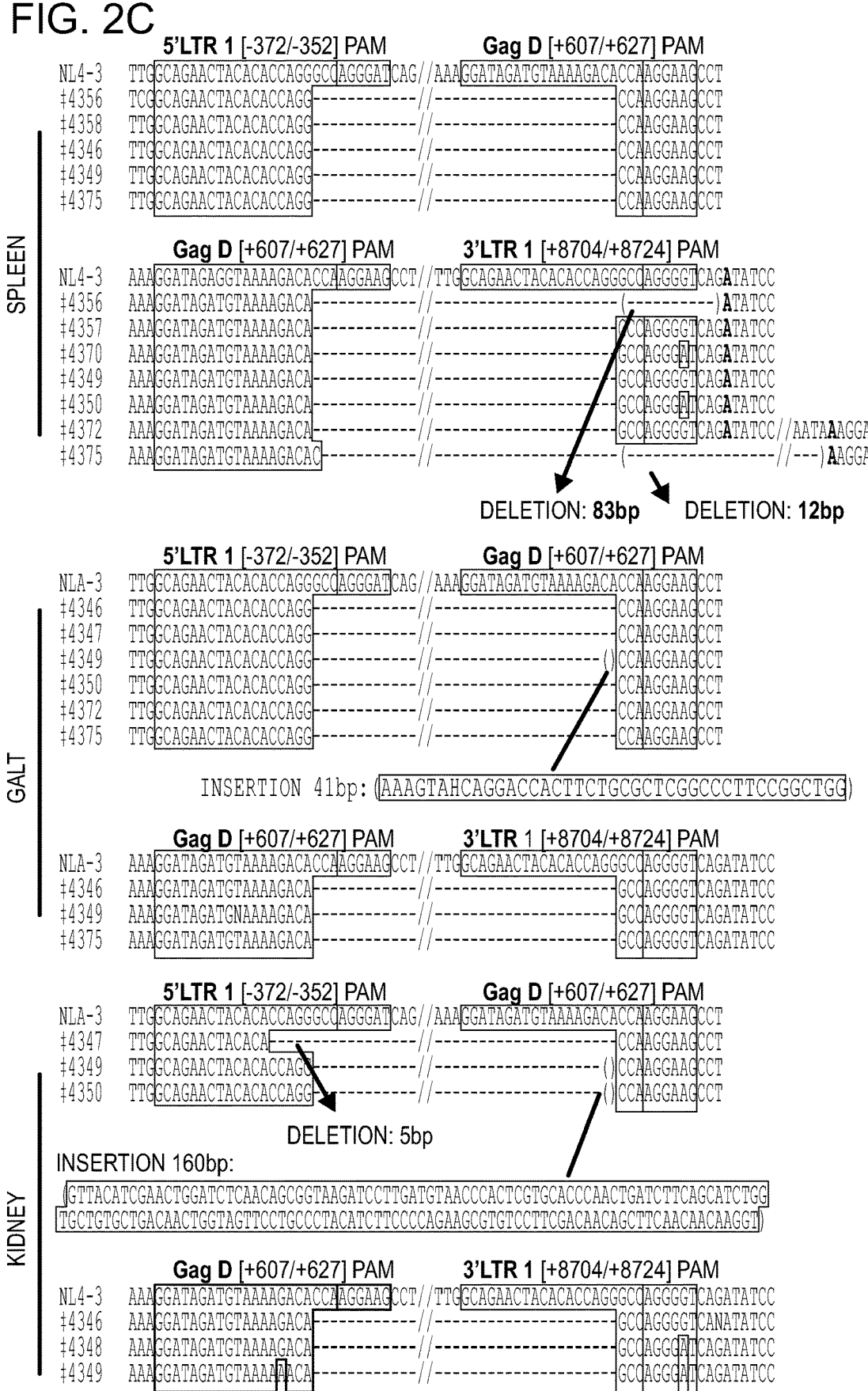

8 nucleotide compositions, and the three possible CRISPR-Cas9 induced break points leading to the excisions of various length of viral DNA fragments. FIG. 2A discloses SEQ ID NOS 155-157, respectively, in order of appearance. FIG. 2B: Total DNA from spleen, GALT, and kidney from three groups of animals were used for PCR genotyping using a set of primers derived from the 5'LTR, 3'LTR, and gag gene in reaction conditions that are calibrated for efficient amplification of short (less than 600 bp) or large DNA fragments. Predicted amplicons of 193 bp and 523 bp, which result from the excisions of DNA fragments between 5' LTR to gag and gag to 3'LTR, respectively, were selected for DNA sequencing. The fragment of 396 bp represents both populations of full length LTRs, as well as the chimeric of both 5' and 3' LTR after excision of entire genome by gRNA LTR1/Cas9 and re-joining of the residual segments of cleaved 5' LTR and 3' LTRs. Several other fragments with closely similar size, caused by InDel mutations, were detected and further analyzed by sequencing. Single asterisks on top of the bands point to the specificity of the fragmental HIV DNA excision by CRISPR-Cas9 as verified by Sanger sequencing (also illustrated in FIGS. 12A-12C and 13A-13M). The double asterisk depicts non-specific amplification of unrelated DNA or randomly amplified segment of truncated HIV-1 sequence (also see FIGS. 14A-14F). FIG. 2C: Representative DNA sequences from each group were aligned to the reference LTR-Gag region of the HIV-1$_{NL4-3}$ sequence. Arrows highlighted positions of small and large deletions. FIG. 2C discloses the Spleen sequences as SEQ ID NOS 158-162, 161-162, 161-162, 161-162, 161, 163-165, 165-166, 165, 167, 165-166, 165, 167, 165-166 and 168, all respectively, in order of appearance. FIG. 2C discloses the Galt sequences as SEQ ID NOS 169-172, 171-172, 171, 173, 171-172, 171-172, 174, 172, 175-179, 178, 177 and 178, all respectively, in order of appearance. FIG. 2C discloses the Kidney sequences as SEQ ID NOS 180-185, 184, 183, 186-189, 188, 190-191 and 190, all respectively, in order of appearance. FIG. 2C discloses the first "Insertion" sequence as SEQ ID NO: 305 and the second "Insertion" sequence as SEQ ID NO: 306.

Figures 3A, 3B:
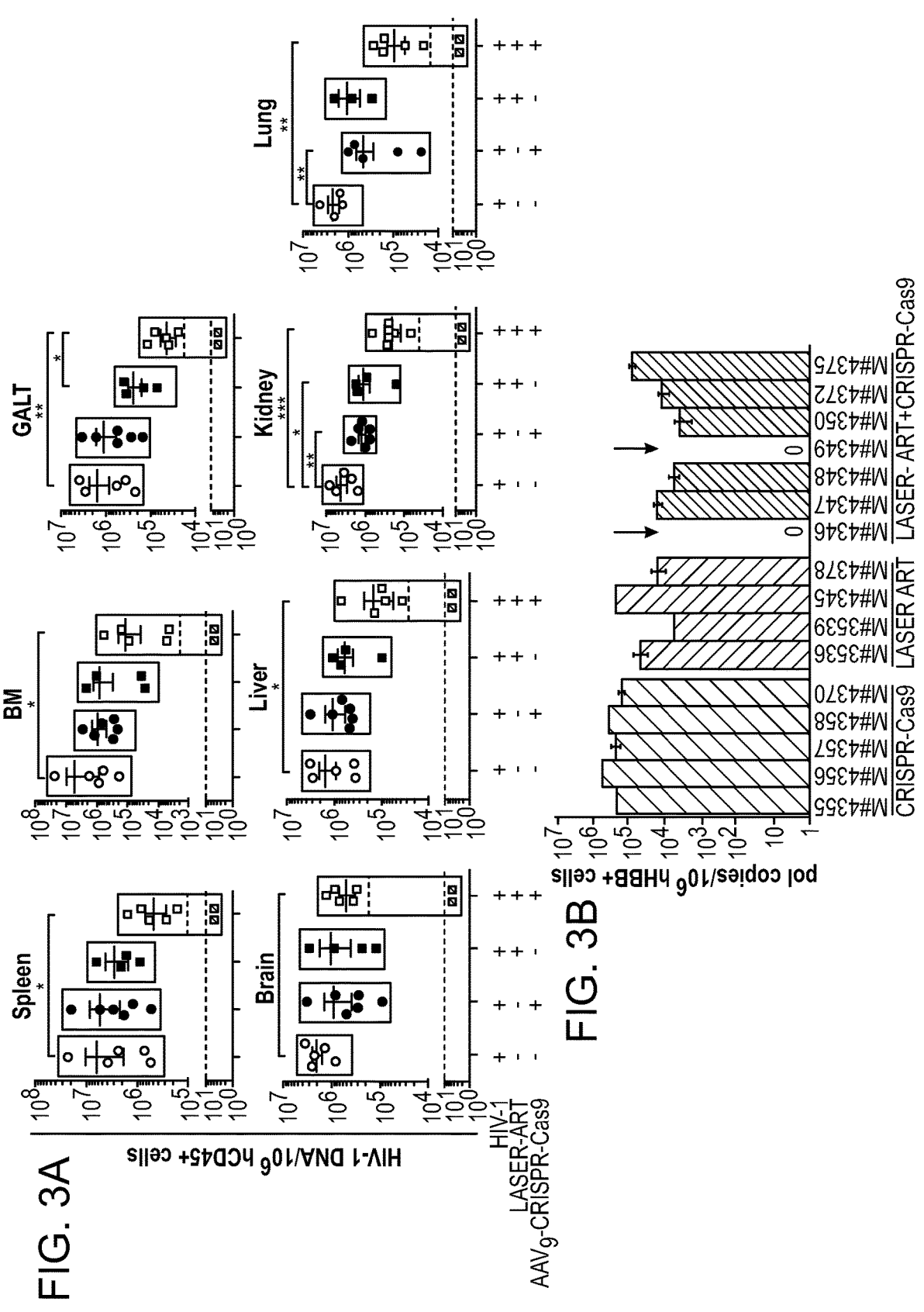
Figures 3C, 3D:
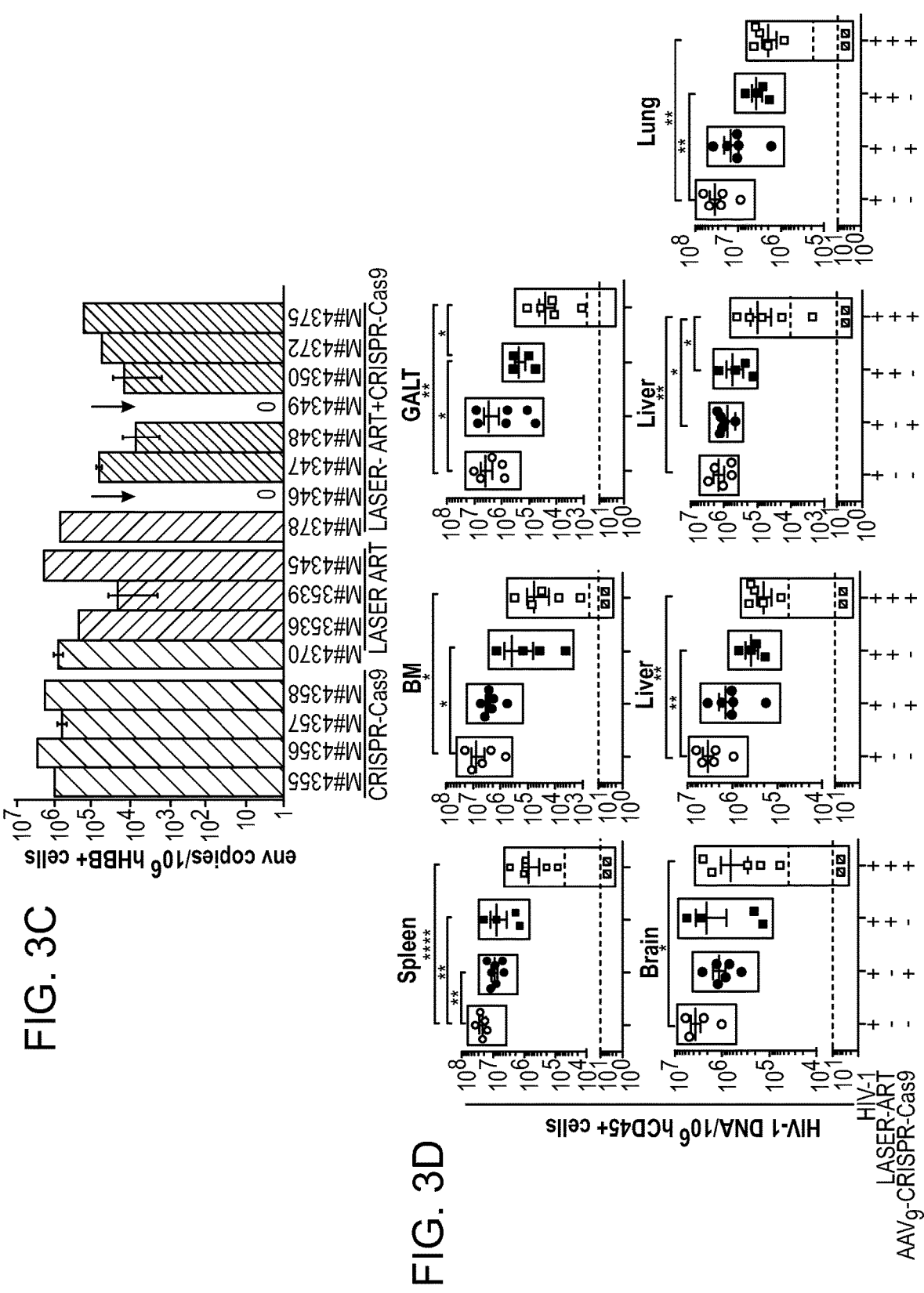
Figure 3E:
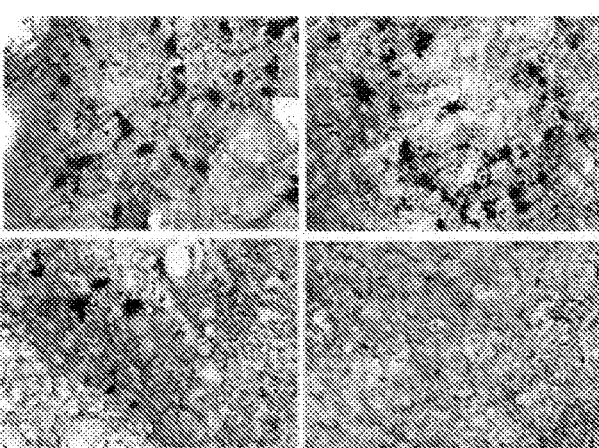

FIGS. 3A-3E show the detection of viral DNA and RNA in various tissues after sequential LASER ART and $AAV_9$-CRISPR-Cas9 treatments of infected humanized mice. (FIG. 3A) HIV-1 DNA and (FIG. 3D) HIV-1 RNA analyses using ultrasensitive semi-nested real-time PCR assays from spleen, bone marrow (BM), GALT, brain, liver, kidney, and lung from treatment groups. The data are expressed as total HIV-1 DNA (FIG. 3A) or HIV-1 RNA (FIG. 3D) copies/$10^6$ human $CD45^+$ cells. Two animals, #4346 and #4349 [shown by the squares below the dashed lines (detection limit)], with dual treatments, showed sterilization of virus from all tissues analyzed. FIGS. 3B and 3C: Quantitative PCR showed complete elimination of signals corresponding to pol (FIG. 3B) and env (FIG. 3C) DNA sequences of HIV-1 in mice #4346 and #4349 (shown by arrows). FIG. 3E: Representative results from RNAscope assay revealed the detection of single or clusters of brown dots corresponding to HIV-1 RNA in 5 pm-thick spleen sections of infected animals receiving either LASER ART or CRISPR-Cas9, but not both (#4346). E1 are representative spleen sections obtained from humanized mice infected with HIV-1 (controls); E2 are HIV-1 infected animals treated only with CRISPR-Cas9; E3 are HIV-1 infected LASER ART treated animals demonstrating viral rebound after cessation of therapy, and E4 are infected animals treated first with LASER ART followed by CRISPR-Cas9. E1-E4 are representative tissue sections taken from each of the animal groups. In these assays, we used the antisense V-HIV1-Clade-B targeting 854-8291 base pairs of HIV-1 as the probe. Human peptidylprolyl isomerase B (PPIB) was used as a positive control for all tissues analyzed. Images are 40× magnification. A one-way ANOVA and Bonferroni's post-hoc tests for multiple comparisons and a two-tailed Student's t-test was used for comparisons between two groups as in FIGS. 3A and 3D for statistical analyses. *P<0.05, P<0.01, *P<0.001.

Figure 4A:
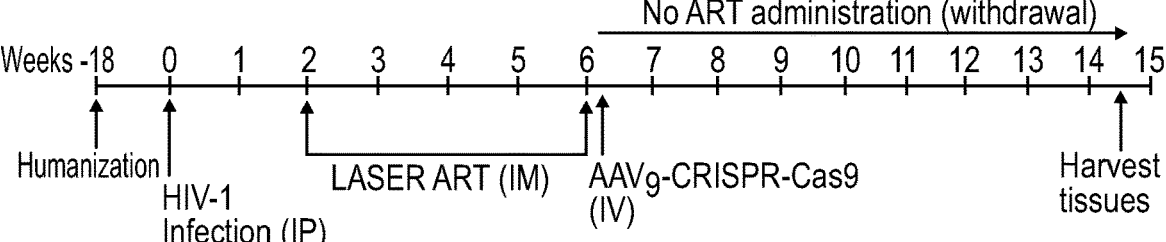
Figure 4B:
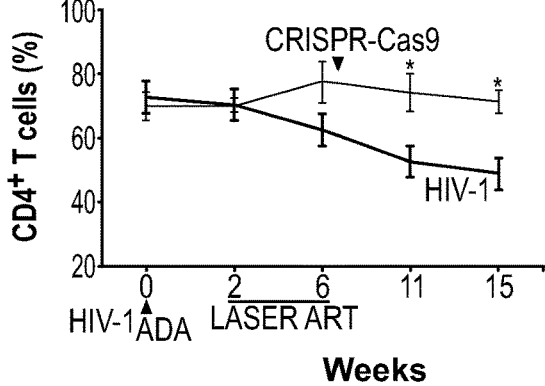
Figure 4C:
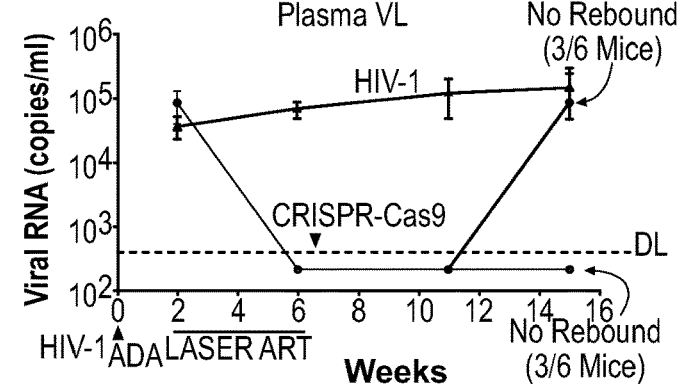
Figure 4D:
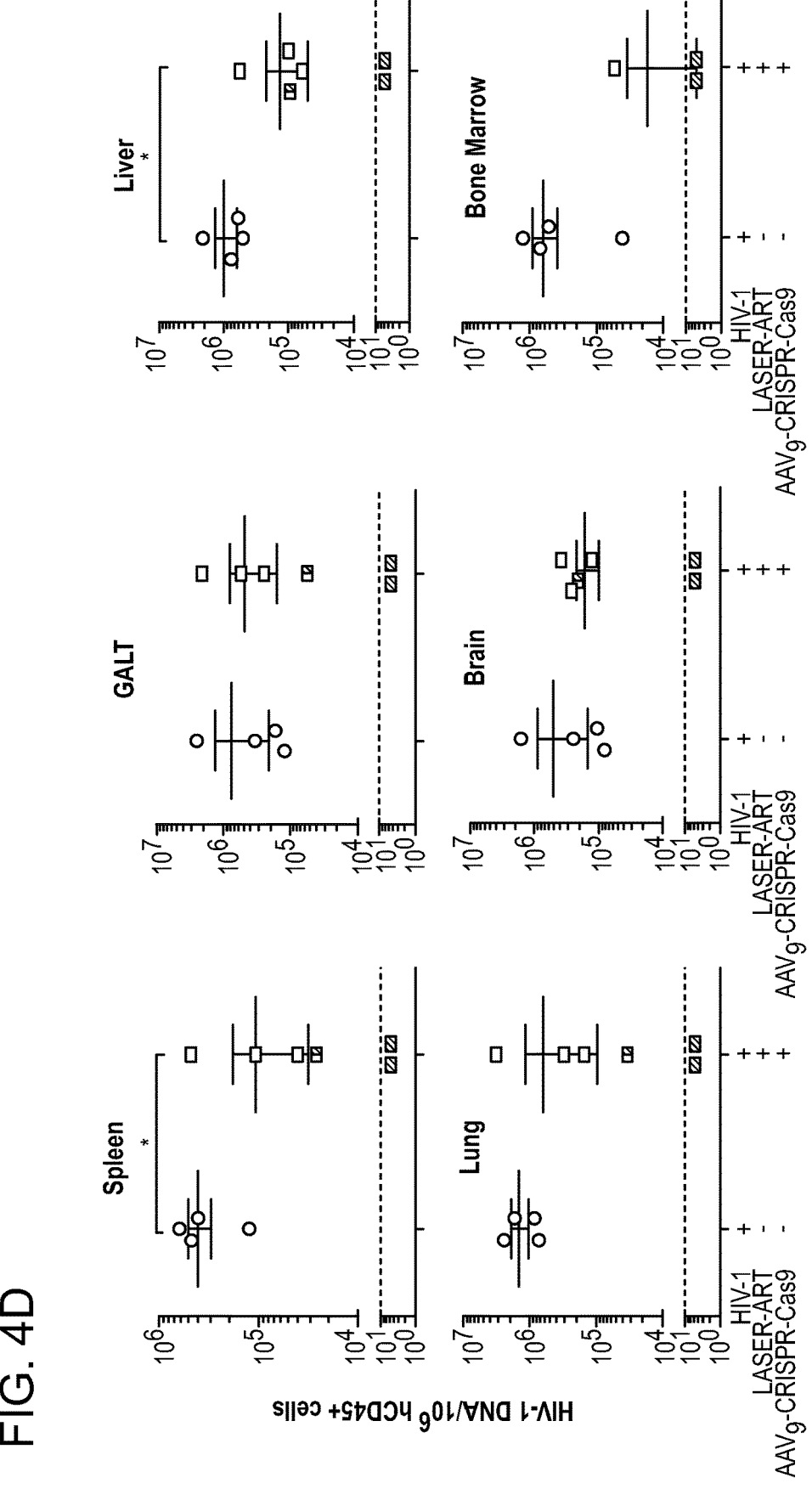

FIGS. 4A-4G show the viral sterilization in HIV-1ADA infected humanized mice in LASER ART and CRISPR-Cas9 (dual treated) by measures of viral, immune profile and excision profiles. FIG. 4A: The timeline of the experiment showing the temporal administration of LASER ART and CRISPR-Cas9 treatments, and animal sacrifice. FIG. 4B: The percentage of human CD4$^+$ T-cells and (FIG. 4C) viral loads measured in the HIV-1 infected and HIV-1 infected and dual treated animal groups. Dual treated animals that showed no or viral rebound are illustrated. FIG. 4D: HIV-1 DNA analysis was performed using ultrasensitive semi-nested real-time q-PCR assays from spleen, GALT, liver, lung, brain and bone marrow from infected and infected and dual treated mice. The data are expressed as total HIV-1 DNA copies/$10^6$ human CD45$^+$ cells. Two animals, #3319 and #3336 (illustrated by the squares) were below the dashed lines for virus detection as measured by plasma VL. These animals had no detectable viral DNA after dual treatments demonstrating viral sterilization from all analyzed tissues. A single animal (#3324) is illustrated by a half-red-black designation that had an undetectable VL but viral DNA was observed. FIG. 4E: Ultrasensitive ddPCR, with sensitivity of detecting 1-2 viral copies, was used in cross validation tests for viral DNA detections and performed in all tissues of infected and infected/dual treated animals. As a positive control, one animal each from the HIV-1 infected and HIV-1 and LASER ART groups are illustrated as open structures together. These were placed together with the six infected animals from the dual treatment group illustrated as closed structures. Dashed line represents the limit of detection. FIG. 4F: Agarose gel analyses of the PCR assay of DNA from various tissues of two animals with no rebound shows the presence of segments of HIV-1 LTR DNA and detection of a 121 bp amplicon, indicative of excision of a DNA fragment between the LTR and the gag gene (top). The histogram illustrates representative results from sequencing of the 121 bp fragment highlighting the position of the 5' LTR breakpoint, and Gag and PAM trinucleotide on the GagD RNA. FIG. 4F discloses SEQ ID NO: 192. FIG. 4G: Splenocytes and bone marrow cells were isolated from HIV-1 infected mice with or without prior LASER ART and/or CRISPR-Cas9 treatments. These cells were then used in adoptive transfers performed in uninfected and drug naïve mice. These transfer experiments performed in CD34$^+$ HSC humanized mice were used to examine potential rebound from latent reservoirs not detected by standard ddPCR and nested PCR tests. In addition, as positive controls, two animals from an HIV-1 infected group and one from the LASER ART "alone" treatment group are shown as open circles and boxes. Five animals from the dual treatment group are illustrated as closed circles and boxes. Mice were sacrificed after 30 days and analyzed for plasma viral RNA using the Roche Ampliprep/Taqman-48 V2.0 detection assay. Virus was not detected in 2 "dual-treated" animals (#3319 and #3336, circles and boxes below the dotted line for the cutoffs for viral detection) in all tests. This was used as the definition of "viral eradication" in these experiments. In contrast, virus was readily identified in all other infected and treated groups. A one-way ANOVA and Bonferroni's post-hoc tests for multiple comparisons and a two-tailed Student's t-test was used for comparisons between two groups as in FIGS. 4B and 4D for statistical analyses. *P<0.05.

Figures 5F, 6A:
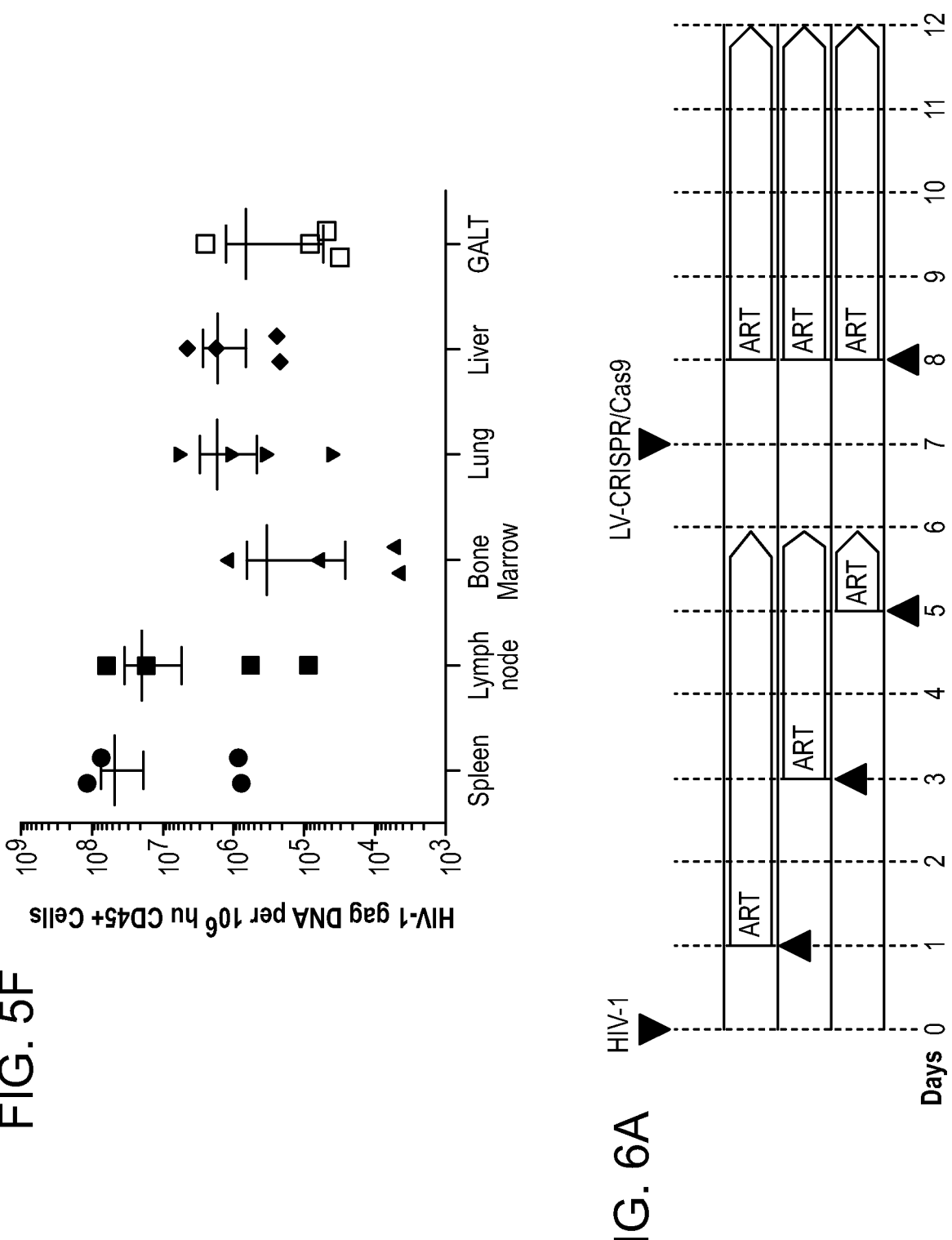

FIGS. 5A-5F show the results from a study of viral and CD4$^+$ T cell profiles from simultaneously treated HIV-1 infected Hu-PBL mice with LASER ART and AAV$_9$-CRISPR-Cas9. FIG. 5A: Study scheme illustrates time of human cells reconstitution, HIV-1 infection, LASER ART administration, AAV$_9$-CRISPR-Cas9 injection (50 μl of 2×$10^{13}$ GC/ml), and time of sacrifice and flow cytometric evaluation of pan-human CD4$^+$ T cells. FIG. 5B: Peripheral blood cells were assayed prior to and after (day 14) HIV-1 infection. FIG. 5C: Plasma viral load was detected using Roche ampliprep V2.0/Taqman 48 system from different mice groups. FIG. 5D: The DNA analysis from gag region from spleen tissues showed reduced HIV-1 in LASER ART alone which were further decreased in LASER ART plus AAV$_9$-CRISPR-Cas9 treated groups as compared to HIV-infected but untreated controls and the AAV$_9$-CRISPR-Cas9 group. FIG. 5E: HIV-1 RNA was analyzed using highly sensitive semi-nested real-time PCR assays from spleen samples of all four groups of mice at the end of the study (day-14 after infection). Significant decreases in HIV-1 RNA in LASER ART alone and LASER ART plus AAV$_9$-CRISPR-Cas9 treated groups compared to HIV-1 infected but untreated controls were observed. The data are expressed as the ratio of total HIV-1 RNA copies/$10^6$ human CD45$^+$ cells. FIG. 5F: Quantitative PCR of viral RNA from 14 days HIV-1 infected humanized mice. HIV-1 RNA was analyzed using ultrasensitive semi-nested real-time PCR assays from spleen, lymph node, bone marrow, lung, liver, and GALT obtained from HIV-1 infected humanized mice at day 14.

Figures 6B, 6C:
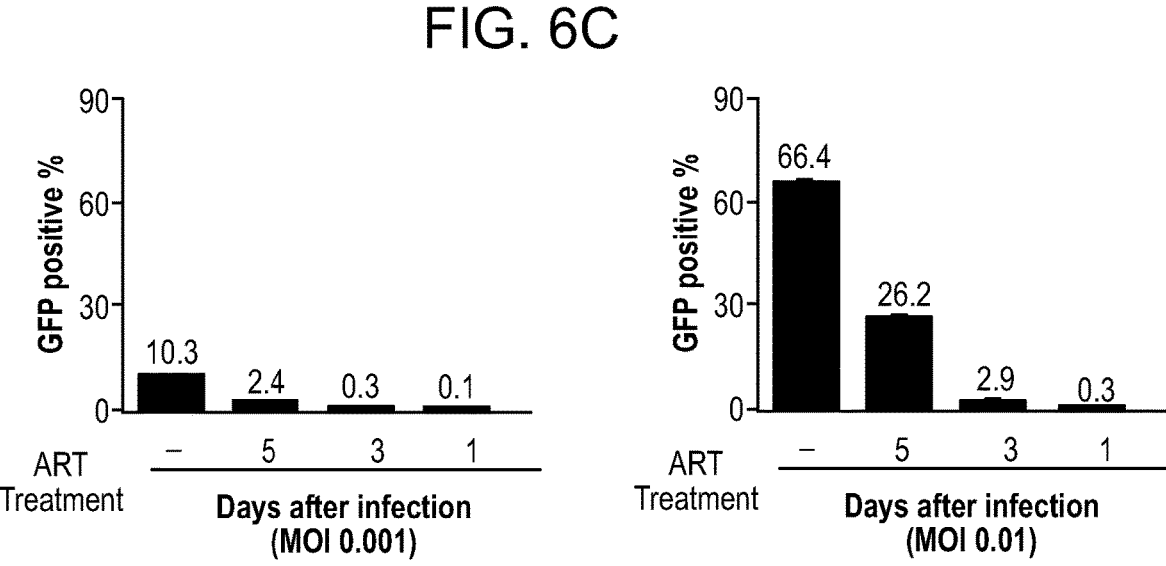

FIGS. 6A-6C show the combined effect of ART and CRISPR/Cas9 on HIV-1 infection of Jurkat T cell line. FIG. 6A: Experimental design and procedure. Jurkat cells were infected with HIV-1NL$_{4-3}$-GFP-P2A-Nef at multiplicity of infection (MOI) 0.001 and 0.01. Next, cells were divided into four groups: one control, DMSO treated and three treated with the cocktail composed of four antiretroviral drugs (ART) at the concentrations of 5×EC$_{90}$ values (dolutegravir (DTG) 11.1 ng/ml, rilpivirine (RPV) 3.3 ng/ml, lamivudine (3TC) 17.2 μg/ml and abacavir (ABC) 8.3 μg/ml. Second set of experiments was performed using myristoylated, precursor antiretroviral drugs (LASER ART) similarly, at the doses 5×EC90 values (myristoylated dolutegravir (MDTG) 16.7 ng/ml, rilpivirine (RPV) 3.3 ng/ml, myristoylated lamivudine (M3TC) 32.9 μg/ml and myristoylated abacavir (MABC) 14.4 μg/ml). ART/LASER ART treatment was started at day 1, 3 or 5 after infection and fresh drugs were added daily. At day 6 of infection the drugs were removed to allow efficient lentiviral transduction of Cas9 and gRNAs LTR A and LTR B which was conducted at day 7. At day 8 antiretrovirals were added back and continued for another 4 days. Twelve days after HIV-1 infection cells were collected, genomic DNA was extracted and analyzed by PCR for CRISPR-Cas9 mediated cleavage of viral LTR sequences. FIG. 6B: Quantification of the level of infection at day 7. Cells were fixed with 2% PFA and FACS analysis was performed to measure GFP expressing population for HIV infection/replication in vitro. FIG. 6C: Similar to FIG. 6B with exception that cells were treated with modified ART.

Figures 7A, 7B:
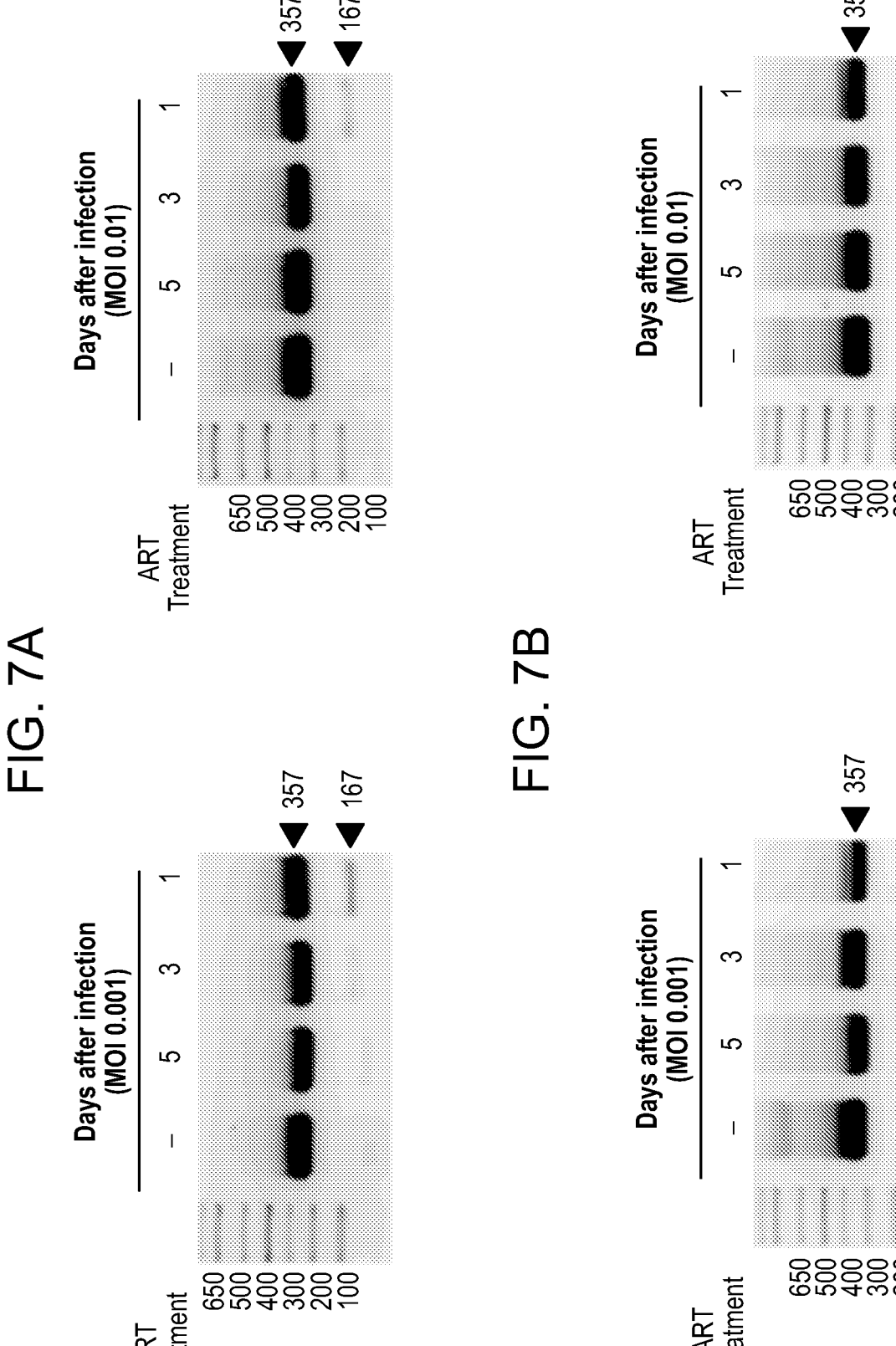
Figures 7C, 7D:
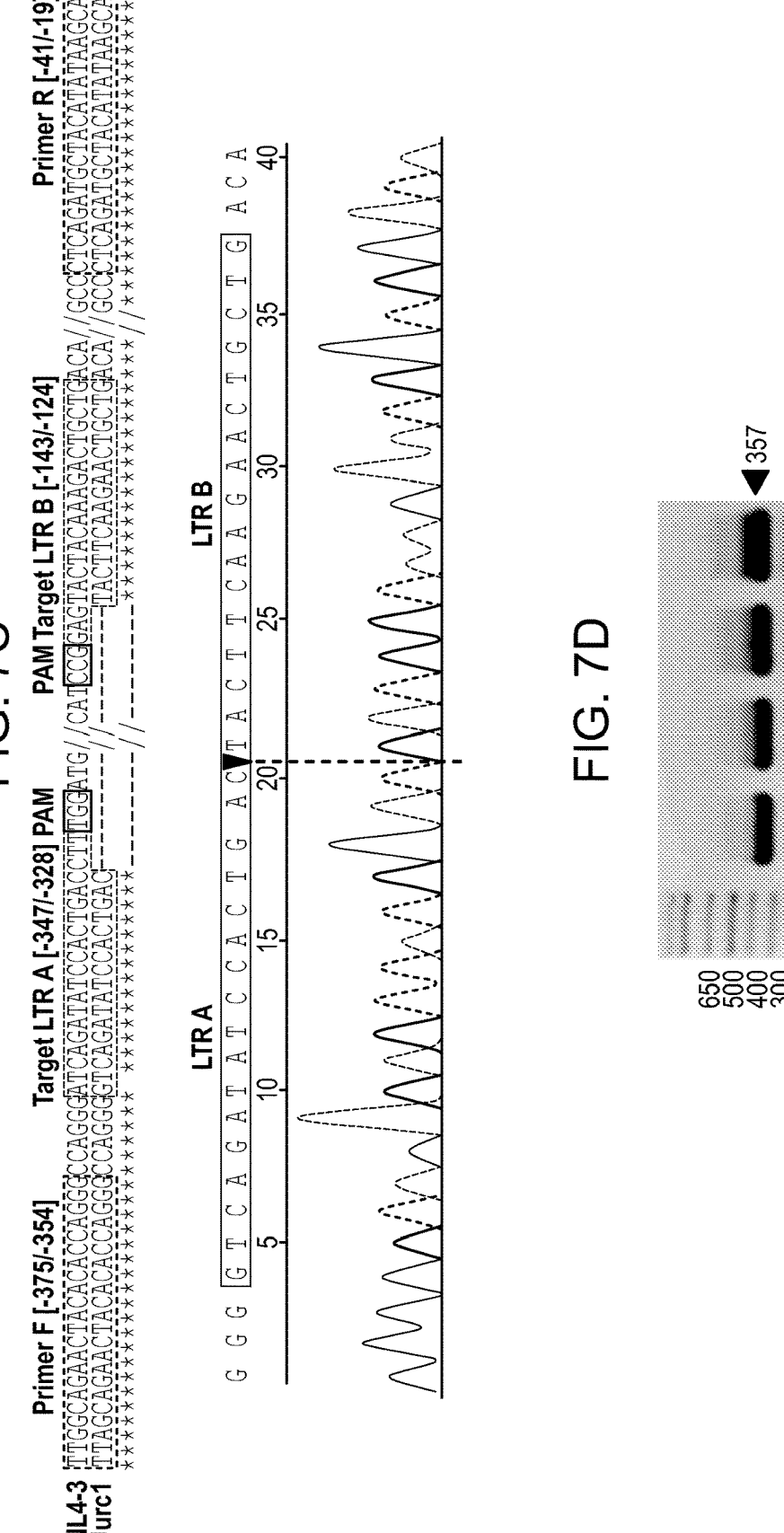
Figure 7E:
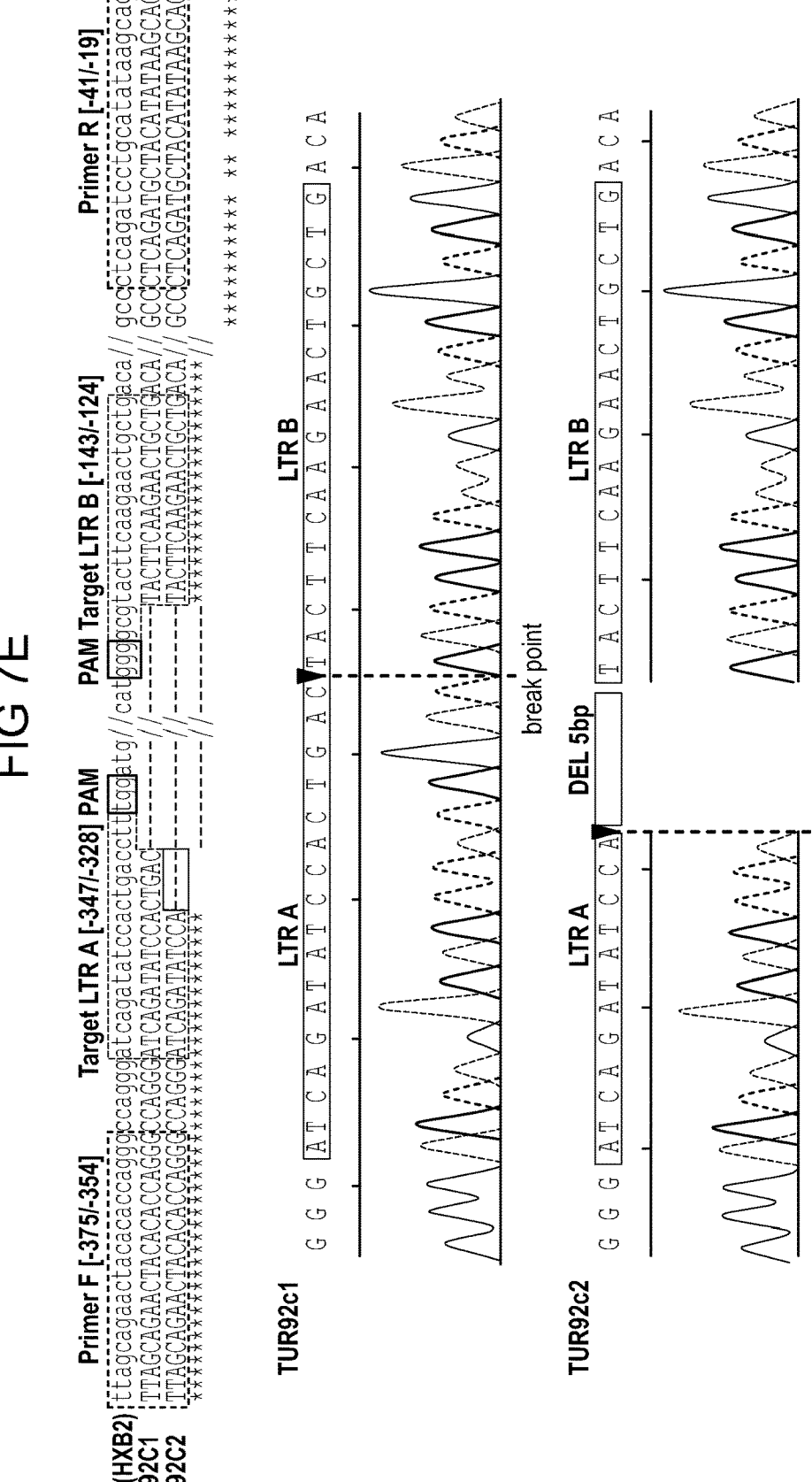

FIGS. 7A-7E show the excision of HIV DNA fragment by CRISPR-Cas9 in ART treated T cells and Patient driven PBMCs. Results from standard PCRs of genomic DNA obtained from infected and treated T cells. The presence of full length LTR (357 bp) and truncated, CRISPR-Cas9 induced products (167 bp) was examined (FIGS. 7A and 7B) and aligned to HIV genome after Sanger sequencing. FIG. 7C: Results of the truncated PCR product obtained after purification from the agarose gel and TA cloning. Below, a representative example of Sanger sequence tracing of truncated product. The HIV-1 LTR sequence was cleaved by Cas9 at target sites LTR A and LTR B and then joined together, resulting in deletion of 190 bp proviral DNA segment. The double cleaved/end-joined site is shown as a breaking point. FIG. 7C discloses SEQ ID NOS 193-197, 195 and 198, respectively, in order of appearance. FIG. 7D: PCR results of genomic DNA from PBMC's obtained from HIV positive individual. The presence of full length LTR (357 bp) and truncated, CRISPR-Cas9 induced products (167 bp) was examined. The cells were pretreated with ART for 5 (line 4.), 3 (line 3.) or 1 day (line 2.) or control, DMSO treated (line 1.). At day 6 drugs were removed and next day Cas9 and gRNAs were delivered by lentiviral transduction. At day-8 ART was resumed for another 4 days when cells were collected and processed same way like Jurkat cells above. FIG. 7E: Alignment of a representative Sanger sequencing results of the truncated PCR products obtained after purification from the agarose gel and TA cloning. Below a representative examples of Sanger sequence tracing of truncated products. The HIV-1 LTR sequence was cleaved by Cas9 at target sites LTR A and LTR B and then joined together, resulting in deletion of 190 bp proviral DNA segment. The double cleaved/end-joined site is shown as a breaking point. In the case of second clone a short: 5 bp deletion was detected at the cut site. FIG. 7E discloses SEQ ID NOS 199-205, 203-204 and 206-208, respectively, in order of appearance.

FIGS. 8A, 8B are flow cytometric evaluations of human leukocyte reconstitution in humanized mice. Peripheral blood of human stem cell reconstituted mice was assayed before and after (weeks 2, 6, 9, and 14) HIV-1 infection for the presence of human CD45$^+$ (FIG. 8A) and CD3$^+$ (FIG. 8B) cells. These experiments were performed to assess levels of humanization throughout the study. Numbers of human CD45$^+$ and CD3$^+$ cells were consistent within all the treated groups. These included animals not treated, treated with LASER ART or CRISPR-Cas9 alone or in combinations of LASER ART and CRISPR-Cas9. Notably, in the HIV-1 infected mice group, the numbers of CD45$^+$ and CD3$^+$ human cells in blood of mice were comparable to each of the treatment groups.

FIG. 9 shows the immunohistology of spleens from HIV-1 infected humanized mice. These mice were administered LASER ART or were left untreated. Animals were sacrificed at the time of CRISPR-Cas9 treatment to determine the presence of human CD4$^+$ viral target T cells. Representative images are shown from mice infected with HIV-1NL$_{4-3}$ with or without LASER ART. Significant reductions in CD4$^+$ T cells numbers (brown stained cells) are readily seen in the HIV-1-infected group compared to HIV-1 infected animals treated with LASER ART. Duplicate treatments groups demonstrate adequacy or randomization for CRISPR-Cas9 therapy.

Figures 10, 11:
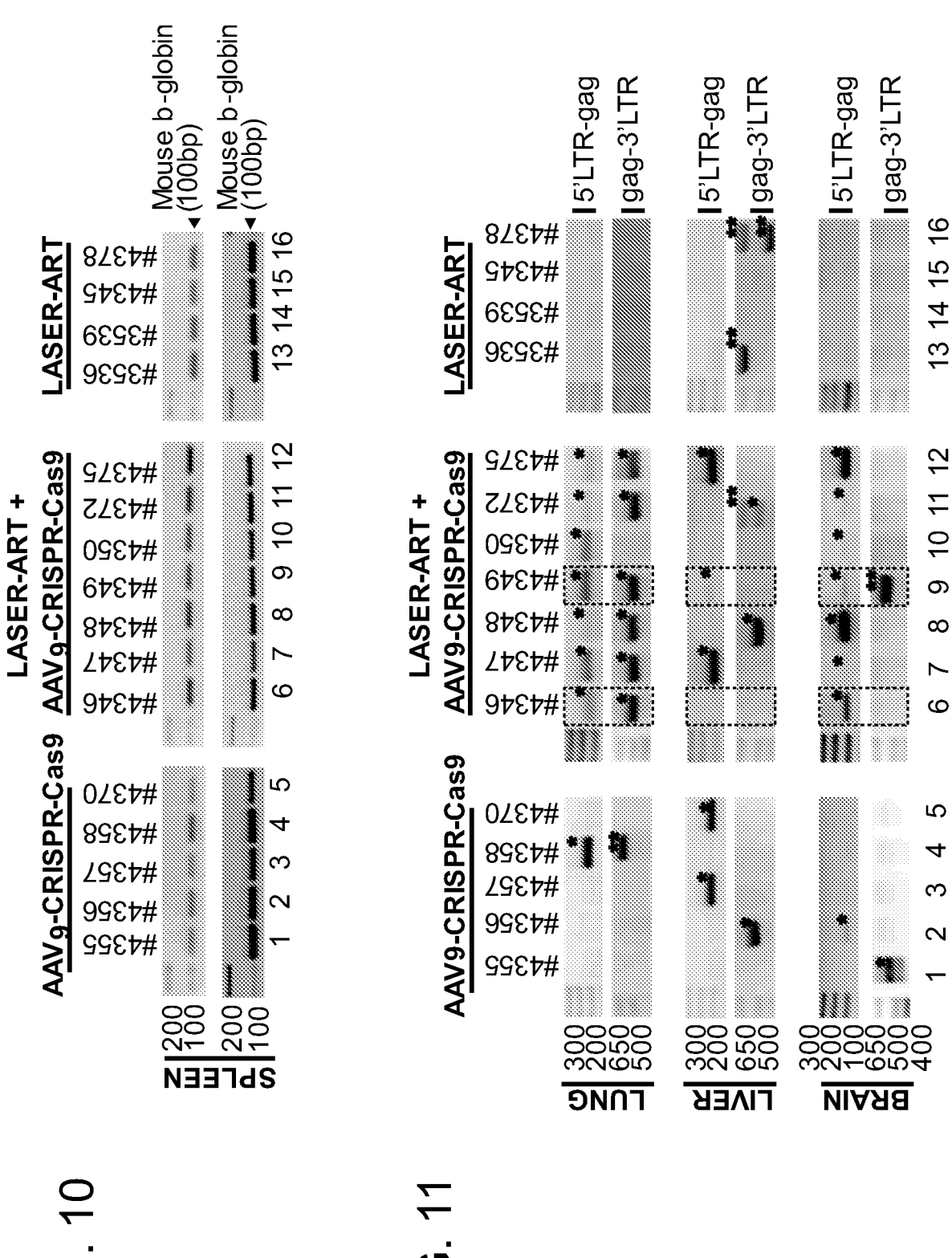

FIG. 10 shows the verification of the presence of human cells in the spleens of humanized mice. PCR analysis of genomic DNA isolated from the spleens of humanized animals using primer sets specific to human and mouse (for a control) beta-globin genes.

FIG. 11 shows the excision of the viral DNA fragments by CRISPR-Cas9 in tissues from HIV-1 infected humanized mice with and without treatments with LASER ART. Results from standard PCRs of genomic DNA obtained from lungs, livers and brains of treated animals. The presence of full length LTR (396 bp) and truncated, CRISPR-Cas9 induced products (193 bp for 5'LTR-gag and 523 bp for gag-3'LTR) were tested. * CRISPR-Cas9 mediated excision products. ** Non-related.

FIGS. 12A-12C show the Sanger sequencing results of the truncated, CRISPR-Cas9 excised HIV-1 genomes. FIG. 12A: Representative examples of canonical, InDel free, CRISPR-Cas9 induced, double cleaved/end-joined HIV-1 genome truncations observed in majority of the tissues of AAV$_9$-CRISPR-Cas9/gRNA treated animals. On the left, result obtained from the spleen of mouse #4356 using 5'LTR-gag specific primers and on the right sequence from the spleen of mouse #4375 using gag-3'LTR specific amplification. FIG. 12A discloses SEQ ID NOS 209-210, respectively, in order of appearance. FIG. 12B: Verification of the presence of 41 bp insertion at the CRISPR-Cas9 mediated cleavage site in the viral sequence observed in GALT sample from mouse #4349. FIG. 12B discloses SEQ ID NO: 211. FIG. 12C: Sequence of the longer, 160 bp insertion found at the Cas9 cleavage site in the kidney sample from the same mouse #4349. FIG. 12C discloses SEQ ID NO: 212.

Figure 13A:
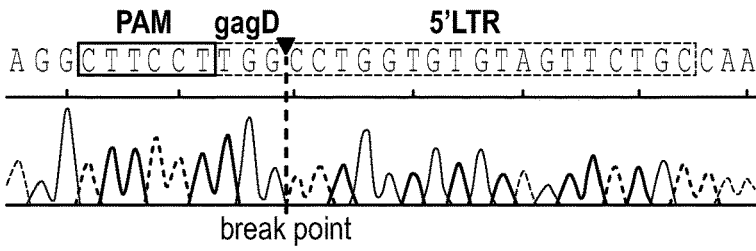
Figure 13B:
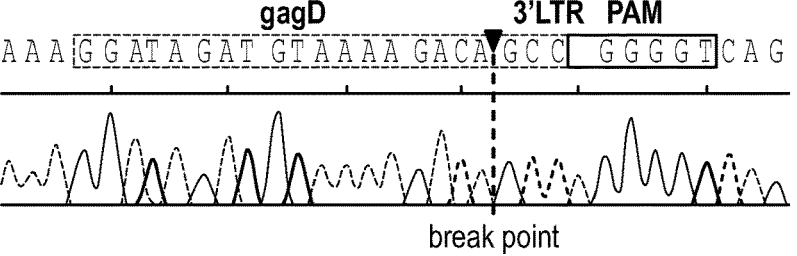
Figure 13C:
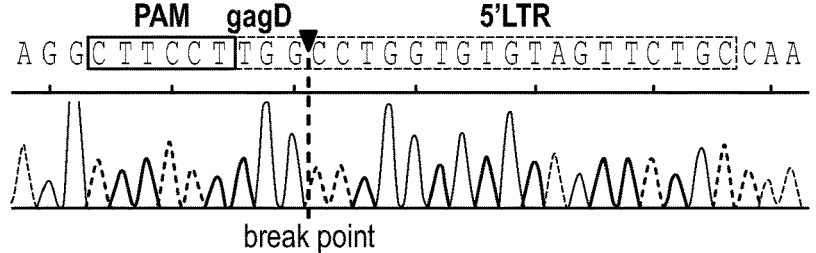
Figure 13D:
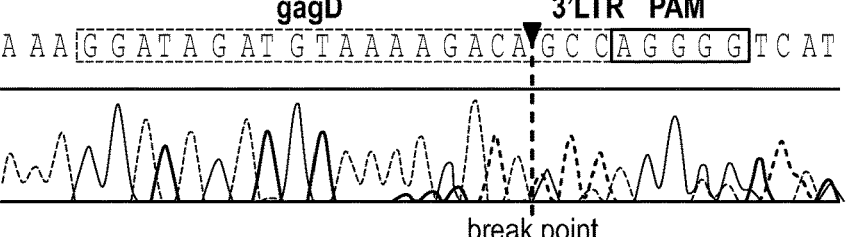
Figure 13E:
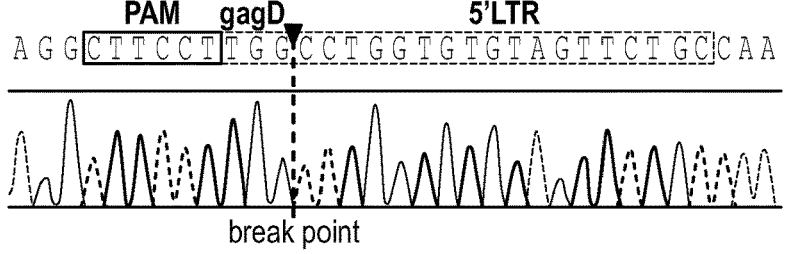
Figure 13F:
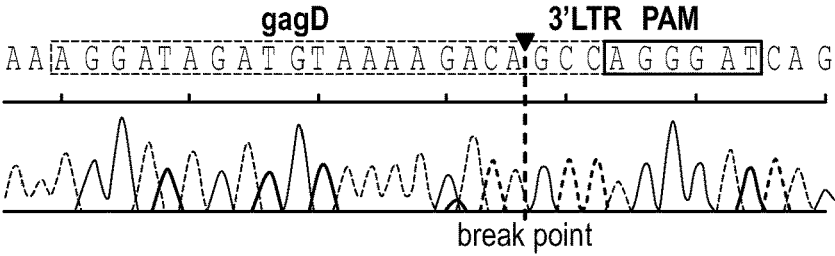
Figure 13G:
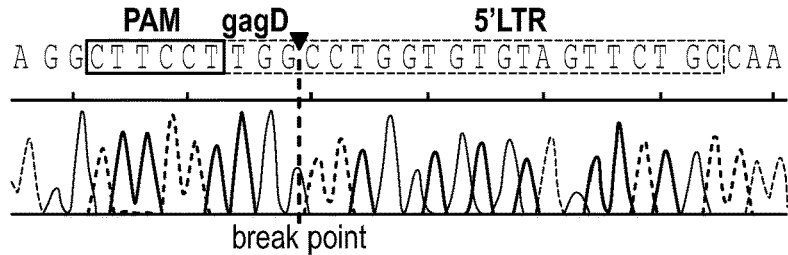
Figure 13H:
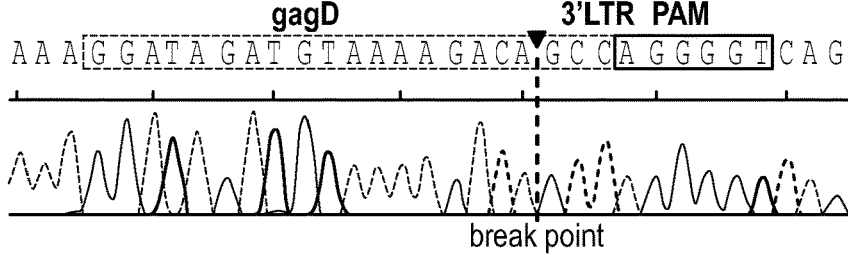
Figure 13I:
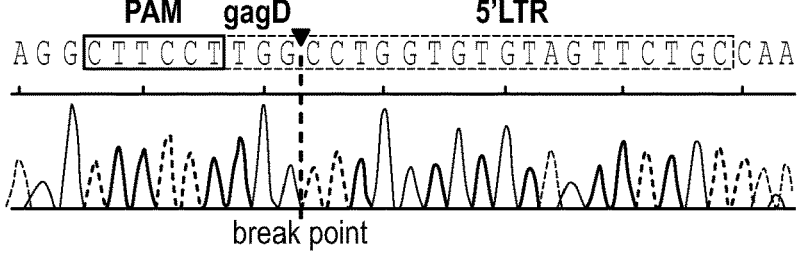
Figure 13J:
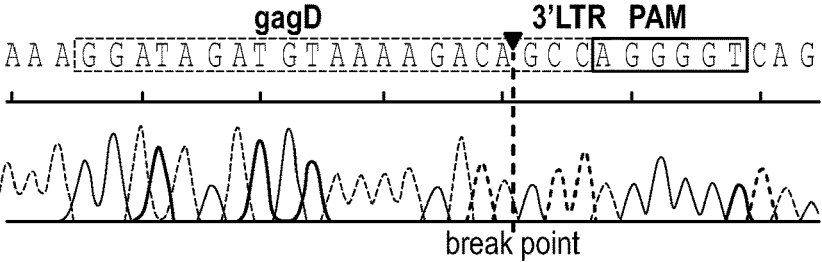
Figure 13K:
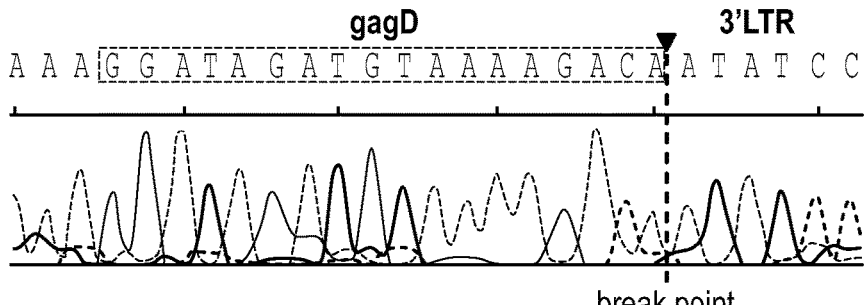
Figure 13L:
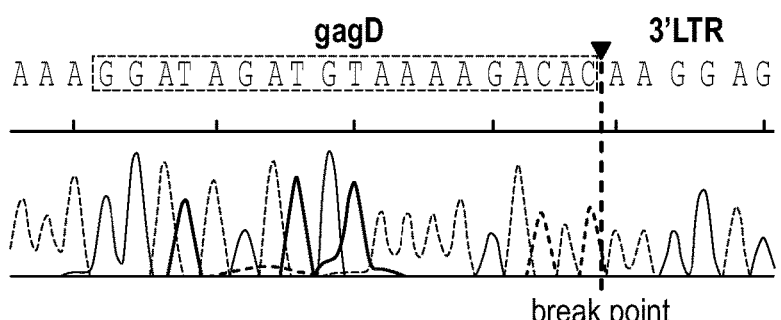
Figure 13M:
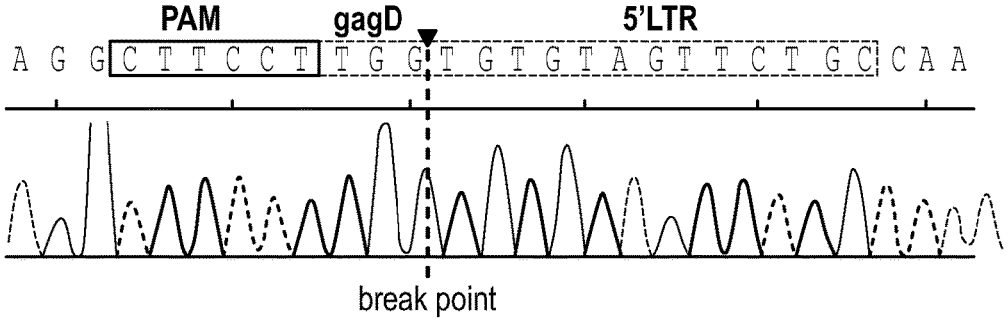

FIGS. 13A-13M show the Sanger sequencing tracing results of the truncated, CRISPR-Cas9 excised HIV-1 genomes. Representative examples of canonical, InDel free, CRISPR-Cas9 induced, double cleaved/end-joined HIV-1 genome truncations observed in majority of the tissues of AAV$_9$-Cas9/gRNA treated animals (FIGS. 13A (SEQ ID NO: 213), 13B (SEQ ID NO: 214): GALT; FIGS. 13C (SEQ ID NO: 215), 13 D (SEQ ID NO: 216): Kidney; FIGS. 13E (SEQ ID NO: 217), 13F (SEQ ID NO: 218): Lung; FIGS. 13G (SEQ ID NO: 219), 13H (SEQ ID NO: 220): Liver and FIGS. 13I (SEQ ID NO: 221), 13J (SEQ ID NO: 222): Brain). InDel mutation detected at the cleavage/end-joining sites in several tissues are shown in FIGS. 13K (SEQ ID NO: 223), 13L (SEQ ID NO: 224) for spleen, FIG. 13M (SEQ ID NO: 225) for kidney.

FIGS. 14A-14F show Sanger sequencing results of a few, non-related to CRISPR-Cas9, truncated HIV-1 amplicons detected in some of the samples. Sequences were aligned to HIV-1NL$_{4-3}$ sequence as a reference. The sequencing data revealed lack of CRISPR-Cas9 specific cleavage (3 nucleotides from PAM) at the target sites LTR 1 (5'LTR in FIG. 14A for spleen lane 3 and 7, 3'LTR for kidney in FIG. 14C, lane 11, in FIG. 14D for lung lane 4 and FIG. 14F for brain, lane 9) or GagD (in FIG. 14C for kidney lane 7 and in FIG. 14E for liver lanes 2 and 16). Partial 3'LTR sequence was obtained for spleen lane 16 (FIG. 14B). FIG. 14A discloses the NL4-3 sequences as SEQ ID NOS 226 and 229, the Lane 3 sequences as SEQ ID NOS 227 and 230, and the Lane 7 sequences as SEQ ID NOS 228 and 231, all respectively, in order of appearance. FIG. 14B discloses the NL4-3 sequences as SEQ ID NOS 232-233 and the Lane 16 sequence as SEQ ID NO: 234, all respectively, in order of appearance. FIG. 14C discloses the NL4-3 sequences as SEQ ID NOS 235-237 and 240-241, the Lane 7 sequences as SEQ ID NOS 236 and 238, and the Lane 11 sequences as SEQ ID NOS 239-240 and 242, all respectively, in order of appearance. FIG. 14D discloses the NL4-3 sequence and the Lane 4 sequence as SEQ ID NOS 243-244, all respectively, in order of appearance. FIG. 14E discloses the NL4-3 sequences as SEQ ID NOS 245-248 and 254-256, the Lane 2 sequences as SEQ ID NOS 249 and 257, the Lane 16 top sequences as SEQ ID NOS 250, 247, 251 and 258, and the Lane 16 bottom sequences as SEQ ID NOS 252-253, 259 and 256, all respectively, in order of appearance. FIG. 14F discloses the NL4-3 sequences as SEQ ID NOS 260-263 ad 265 and the Lane 9 sequences as SEQ ID NOS 264 and 266, all respectively, in order of appearance.

Figure 15:
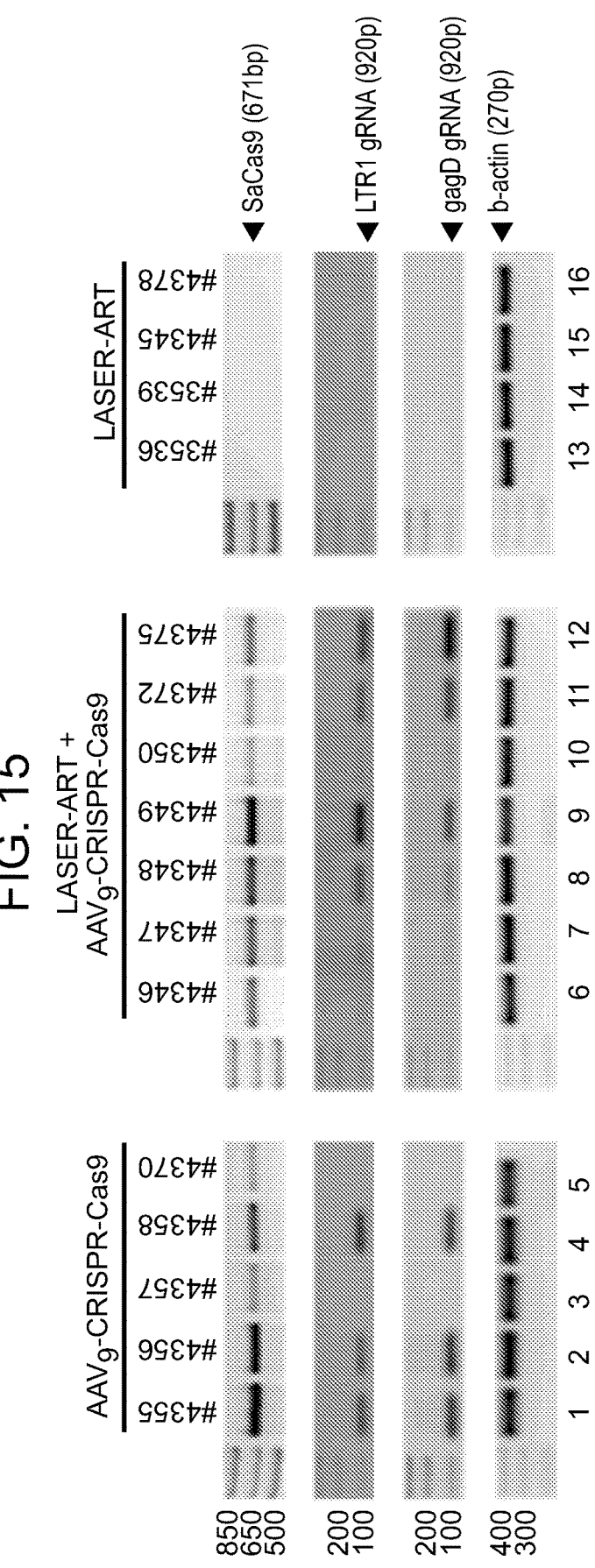

FIG. 15 shows the Cas9/gRNAs expression in the spleens of treated animals. Reverse transcription-PCR analysis of RNA extracted from spleens of treated animals to represent SaCas9 mRNA (top panels), single guide RNAs: LTR 1 (second row panels) and Gag D (third row panels) and a control beta-actin mRNA (bottom panels) were detected using primer sets specific to each target.

Figure 16A:
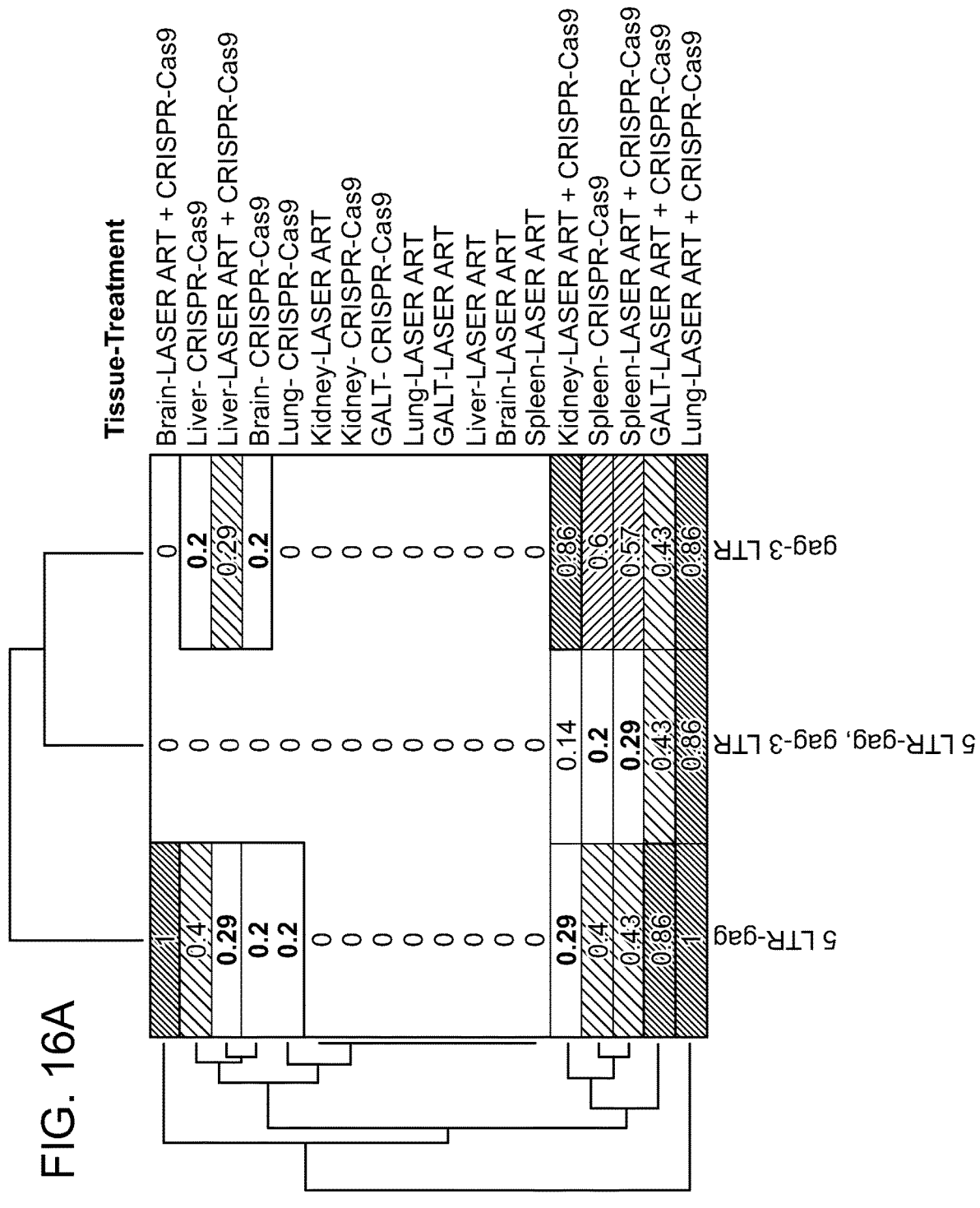
Figure 16B:
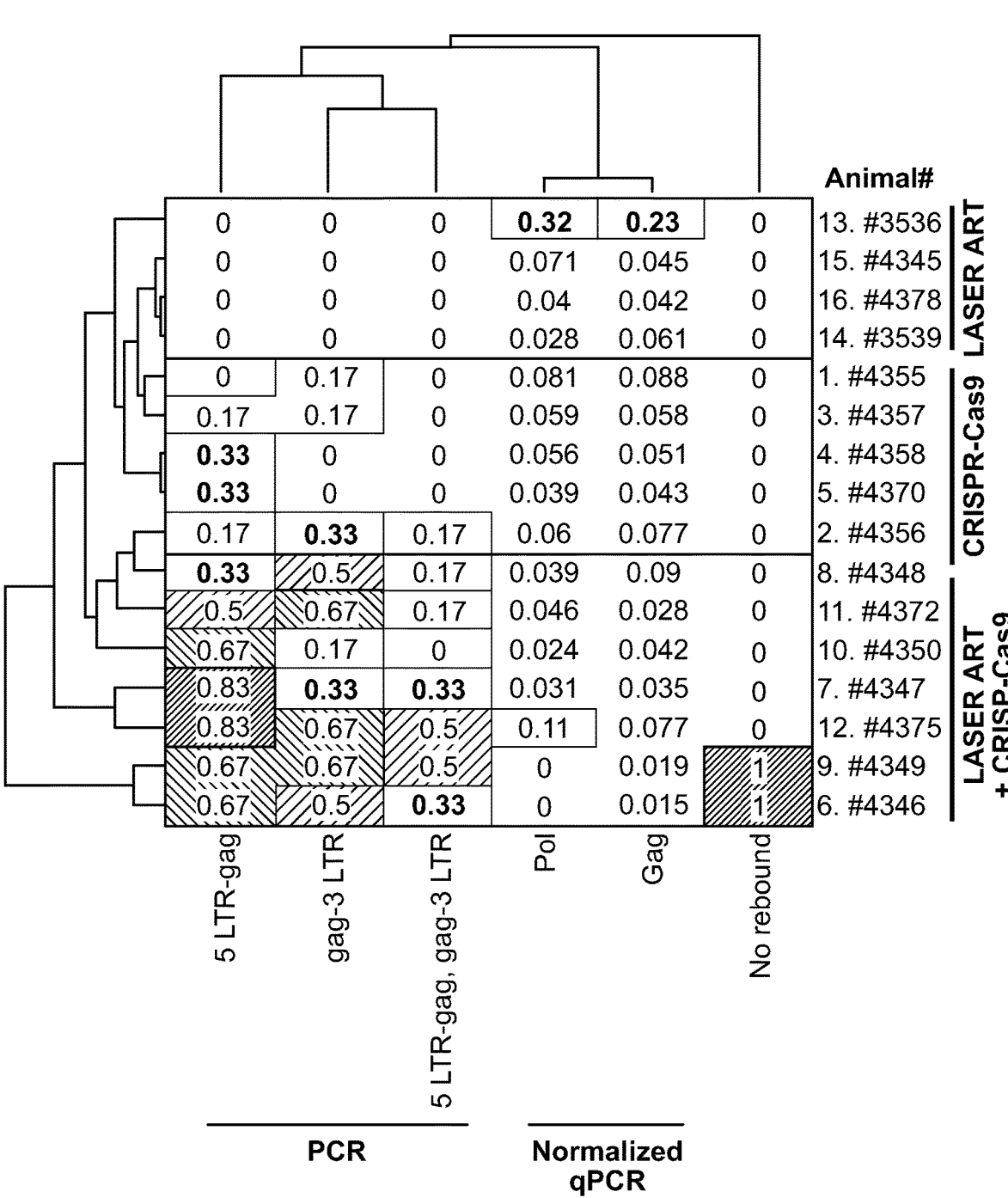
Figure 16C:
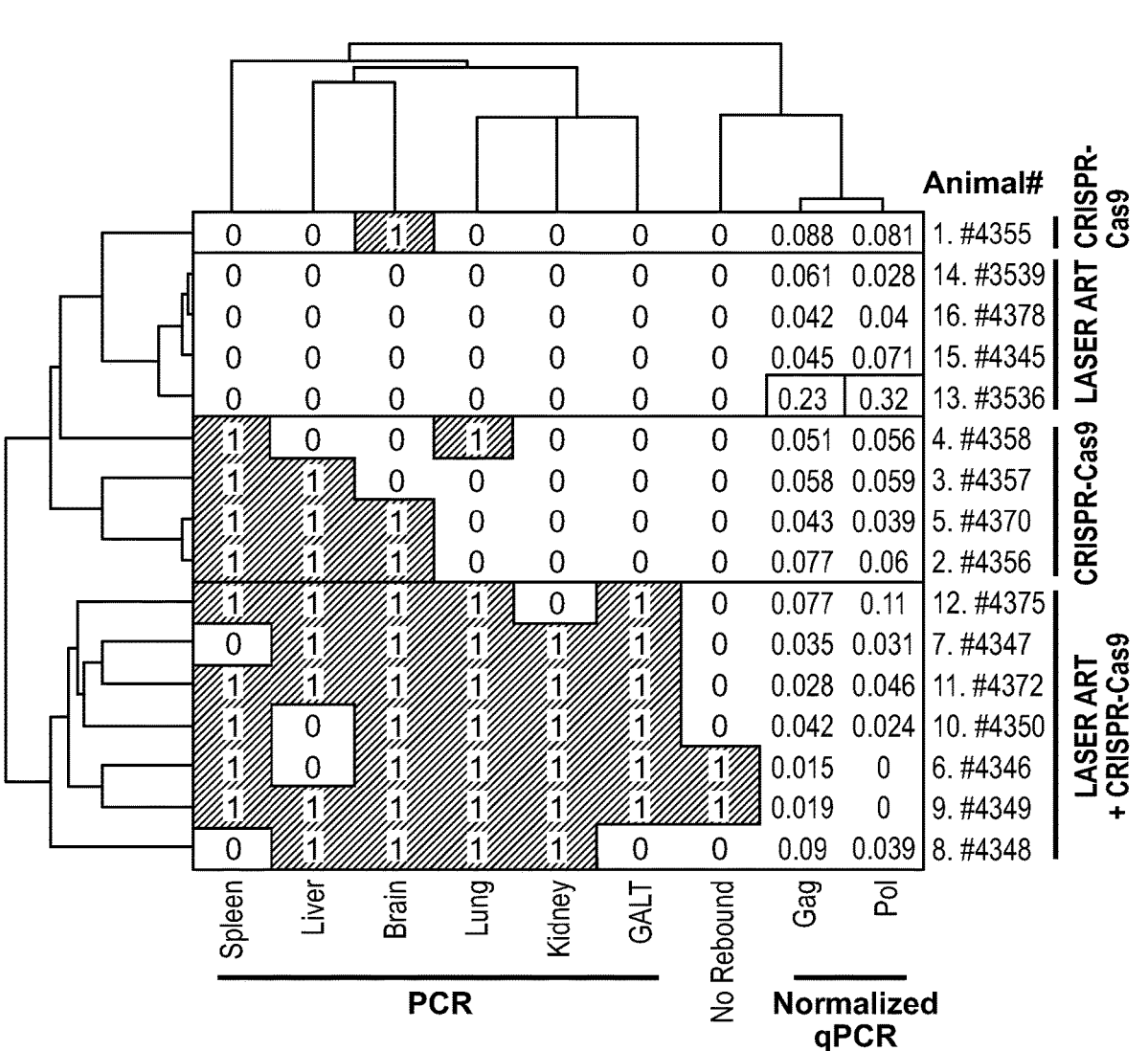

FIGS. 16A-16C show the hierarchical clustering analysis of the truncation efficiencies across different animals, treatments, tissues and HIV-1 gene segments. Probabilities are shown with the numbers as well as the heat-map intensities. Most similar groups are clustered together. Dendrograms indicate the hierarchy of clusters for each axis. FIG. 16A: Clustering of truncation efficiencies of different HIV-1 segments in different tissues under ART, CRISPR-Cas9 and ART plus CRISPR-Cas9 treatments. The clustering reveals the most similarity between ART plus CRISPR-Cas9-mediated editing in GALT, spleen and lung. FIG. 16B: Clustering of truncation efficiencies of different HIV-1 segments and qPCR data in different animals under ART, CRISPR-Cas9 and ART plus CRISPR-Cas9 treatments. The clustering scheme has recognized the similarity patterns and grouped the animals with the similar treatments under the same clusters. FIG. 16C: Clustering of truncation efficiencies in different tissues of the animals under the aforementioned treatments. Note that the animals with no rebound (treated with both LASER ART and AAV$_9$-CRISPR-Cas9) exhibit similar patterns in excision probabilities both across different HIV-1 segments and across different tissues. These analyses are later used in drawing the significance levels of combined treatment in viral genome eradication compared to the control groups. S1 refers to 5' LTR-Gag and S2 refers to Gag-3' LTR of the HIV-1 gene, respectively.

Figure 17A:
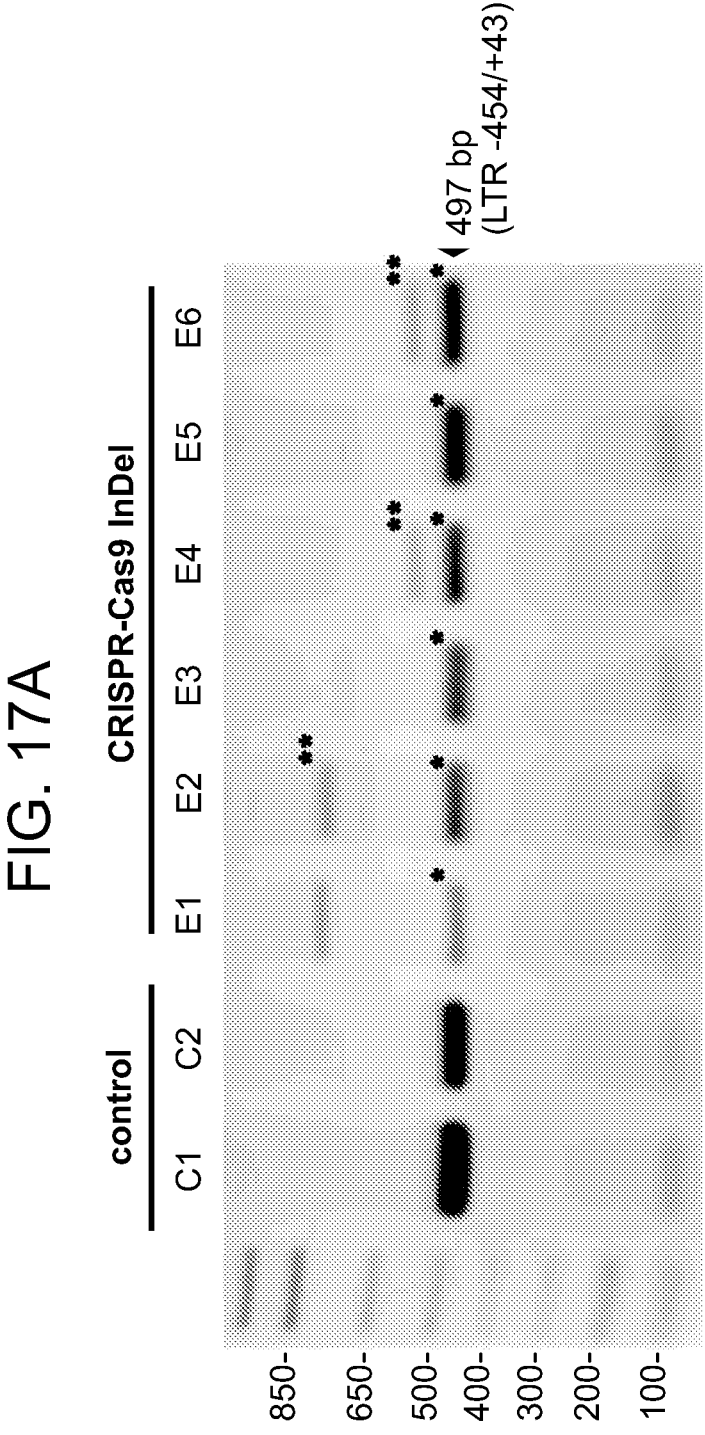
Figure 17B:
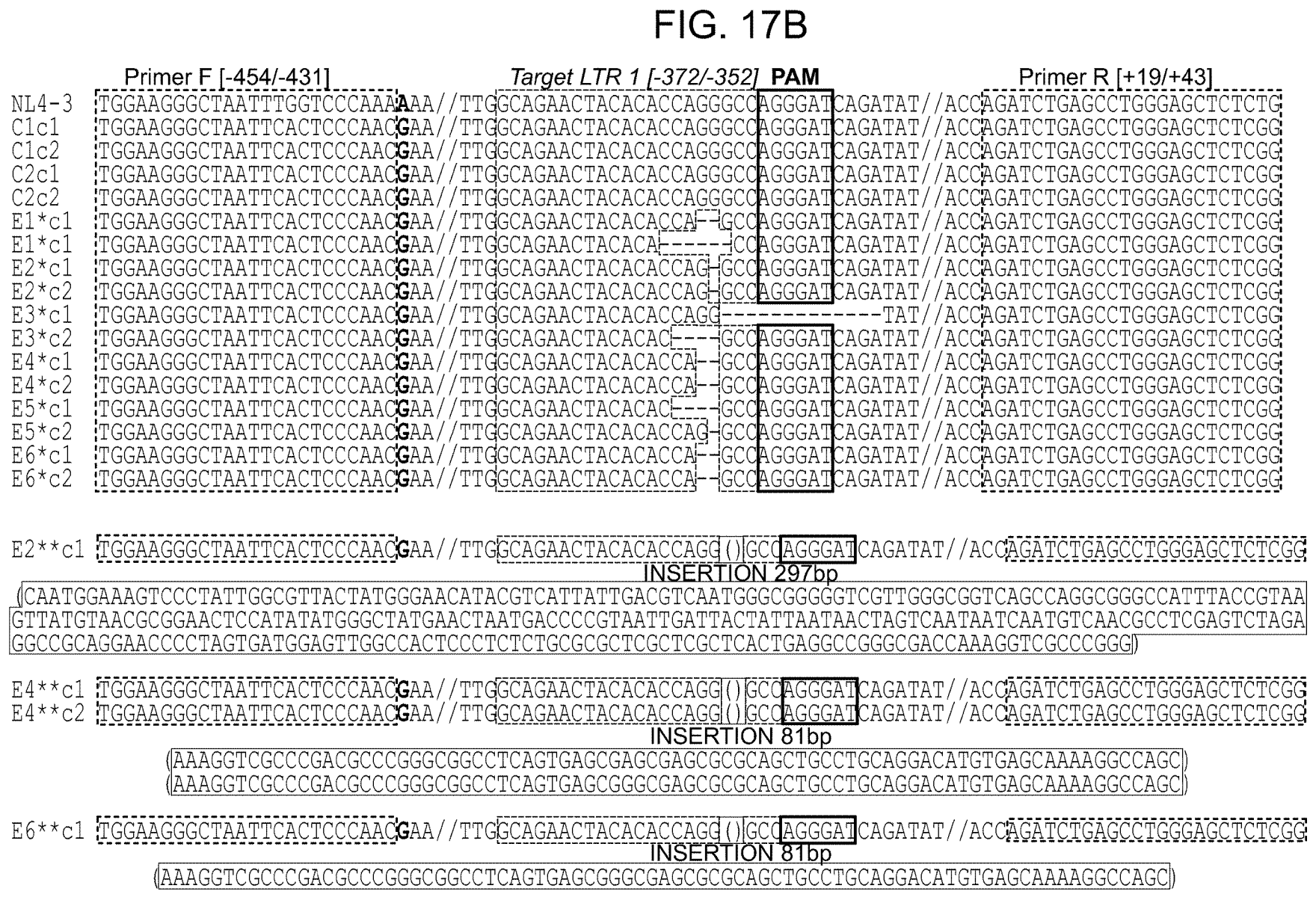
Figure 17C:
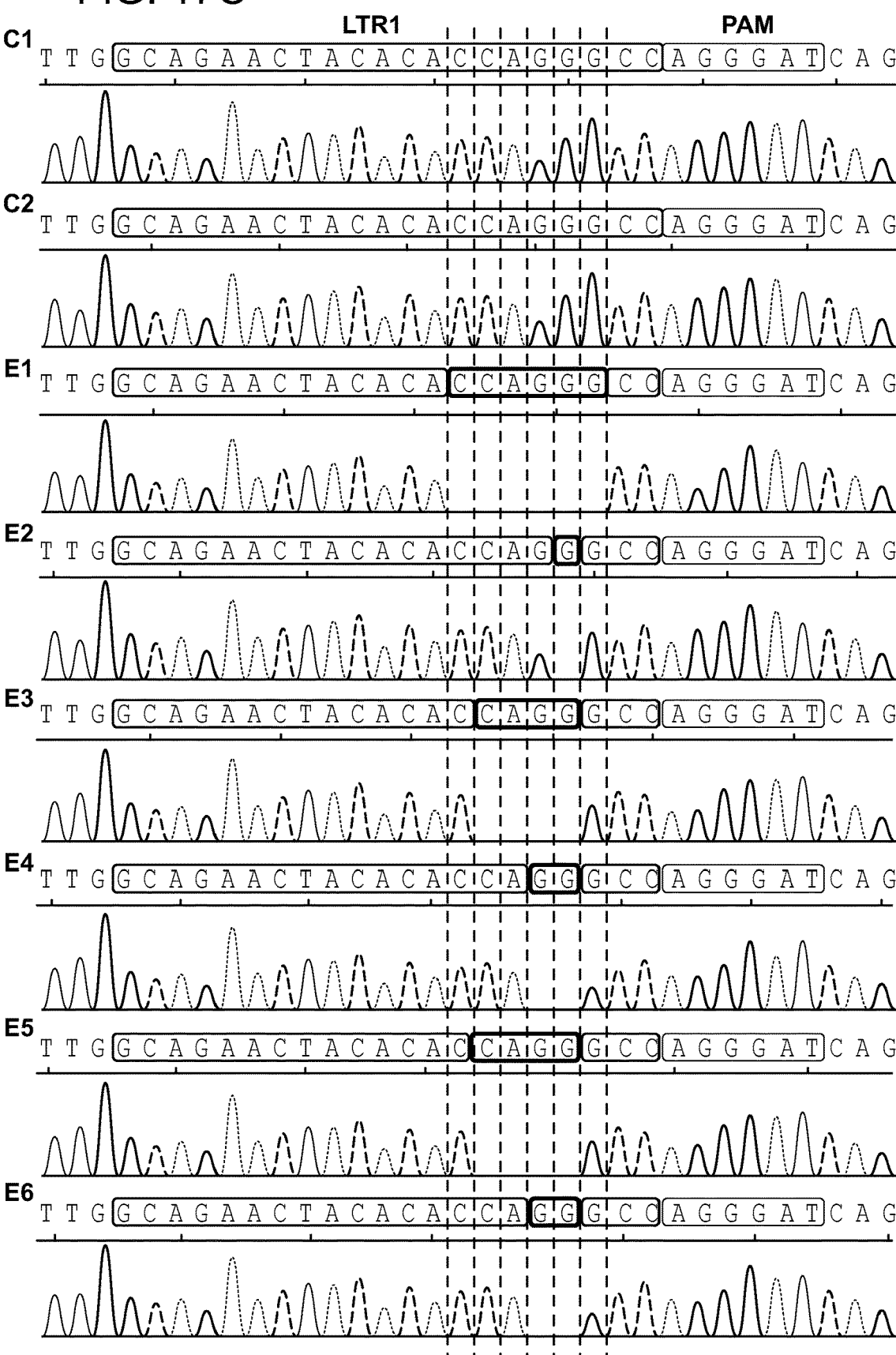

FIGS. 17A-17C show the Off target effect in cell model (FIG. 17A) of genomic DNA obtained from TZM-bl single cell clones: two controls (C1-2) and six Cas9/gRNA LTR 1+Gag D treated (E1-6). The presence of full length LTR-454/+43 (497 bp) was examined. Amplicons containing CRISPR-Cas9 specific InDel mutations at the LTR 1 target site in integrated HIV-1 LTR sequence are pointed by asterisks. Single asterisks indicate deletions, double asterisks insertions. FIG. 17B: Alignment of a representative Sanger sequencing results of HIV-1 LTR specific amplicons. FIG. 17B discloses SEQ ID NOS 267-270, 268, 271, 270, 268, 271, 270, 268, 271, 270, 268, 271, 270, 272, 271, 270, 273, 271, 270, 274, 271, 270, 275, 271, 270, 276, 271, 270, 277, 271, 270, 278, 271, 270, 278, 271, 270, 277, 271, 270, 274, 271, 270, 278, 271, 270, 278, 271, 270, 279, 271, 307, 270, 280, 271, 270, 281, 271, 308-309, 270, 282, 271 and 310, all respectively, in order of appearance. FIG. 17C: Representative Sanger sequencing tracing of LTR 1 region of HIV-1 LTRs obtained for each single cell clone. FIG. 17C discloses SEQ ID NOS 283-290, respectively, in order of appearance.

Figures 18A, 18B, 18C, 18D, 18E, 18F:
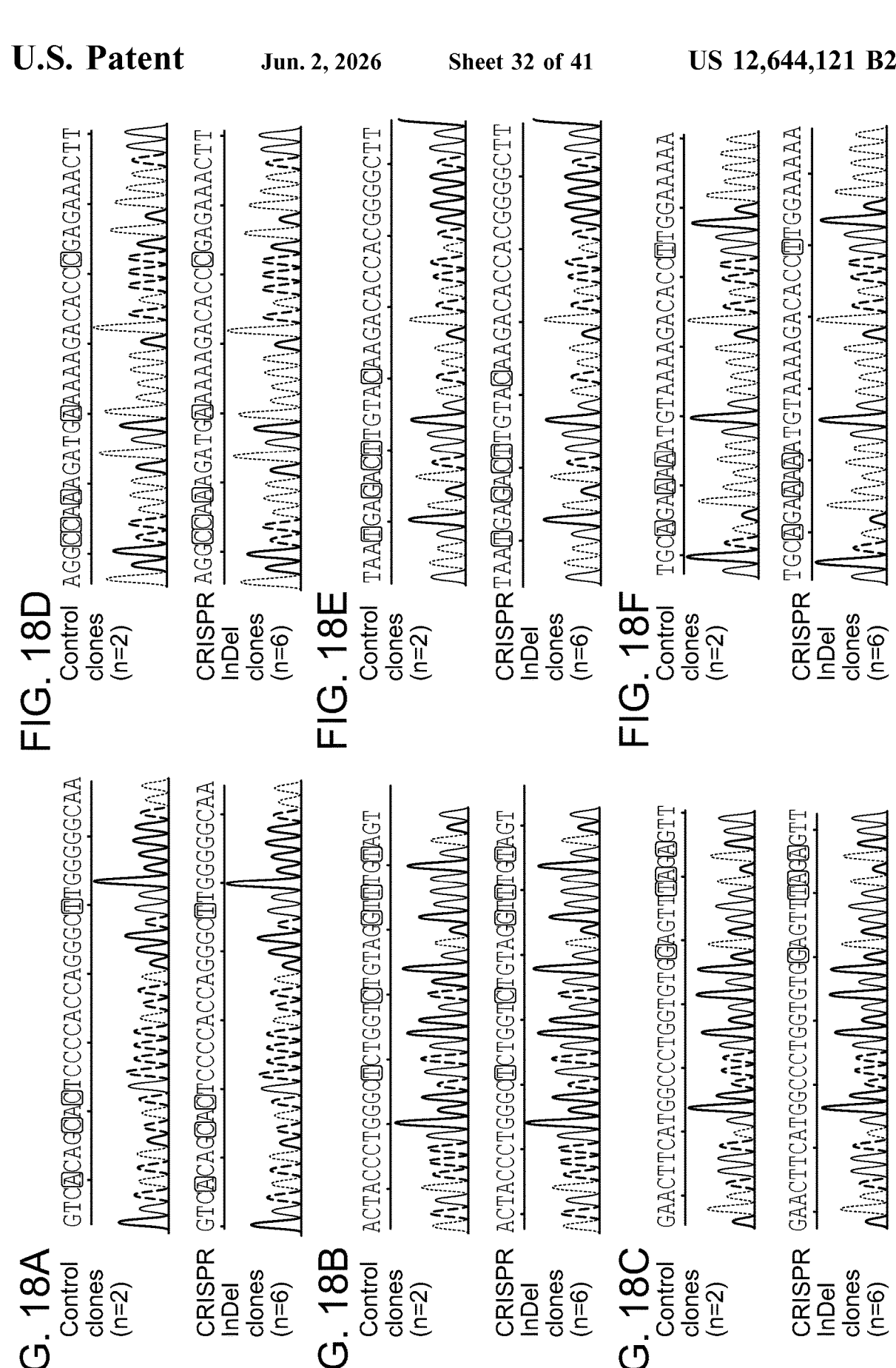

FIGS. 18A-18F show representative Sanger sequencing tracing of predicted three Off target regions for gRNAs LTR 1 and Gag D obtained for each single cell clone. Squares point mismatched nucleotides comparing to target sequences. LTR 1 off target sites: TSC2 (FIG. 17A), TUB (FIG. 17B) and ch8 (FIG. 17C). Gag D off target sites: TACC2 (FIG. 17D), ADNP (FIG. 17E) and ch3 (FIG. 17F). No any InDel mutations at the predicted off target sites was detected. See also Tables 4 and 5. FIG. 18A discloses SEQ ID NOS 291-292, respectively, in order of appearance. FIG. 18B discloses SEQ ID NOS 293-294, respectively, in order of appearance. FIG. 18C discloses SEQ ID NOS 295-296, respectively, in order of appearance. FIG. 18D discloses SEQ ID NOS 297-298, respectively, in order of appearance. FIG. 18E discloses SEQ ID NOS 299-300, respectively, in order of appearance. FIG. 18F discloses SEQ ID NOS 301-302, respectively, in order of appearance.

Figure 19A:
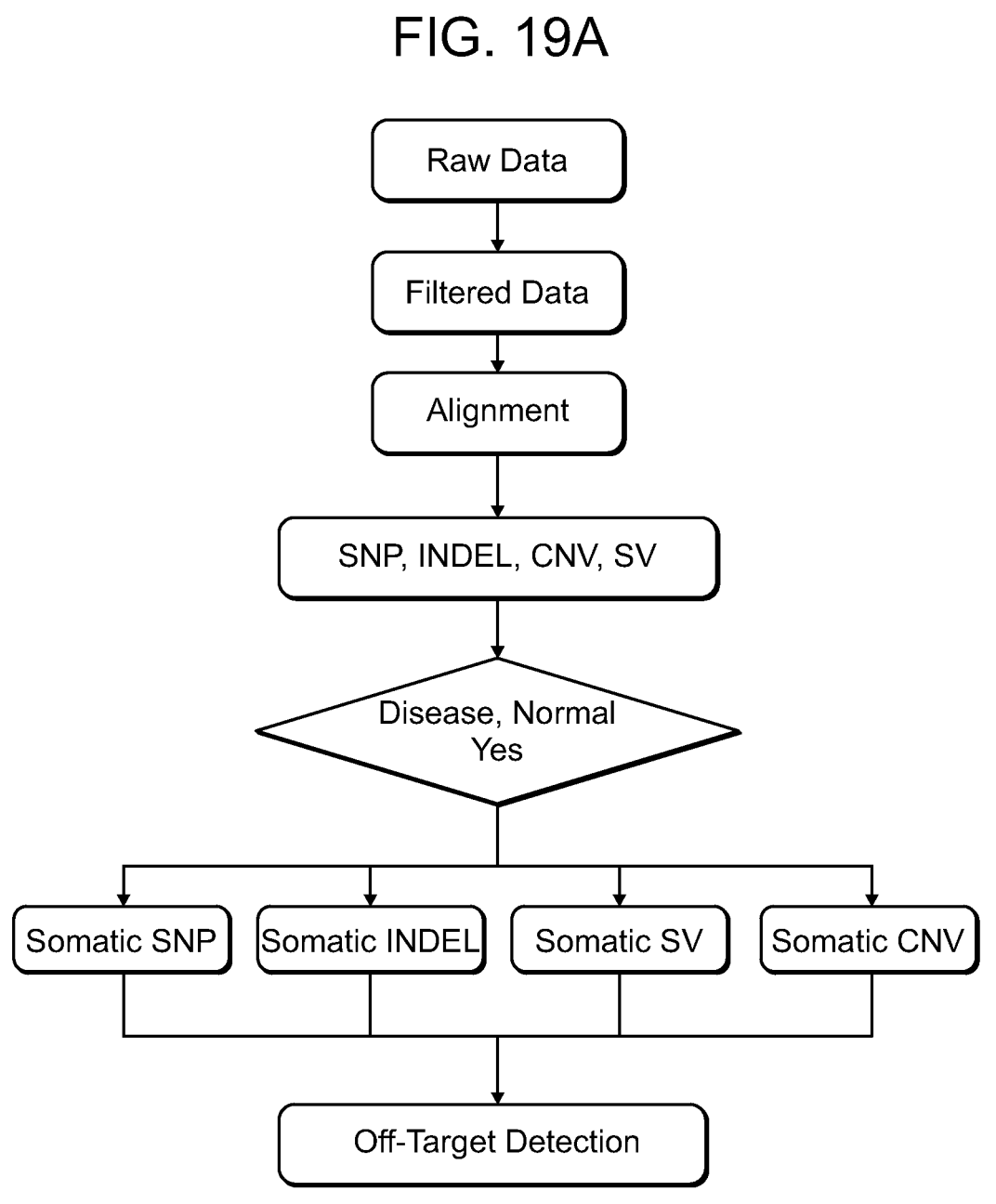
Figure 19B:
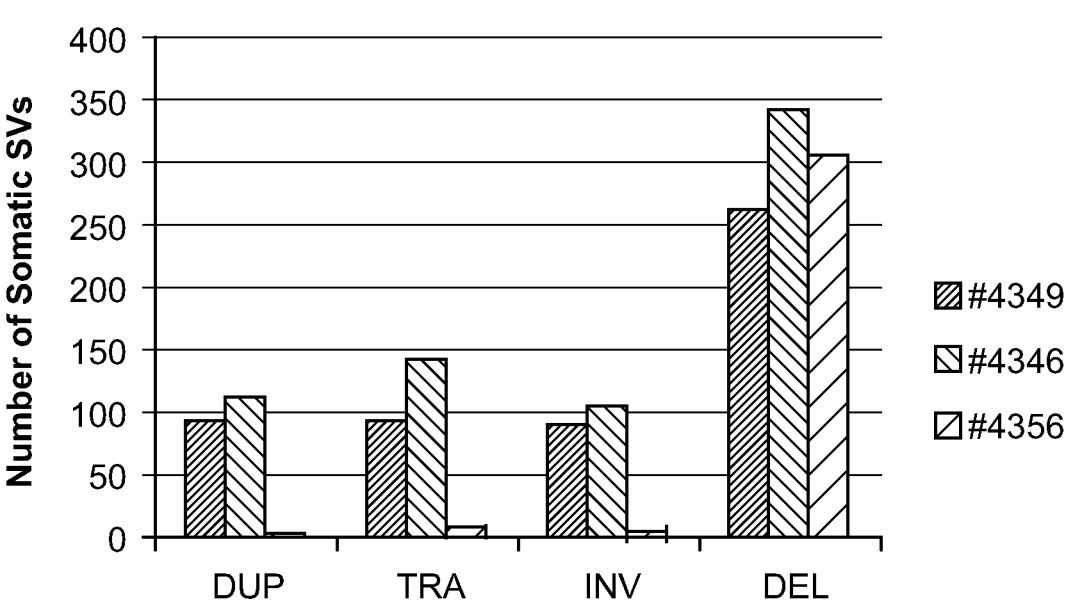
Figure 19C:
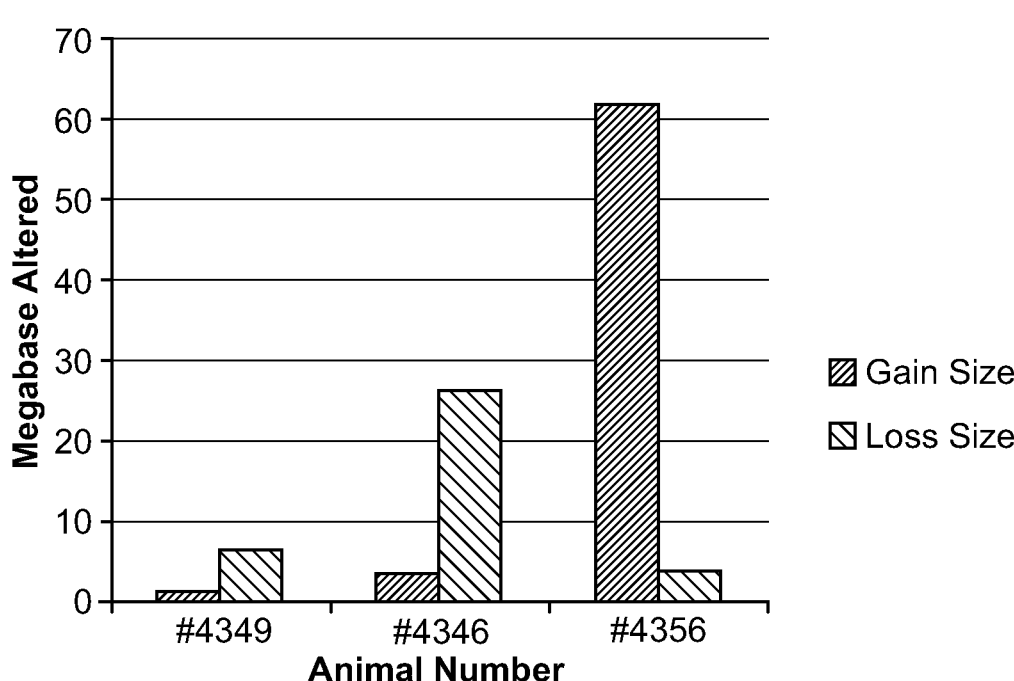
Figure 20A:
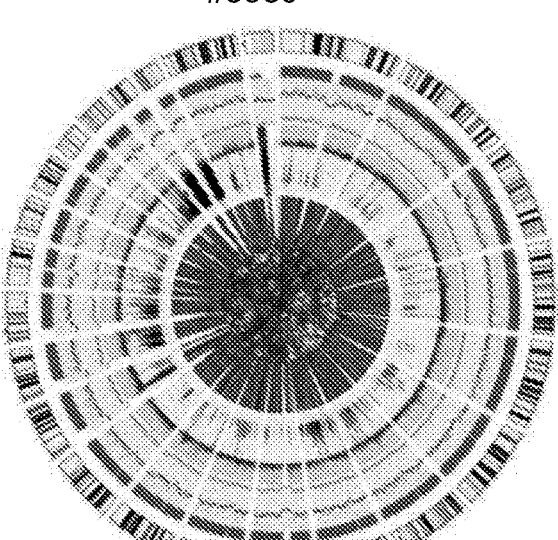
Figure 20B:
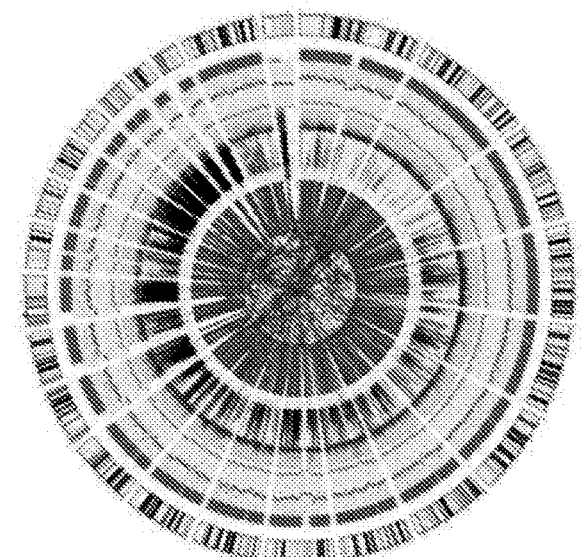
Figure 20C:
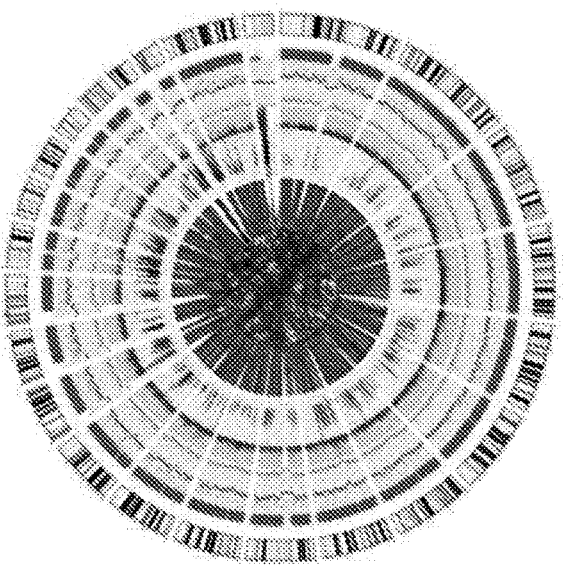
Figure 20D:
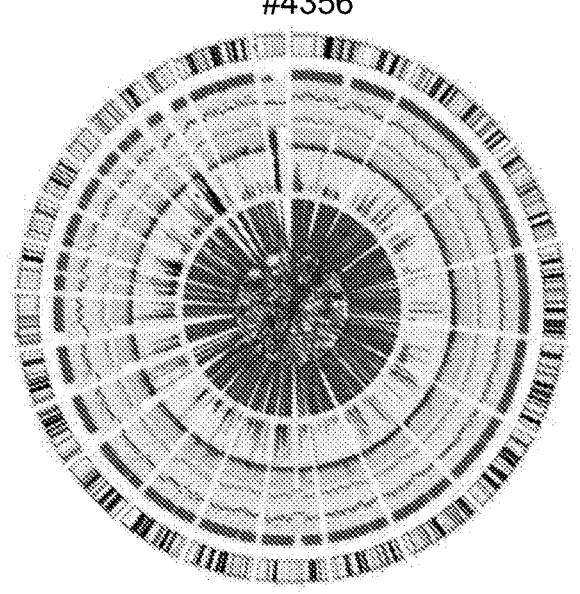

FIGS. 19A-19C show the appearance of Somatic mutations in humanized mice. FIG. 19A: Sequence of NGS data analysis steps used for off target detection. FIG. 19B: Number of different types of somatic structural variations (SV) in each sample. Abbreviations: TRA: (Translocation) the number of translocations, INV: (Inversions) the number of inversions, DEL: (Deletion) the number of deletions, DUP: (Tandem duplication) the number of tandem duplications, INS: (Insertion) the number of insertions. FIG. 19C: The size of genomic regions affected by somatic CNVs in each sample.

FIGS. 20A-20D are Circos diagrams of the animals (FIG. 20A), #3539 ((LASER ART), (FIG. 20B) #4346 and, (FIG. 20C) #4349 (CRISPR-Cas9+LASER ART), and (FIG. 20D) #4356 (CRISPR-Cas9). The diagrams consist of seven rings. From outer to inner rings: (1) the outer circle (the first circle) is chromosome information. (2) The second ring represents the read coverage in histogram style. A histogram is the average coverage of a 0.5 Mbp region. (3) The third ring represents InDel density in scatter style. A black dot is calculated as InDel number in a range of 1 Mbp. (4) the fourth ring represents SNP density in scatter style. A dot is calculated as SNP number in a range of 1 Mbp. (5) the fifth ring represents the proportion of homozygous SNP and heterozygous SNP in histogram style. A histogram is calculated from a 1 Mbp region. (6) The sixth ring represents the CNV inference. (7) The most central ring represents the SV inference in exonic and splicing regions.

FIGS. 21A, 21B are an analysis of humanized mice tissues using highly sensitive ddPCR assay to detect HIV-1. Ultrasensitive droplet digital PCR (ddPCR) with sensitivity of detecting 1-2 copies was used to detect viral DNA in spleen of the infected animals belonging to 4 groups, control infected, LASER ART or AAV$_9$-CRISPR-CAs9 alone treated and dual treatment (LASER ART+Cas9) (FIG. 21A) and the various organs of the two mice with no viral rebound (FIG. 21B). Note that the two animals with double treatment group (group-4, #4346 and #4349) showed complete elimination of virus in spleen and the other tissues (Lung, liver, GALT, brain and Kidney) tested.

FIGS. 22A and 22B show a viral recovery assay using co-culture method. FIG. 22A: Splenocytes and bone marrow cells were isolated from HIV-1 infected mice with or without prior LASER ART and/or CRISPR-Cas9 treatments then co-cultivated with PHA/IL-2 stimulated human PBMCs. Cells were harvested 12 days post-cocultivation for HIV-1 DNA (FIG. 22A) and (FIG. 22B) RNA and looked to examine rebound virus using highly sensitive semi-nested real-time q-PCR assay. Data are expressed as total viral copies/$10^6$ human CD45$^+$ cells. Dual LASER ART and CRISPR-Cas9 treatments mice resulted in no detection of viral nucleic acids, which were also confirmed by reverse transcriptase assay of culture supernatants. Virus was detected in all other groups of animals.

Figure 23:
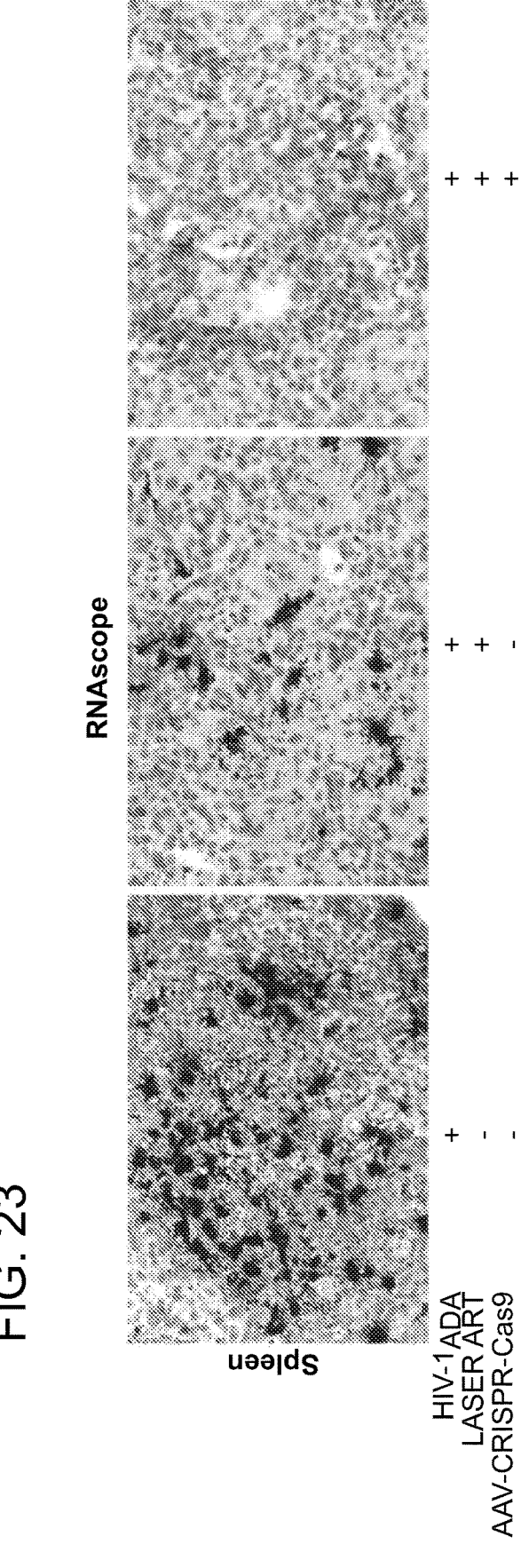

FIG. 23 shows tissue analyses of HIV-1ADA infected and treated humanized mice by RNAscope. RNAscope was used to detect viral RNA in spleens and demonstrating single brown dots or cluster of dots in 5-μm thick sections. The assays used antisense probeV-HIV-1-Calde-B targeting 854-

8291 base pairs of the HIV-1 genome. Mouse #3319 which received LASER ART and AAV$_9$-CRISPR-Cas9, showed no viral detection signals. Viral RNA was detected in other 2 groups of humanized mice spleen (HIV-1$_{ADA}$ infected and infected+LASER ART treated) as shown. The photomicrographs are representative images from each group. Human peptidyl Isomerase B (PPIB) was used as a positive control for every tissue analyzed. Images are 40× magnifications.

Figure 24:
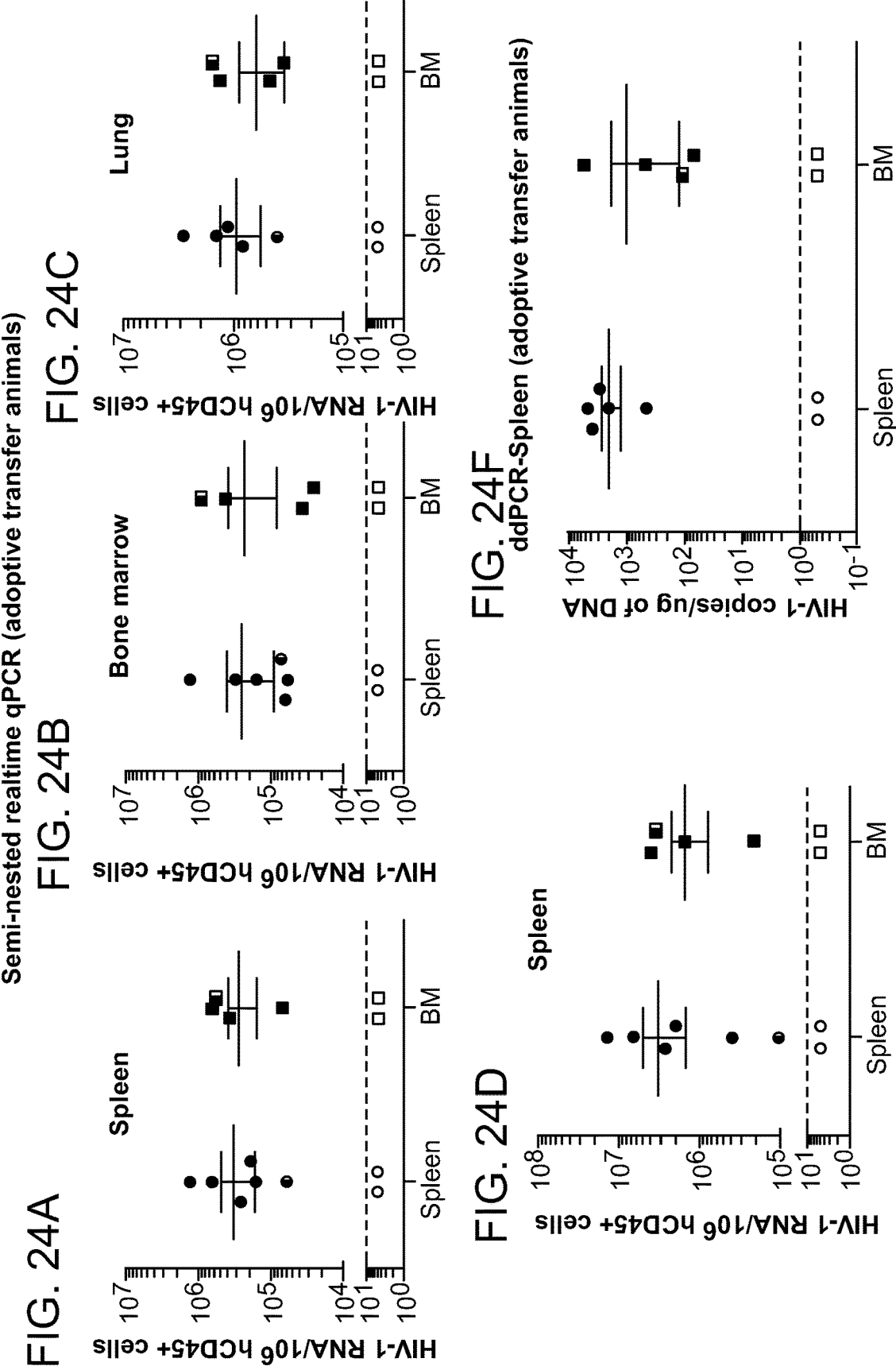

FIGS. 24A-24E show the detection of HIV-1$_{ADA}$ DNA and RNA in spleen tissues in adoptively transferred humanized mice. Splenocytes and bone marrow cells were isolated from HIV-1 infected mice with or without prior LASER ART and or CRISPR-Cas9 treatments. These were for adoptive transfers into "new" CD34+NSG-humanized mice. The intent was to perform cross disciplinary viral amplification from known infectious cell reservoirs. FIGS. 24A, 24B and 24C: HIV-1 DNA and (FIG. 24D) RNA analyses using ultrasensitive semi-nested real-time qPCR assays from spleen, bone marrow and lung tissues of adoptively transferred humanized mice. The data are expressed as total HIV-1 DNA or RNA copies/10$^6$ human CD45$^+$ cells. Four animals (splenocyte and bone marrow cells isolated and adoptively transferred from #3319 and #3336) mice, showed no viral recovery. The above data was further confirmed using ultrasensitive ddPCR assay (with sensitivity of 1-2 copies), where the same four target adoptively transferred recipient animals showed no HIV-1 and (FIG. 24E) indicating complete elimination of virus. In mice from HIV-1$_{ADA}$ infected with or without LASER ART treatment showed easily recovered virus in the spleen tissues. These results provide definitive testing of viral eradication in the two tested and the assayed mice (#3319 and #3336).

Figure 25:
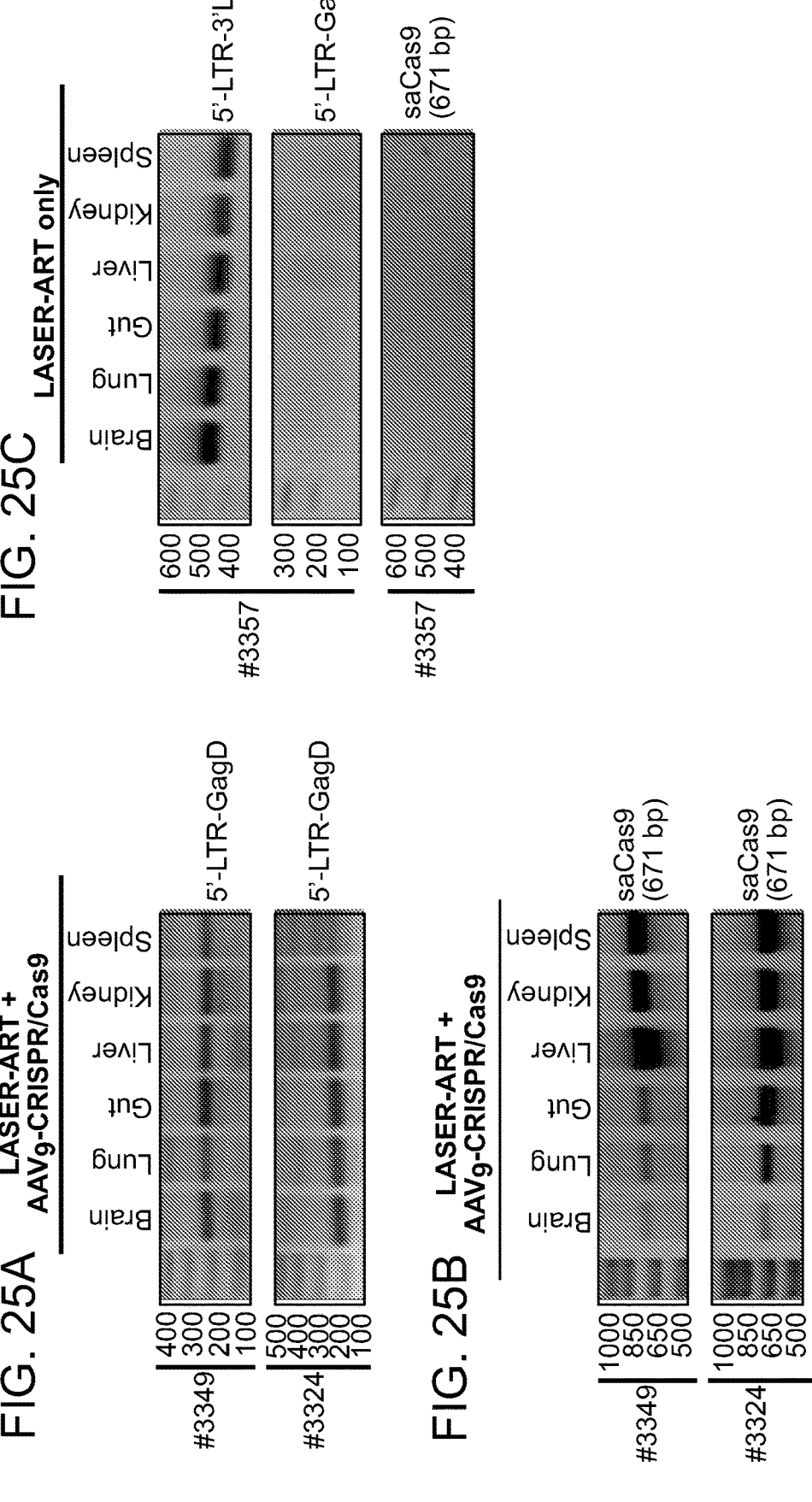

FIGS. 25A-25C show the excision of HIV proviral DNA by CRISPR-Cas9 in HIV$_{ADA}$-infected humanized mice. A much shorter fragment (193 bp) of excised HIV proviral DNA from the 5'LTR to gag region was amplified by nested-PCR in total genomic DNA extracted from various tissues of each humanized mice (#3324 and #3349) (FIG. 25A) along with the presence of SaCas9 DNA in each tissue (FIG. 25B). HIV excision was not detected in the humanized mouse treated with LASER ART only (#3357) even though a full length of HIV-1 LTR could be amplified abundantly to reveal the existence of HIV proviral DNA (FIG. 25C).

Figure 26:

FIG. 26 shows liver tissue histology following therapy in humanized mice. Hematoxylin and eosin staining of representative sections from liver tissues in uninfected, HIV-1$_{ADA}$-infected, infected and LASER ART treated and dual treated (LASER ART+AAV$_9$-CRISPR-Cas9) humanized mice at the endpoint of the study. Tissue pathology was not observed in LASER ART alone nor the dual treatment mice group. All images were captured at 10-× magnification.

Figure 27:
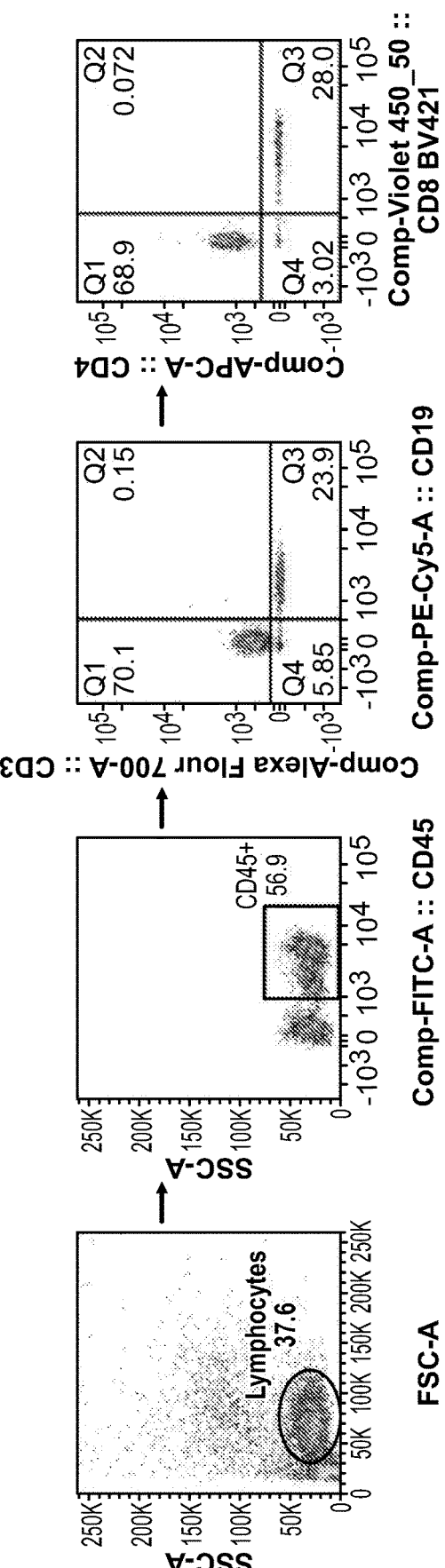

FIG. 27 shows the gating strategy. Blood cells were first gated for mononuclear cells and lymphocytes using forward and side scattered panels (FSC and SSC). From the gated lymphocyte population, human CD45$^+$ cells were re-gated in side-scatter panel. Gated human CD45$^+$ mononuclear cells were assessed for expression of human CD3 (T cells) and CD19 (B cells). CD3$^+$ T cells were further gated to assess the expression of CD4 and CD8 cells.

DETAILED DESCRIPTION

Embodiments of the invention are directed in general to nanoparticle delivery of long-acting, slow effective release (LASER) antiretroviral therapy (ART) and gene editing technologies.

Briefly, the invention is based, in part, on the finding that treatment of HIV-1 infected humanized mice with CRISPR-Cas9 designed to edit the HIV-1 genome following two months treatment with the newly developed long-acting, slow effective release ART (LASER ART) eradicated HIV-1 infection in twenty-nine percent of infected animals with restored CD4$^+$ T cells. Ultrasensitive nested and digital droplet PCR and RNA scope assays failed to detect HIV-1 in blood, spleen, lung, kidney, liver, gut-associated lymphoid tissue and brain. Excision of proviral DNA fragments spanning the LTRs and the Gag gene by CRISPR/Cas9, in the absence of any off target effects, along with the lack of viral rebound following cessation of ART with no progeny virus recovery verified HIV-1 eradication. Thus, the sequential application of antiretroviral agents and CRISPR-Cas9 therapies administered to HIV-1 infected humanized mice provided the first proof of concept that viral sterilization is possible.

LASER ART: Long-acting slow effective release ART (LASER ART) enable improved pharmacokinetic profiles and reservoir targeting. These antiretrovirals (ARVs) overcome limitations of current drugs associated with in vivo delivery and tissue penetrance. The gene editing agent also had improved delivery and improved the therapeutic index of the drugs.

Dolutegravir, lamivudine, abacavir and rilpivirine (DTG, 3TC, ABC and RPV respectively were transformed into long-acting drugs. Drug solubility, dissolution, metabolism, protein-binding, and excretion rates for each of the antiretroviral drugs were optimized and each were shown to influence the drug's half-life and biodistribution profiles. These studies provided the means to transform standard daily or twice-daily antiretroviral drugs into hydrophobic drug crystals to extend the drug's half-life and alter its solubility and metabolic patterns. The drugs were found to possess significant antiretroviral efficacy and high tolerability for conversion into a long-acting compound. Reversible chemical modification and polymer coating techniques were developed to convert each into a long-acting nanoformulation. Change of the antiretroviral drug (ARV) structure was made through reversible myristoylation of the native compound creating a water insoluble prodrug with commensurate crystal formation. When the drug crystals were packaged into a nanoparticle, they were rapidly taken up by human monocyte-derived macrophages (MDM), slowly released from the cells, and retained for a prolonged period inside the macrophage. These chemical and biological outcomes improved drug bioavailability and increased in vitro antiretroviral activity up to 100-fold. Pharmacokinetic and pharmacodynamic profiles were improved up to 10-fold over a native drug formulation, exhibiting broad tissue distribution and increased potency. The studies herein provide evidence that ARV conversion into a long-acting slow release formulation is readily achieved. As such, the drug-encased nanoparticles were employed as a "first-step" measure to facilitate drug penetrance into viral reservoirs to facilitate the actions of the excision Cas9 system.

Accordingly, in certain embodiments, the anti-retroviral agents are formulated into long-acting nanoformulated agents or compounds.

Gene Editing Agents: The application of Cas9 technology in eradicating HIV-1 reservoir, particularly targeting LTR, has been shown to be a promising strategy for treating and possibly curing AIDS. Hu, et al., *PNAS* 2014, 111:114616, disclosed that stable transfection of human cell cultures with plasmids expressing Cas9/gRNAs targeted to sites in the HIV-1 LTR successfully eradicated part and/or the entire HIV-1 genome without compromising host cell function. The targeted sites were termed LTR-A. LTR-B, LTR-C, and LTR-D. The targeting of two different sites in the LTR was particularly effective at producing the deletions sufficiently extensive to constitute the excision of all or substantially all of the proviral DNA sequence. The pre-existence of Cas9/gRNAs in cells also prevented new HIV-1 infection.

HIV and other retroviruses are highly mutable, so there is a need for a broader spectrum of Cas9/gRNA reagents and methods for targeting the integrated HIV genome. Of particular use would be Cas9/gRNA reagents that effectively target various genes in the viral genome, such as for example, structural genes of HIV, such as gag and pol; genes that encode ligands that allow for viral entry into cells, etc.

Accordingly, embodiments of the invention are directed to compositions and methods for the treatment and eradication of highly mutable and/or latent viruses from a host cell in vitro or in vivo. Methods of the invention may be used to remove viral or other foreign genetic material from a host organism, without interfering with the integrity of the host's genetic material. A nuclease may be used to target viral nucleic acid, thereby interfering with viral replication or transcription or even excising the viral genetic material from the host genome. The nuclease may be specifically targeted to remove only the viral nucleic acid without acting on host material either when the viral nucleic acid exists as a particle within the cell or when it is integrated into the host genome. Targeting the viral nucleic acid can be done using a sequence-specific moiety such as a guide RNA that targets viral genomic material for destruction by the nuclease and does not target the host cell genome. In some embodiments, a CRISPR/Cas nuclease and guide RNA (gRNA) that together target and selectively edit or destroy viral genomic material is used. The CRISPR (clustered regularly inter-spaced short palindromic repeats) is a naturally-occurring element of the bacterial immune system that protects bacteria from phage infection. The guide RNA localizes the CRISPR/Cas complex to a viral target sequence. Binding of the complex localizes the Cas endonuclease to the viral genomic target sequence causing breaks in the viral genome. Other nuclease systems can be used including, for example, zinc finger nucleases, transcription activator-like effector nucleases (TALENs), meganucleases, or any other system that can be used to degrade or interfere with viral nucleic acid without interfering with the regular function of the host's genetic material.

The compositions embodied herein, can be used to target viral nucleic acid in any form or at any stage in the viral life cycle. Together, with the combination of LASER-ART therapeutics, renders these compositions formidable in the treatment and/or prevention of infection by a retroviruses, e.g. HIV. The targeted viral nucleic acid may be present in the host cell as independent particles. In a preferred embodiment, the viral infection is latent and the viral nucleic acid is integrated into the host genome. Any suitable viral nucleic acid may be targeted for cleavage and digestion.

CRISPR/Cas Systems: The CRISPR-Cas system includes a gene editing complex comprising a CRISPR-associated nuclease, e.g., Cas9, and a guide RNA complementary to a target sequence situated on a DNA strand, such as a target sequence in proviral DNA integrated into a mammalian genome. The gene editing complex can cleave the DNA within the target sequence. This cleavage can in turn cause the introduction of various mutations into the proviral DNA, resulting in inactivation of HIV provirus. The mechanism by which such mutations inactivate the provirus can vary. For example, the mutation can affect proviral replication, and viral gene expression. The mutations may be located in regulatory sequences or structural gene sequences and result in defective production of HIV. The mutation can comprise a deletion. The size of the deletion can vary from a single nucleotide base pair to about 10,000 base pairs. In some embodiments, the deletion can include all or substantially all of the integrated retroviral nucleic acid sequence. In some embodiments the deletion can include the entire integrated retroviral nucleic acid sequence. The mutation can comprise an insertion, that is, the addition of one or more nucleotide base pairs to the pro-viral sequence. The size of the inserted sequence also may vary, for example from about one base pair to about 300 nucleotide base pairs. The mutation can comprise a point mutation, that is, the replacement of a single nucleotide with another nucleotide. Useful point mutations are those that have functional consequences, for example, mutations that result in the conversion of an amino acid codon into a termination codon or that result in the production of a nonfunctional protein.

In general, CRISPR/Cas proteins comprise at least one RNA recognition and/or RNA binding domain. RNA recognition and/or RNA binding domains interact with guide RNAs. CRISPR/Cas proteins can also comprise nuclease domains (i.e., DNase or RNase domains), DNA binding domains, helicase domains, RNAse domains, protein-protein interaction domains, dimerization domains, as well as other domains. Active DNA-targeting CRISPR-Cas systems use 2 to 4 nucleotide protospacer-adjacent motifs (PAMs) located next to target sequences for self versus non-self discrimination. ARMAN-1 has a strong 'NGG' PAM preference. Cas9 also employs two separate transcripts, CRISPR RNA (crRNA) and trans-activating CRISPR RNA (tracrRNA), for RNA-guided DNA cleavage. Putative tracrRNA was identified in the vicinity of both ARMAN-1 and ARMAN-4 CRISPR-Cas9 systems (Burstein, D. et al. New CRISPR-Cas systems from uncultivated microbes. *Nature.* 2017 Feb. 9; 542(7640):237-241. doi: 10.1038/nature21059. Epub 2016 Dec. 22).

In embodiments, the CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzymatic activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the function of the fusion protein. The CRISPR/Cas-like protein can also be truncated or modified to optimize the activity of the effector domain of the fusion protein.

In embodiments, the CRISPR/Cas system can be a type I, a type IL, or a type III system. Non-limiting examples of suitable CRISPR/Cas proteins include Cas9, CasX, CasY.1, CasY.2, CasY.3, CasY.4, CasY.5, CasY.6, spCas, eSpCas, SpCas9-HF1, SpCas9-HF2, SpCas9-HF3, SpCas9-HF4, ARMAN 1, ARMAN 4, Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966.

The Cas9 can be an orthologous. Six smaller Cas9 orthologues have been used and reports have shown that Cas9 from *Staphylococcus aureus* (SaCas9) can edit the genome with efficiencies similar to those of SpCas9, while being more than 1 kilobase shorter.

In addition to the wild type and variant Cas9 endonucleases described, embodiments of the invention also encompass CRISPR systems including newly developed "enhanced-specificity" *S. pyogenes* Cas9 variants (eSpCas9), which dramatically reduce off target cleavage. These variants are engineered with alanine substitutions to neutralize positively charged sites in a groove that interacts with the non-target strand of DNA. This aim of this modification is to reduce interaction of Cas9 with the non-target strand, thereby encouraging re-hybridization between target and non-target strands. The effect of this modification is a requirement for more stringent Watson-Crick pairing between the gRNA and the target DNA strand, which limits off-target cleavage (Slaymaker, I. M. et al. (2015) DOI: 10.1126/science.aad5227).

In certain embodiments, three variants found to have the best cleavage efficiency and fewest off-target effects: SpCas9 (K855A), SpCas9 (K810A/K1003A/R1060A) (a.k.a. eSpCas9 1.0), and SpCas9(K848A/K1003A/ R1060A) (a.k.a. eSPCas9 1.1) are employed in the compositions. The invention is by no means limited to these variants, and also encompasses all Cas9 variants (Slaymaker, I. M. et al. *Science*. 2016 Jan. 1; 351(6268):84-8. doi: 10.1126/science.aad5227. Epub 2015 Dec. 1). The present invention also includes another type of enhanced specificity Cas9 variant, "high fidelity" spCas9 variants (HF-Cas9). Examples of high fidelity variants include SpCas9-HF1 (N497A/R661A/Q695A/Q926A), SpCas9-HF2 (N497A/ R661A/Q695A/Q926A/D1135E), SpCas9-HF3 (N497A/ R661A/Q695A/Q926A/L169A), SpCas9-HF4 (N497A/ R661A/Q695A/Q926A/Y450A). Also included are all SpCas9 variants bearing all possible single, double, triple and quadruple combinations of N497A, R661A, Q695A, Q926A or any other substitutions (Kleinstiver, B. P. et al., 2016, *Nature*. DOI: 10.1038/nature16526).

As used herein, the term "Cas" is meant to include all Cas molecules comprising variants, mutants, orthologues, high-fidelity variants and the like.

In one embodiment, the endonuclease is derived from a type II CRISPR/Cas system. In other embodiments, the endonuclease is derived from a Cas9 protein and includes Cas9, CasX, CasY.1, CasY.2, CasY.3, CasY.4, CasY.5, CasY.6, spCas, eSpCas, SpCas9-HF1, SpCas9-HF2, SpCas9-HF3, SpCas9-HF4, ARMAN 1, ARMAN 4, mutants, variants, high-fidelity variants, orthologs, analogs, fragments, or combinations thereof. The Cas9 protein can be from *Streptococcus pyogenes, Streptococcus thermophilus, Streptococcus* sp., *Nocardiopsis dassonvillei, Streptomyces* pristinaespiralis, *Streptomyces viridochromogenes, Streptomyces viridochromogenes, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina*, Burkholderiales *bacterium, Polaromonas naphthalenivorans, Polaromonas* sp., Crocosphaera *watsonii*, Cyanothece sp., *Microcystis aeruginosa, Synechococcus* sp., *Acetohalobium arabaticum, Ammonifex degensii*, Caldicelulosiruptor becscii, *Candidatus* Desulforudis, *Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Metha-*

*nohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus*, or Acaryochloris *marina*. Included are Cas9 proteins encoded in genomes of the nanoarchaea ARMAN-1 (*Candidatus* Micrarchaeum acidiphilum ARMAN-1) and ARMAN-4 (*Candidatus* Parvarchaeum acidiphilum ARMAN-4), CasY (Kerfeldbacteria, Vogelbacteria, Komeilibacteria, Katanobacteria), CasX (Planctomycetes, Deltaproteobacteria).

Embodiments of the invention also include a new type of class 2 CRISPR-Cas system found in the genomes of two bacteria recovered from groundwater and sediment samples. This system includes Cas1, Cas2, Cas4 and an approximately ~980 amino acid protein that is referred to as CasX. The high conservation (68% protein sequence identity) of this protein in two organisms belonging to different phyla, Deltaproteobacteria and Planctomycetes, suggests a recent cross-phyla transfer. The CRISPR arrays associated with each CasX has highly similar repeats (86% identity) of 37 nucleotides (nt), spacers of 33-34 nt, and a putative tracrRNA between the Cas operon and the CRISPR array. Distant homology detection and protein modeling identified a RuvC domain near the CasX C-terminal end, with organization reminiscent of that found in type V CRISPR-Cas systems. The rest of the CasX protein (630 N-terminal amino acids) showed no detectable similarity to any known protein, suggesting this is a novel class 2 effector. The combination of tracrRNA and separate Cas1, Cas2 and Cas4 proteins is unique among type V systems, and phylogenetic analyses indicate that the Cas1 from the CRISPR-CasX system is distant from those of any other known type V. Further, CasX is considerably smaller than any known type V proteins: 980 aa compared to a typical size of about 1,200 amino acids for Cpf1, C2c1 and C2c3 (Burstein, D. et al., 2017 supra).

Another new class 2 Cas protein is encoded in the genomes of certain candidate phyla radiation (CPR) bacteria. This approximately 1,200 amino acid Cas protein, termed CasY, appears to be part of a minimal CRISPR-Cas system that includes Cas1 and a CRISPR array. Most of the CRISPR arrays have unusually short spacers of 17-19 nt, but one system, which lacks Cas1 (CasY.5), has longer spacers (27-29 nt). Accordingly, in some embodiments of the invention, the CasY molecules comprise CasY.1, CasY.2, CasY.3, CasY.4, CasY.5, CasY.6, mutants, variants, analogs or fragments thereof.

In some embodiments, the CRISPR/Cas-like protein can be derived from a wild type Cas protein or fragment thereof. In other embodiments, the CRISPR/Cas-like protein can be derived from modified Cas proteins. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

In some embodiments, the CRISPR-associated endonuclease can be a sequence from another species, for example, other bacterial species, bacteria genomes and archaea, or other prokaryotic microorganisms. Alternatively, the wild type Cas9, CasX, CasY.1, CasY.2, CasY.3, CasY.4, CasY.5, CasY.6, ARMAN 1, ARMAN 4, sequences can be modified. The nucleic acid sequence can be codon optimized for efficient expression in mammalian cells, i.e., "humanized." A humanized Cas9 nuclease sequence can be for example, the Cas9 nuclease sequence encoded by any of the expression vectors listed in GENBANK accession numbers KM099231.1 GI:669193757; KM099232.1 GI:669193761; or KM099233.1 GI:669193765. Alternatively, the Cas9, CasX, CasY.1, CasY.2, CasY.3, CasY.4, CasY.5, CasY.6, ARMAN 1, ARMAN 4, sequences can be for example, the sequence contained within a commercially available vector such as PX330 or PX260 from Addgene (Cambridge, MA). In some embodiments, the Cas9 endonuclease can have an amino acid sequence that is a variant or a fragment of any of the Cas9 endonuclease sequences of GENBANK accession numbers KM099231.1 GI:669193757; KM099232.1 GI:669193761; or KM099233.1 GI:669193765, or Cas9 amino acid sequence of PX330 or PX260 (Addgene, Cambridge, MA).

The wild type Cas9, CasX, CasY.1, CasY.2, CasY.3, CasY.4, CasY.5, CasY.6, ARMAN 1, ARMAN 4, sequences can be a mutated sequence. For example, the Cas9 nuclease can be mutated in the conserved HNH and RuvC domains, which are involved in strand specific cleavage. In another example, an aspartate-to-alanine (D10A) mutation in the RuvC catalytic domain allows the Cas9 nickase mutant (Cas9n) to nick rather than cleave DNA to yield single-stranded breaks, and the subsequent preferential repair through HDR can potentially decrease the frequency of unwanted indel mutations from off-target double-stranded breaks. The sequences of Cas9, CasX, CasY.1, CasY.2, CasY.3, CasY.4, CasY.5, CasY.6, spCas, eSpCas, SpCas9-HF1, SpCas9-HF2, SpCas9-HF3, SpCas9-HF4, ARMAN 1, ARMAN 4, mutants, variants, high-fidelity variants, orthologs, analogs, fragments, or combinations thereof, can be modified to encode biologically active variants, and these variants can have or can include, for example, an amino acid sequence that differs from a wild type by virtue of containing one or more mutations (e.g., an addition, deletion, or substitution mutation or a combination of such mutations). One or more of the substitution mutations can be a substitution (e.g., a conservative amino acid substitution). For example, a biologically active variant of a Cas9, CasX, CasY.1, CasY.2, CasY.3, CasY.4, CasY.5, CasY.6, spCas, eSpCas, SpCas9-HF1, SpCas9-HF2, SpCas9-HF3, SpCas9-HF4, ARMAN 1, ARMAN 4, polypeptides can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to a wild type Cas9, CasX, CasY.1, CasY.2, CasY.3, CasY.4, CasY.5, CasY.6, spCas, eSpCas, SpCas9, ARMAN 1, ARMAN 4 polypeptides. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. The amino acid residues in the Cas9, CasX, CasY.1, CasY.2, CasY.3, CasY.4, CasY.5, CasY.6, spCas, eSpCas, SpCas9-HF1, SpCas9-HF2, SpCas9-HF3, SpCas9-HF4, ARMAN 1, ARMAN 4, amino acid sequence can be non-naturally occurring amino acid residues. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine (2R,3S)-2-amino-3-methylpentanoic acid and L-cyclopentyl glycine (S)-2-amino-2-cyclopentyl acetic acid. For other examples, one can consult textbooks or the worldwide web (a site currently maintained by the California Institute of Technology displays structures of non-natural amino acids that have been successfully incorporated into functional proteins).

Two nucleic acids or the polypeptides they encode may be described as having a certain degree of identity to one another. For example, a Cas9 protein and a biologically active variant thereof may be described as exhibiting a certain degree of identity. Alignments may be assembled by locating short Cas9 sequences in the Protein Information Research (PIR) site (pir.georgetown.edu), followed by analysis with the "short nearly identical sequences" Basic Local Alignment Search Tool (BLAST) algorithm on the NCBI website (ncbi.nlm.nih.gov/blast).

A percent sequence identity to Cas9 can be determined and the identified variants may be utilized as a CRISPR-associated endonuclease and/or assayed for their efficacy as a pharmaceutical composition. A naturally occurring Cas9 can be the query sequence and a fragment of a Cas9 protein can be the subject sequence. Similarly, a fragment of a Cas9 protein can be the query sequence and a biologically active variant thereof can be the subject sequence. To determine sequence identity, a query nucleic acid or amino acid sequence can be aligned to one or more subject nucleic acid or amino acid sequences, respectively, using the computer program ClustalW (version 1.83, default parameters), which allows alignments of nucleic acid or protein sequences to be carried out across their entire length (global alignment). See Chenna et al., *Nucleic Acids Res.* 31:3497-3500, 2003.

The Cas9 nuclease sequence can be a mutated sequence. For example, the Cas9 nuclease can be mutated in the conserved HNH and RuvC domains, which are involved in strand specific cleavage. For example, an aspartate-to-alanine (D10A) mutation in the RuvC catalytic domain allows the Cas9 nickase mutant (Cas9n) to nick rather than cleave DNA to yield single-stranded breaks, and the subsequent preferential repair through HDR can potentially decrease the frequency of unwanted indel mutations from off-target double-stranded breaks.

Guide RNA: A gRNA includes a mature crRNA that contains about 20 base pairs (bp) of unique target sequence (called spacer) and a trans-activated small RNA (tracrRNA) that serves as a guide for ribonuclease III-aided processing of pre-crRNA. The crRNA:tracrRNA duplex directs Cas9 to target DNA via complementary base pairing between the spacer on the crRNA and the complementary sequence (called protospacer) on the target DNA. Cas9 recognizes a trinucleotide (NGG) protospacer adjacent motif (PAM) to specify the cut site (the 3rd nucleotide from PAM). In the present invention, the crRNA and tracrRNA can be expressed separately or engineered into an artificial fusion gRNA via a synthetic stem loop (AGAAAU) to mimic the natural crRNA/tracrRNA duplex. Such gRNA can be synthesized or in vitro transcribed for direct RNA transfection or expressed from U6 or H1-promoted RNA expression vector.

In the compositions of the present invention, each gRNA includes a sequence that is complementary to a target sequence in a retrovirus. The exemplary target retrovirus is HIV, but the compositions of the present invention are also useful for targeting other retroviruses, such as HIV-2 and simian immunodeficiency virus (SIV)-1.

Some of the exemplary gRNAs of the present invention are complimentary to target sequences in the long terminal repeat (LTR) regions of HIV. The LTRs are subdivided into U3, R and U5 regions. LTRs contain all of the required signals for gene expression, and are involved in the integration of a provirus into the genome of a host cell. For example, the basal or core promoter, a core enhancer and a modulatory region is found within U3 while the transactivation response element is found within R. In HIV-1, the U5 region includes several sub-regions, for example, TAR or trans-acting responsive element, which is involved in transcriptional activation; Poly A, which is involved in dimerization and genome packaging; PBS or primer binding site; Psi or the packaging signal; DIS or dimer initiation site.

Accordingly, in some embodiments a gRNA target sequence comprises one or more target sequences in an LTR region of an HIV proviral DNA and one or more targets in a structural gene and/or non-structural gene of the HIV proviral DNA. In other embodiments, a gRNA target sequence comprises one or more target sequences in an LTR region of an HIV proviral DNA and one or more targets in a structural gene. In another embodiment, a gRNA target sequence comprises one or more target sequences in an LTR region of an HIV proviral DNA and one or more targets in a non-structural gene of the HIV proviral DNA. In yet another embodiment, a gRNA target sequence comprises one or more target sequences in an HIV proviral a structural gene and one or more targets in a non-structural gene of the HIV proviral DNA. In yet another embodiment, a gRNA target sequence comprises one or more target sequences in an HIV proviral a non-coding gene and one or more targets in a coding gene of the HIV proviral DNA. In yet another embodiment a gRNA target nucleic acid sequence comprises one or more target nucleic acid sequences in a first gene and one or more target nucleic acid sequences in a second gene; or, one or more target nucleic acid sequences in a first gene and one or more target nucleic acid sequences in a third gene; or, one or more target nucleic acid sequences in a first gene and one or more target nucleic acid sequences in a second gene and one or more target nucleic acid sequences in a third gene; or, one or more target nucleic acid sequences in a second gene and one or more target nucleic acid sequences in a third gene or fourth gene; or, any combinations thereof. As can be seen, any combination of target nucleic acid sequences can be used and are only limited by the imagination of one of ordinary skill in the art.

In certain embodiments, target sequences comprise sequences within the U3, R, and U5 regions of the LTR. In certain embodiments the target sequences comprise one or more sequences from: LTR 1, LTR 2, LTR 3, LTR A, LTR B, LTR B', LTR C, LTR D, LTR E, LTR F, LTR G, LTR H, LTR I, LTR J, LTR K, LTR L, LTR M, LTR N, LTR O, LTR P, LTR Q, LTR R, LTR S, AND LTR T. The compositions of the present invention include these exemplary gRNAs, but are not limited to them, and can include gRNAs complimentary to any suitable target site in the HIV LTRs.

Some of the exemplary gRNAs of the present invention target sequences in the protein coding genome of HIV. Sequences within the gene encoding the structural protein gag were found to be useful target sequences. gRNAs complementary to these target sequences include Gag A, Gag B, Gag C, and Gag D. Useful target sequences were also found within the gene encoding the structural protein pol. gRNAs complementary to these target sequences include Pol A and Pol B.

Examples of guide RNAs are shown in Tables 1-5. Accordingly, the compositions of the present invention include these exemplary gRNAs, but are not limited to them, and can include gRNAs complimentary to any suitable target site in the protein coding genes of HIV, including but not limited to those encoding the structural protein tat, and the accessory proteins vif, nef (negative factor) vpu (Virus protein U), vpr, and tev.

Guide RNA sequences according to the present invention can be sense or anti-sense sequences. The guide RNA sequence generally includes a proto-spacer adjacent motif (PAM). The sequence of the PAM can vary depending upon the specificity requirements of the CRISPR endonuclease used. In the CRISPR-Cas system derived from *S. pyogenes*, the target DNA typically immediately precedes a 5'-NGG proto-spacer adjacent motif (PAM). Thus, for the *S. pyogenes* Cas9, the PAM sequence can be AGG, TGG, CGG or GGG. Other Cas9 orthologs may have different PAM specificities. For example, Cas9 from *S. thermophilus* requires 5'-NNAGAA for CRISPR 1 and 5'-NGGNG for CRISPR3) and Neiseria menigiditis requires 5'-NNNNGATT). The specific sequence of the guide RNA may vary, but, regardless of the sequence, useful guide RNA sequences will be those that minimize off-target effects while achieving high efficiency and complete ablation of the genomically integrated retrovirus, e.g. HIV. The length of the guide RNA sequence can vary from about 20 to about 60 or more nucleotides, for example about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60 or more nucleotides. Useful selection methods identify regions having extremely low homology between the foreign viral genome and host cellular genome including endogenous retroviral DNA, include bioinformatic screening using 12-bp+NGG target-selection criteria to exclude off-target human transcriptome or (even rarely) untranslated-genomic sites; avoiding transcription factor binding sites within the HIV LTR promoter (potentially conserved in the host genome); and WGS, Sanger sequencing and SURVEYOR assay, to identify and exclude potential off-target effects.

The guide RNA sequence can be configured as a single sequence or as a combination of one or more different sequences, e.g., a multiplex configuration. Multiplex configurations can include combinations of two, three, four, five, six, seven, eight, nine, ten, or more different guide RNAs. Combinations of gRNAs are especially effective when expressed in multiplex fashion, that is, simultaneously in the same cell. In many cases, the combinations produced excision of the HIV provirus extending between the target sites. The excisions are attributable to deletions of sequences between the cleavages induced by Cas9 at each of the multiple target sites. These combinations pairs of gRNAs, with one member being complementary to a target site in an LTR of the retrovirus, and the other member being complementary to a gRNA complementary to a target site in a structural gene of the retrovirus. Exemplary effective combinations include Gag D combined with one of LTR 1, LTR 2, LTR 3, LTR A, LTR B, LTR C, LTR D, LTR E, LTR F, LTR G; LTR H, LTR I, LTR J, LTR K, LTR L, LTR M; LTR N, LTR O, LTR P, LTR Q, LTR R, LTR S, or LTR T. Exemplary effective combinations also include LTR 3 combined with one of LTR-1, Gag A; Gag B; Gag C, Gag D, Pol A, or Pol B. In certain embodiments, a gRNA sequence has at least a 75% sequence identity to complementary target nucleic acid sequences encoding T LTR 1, LTR 2, LTR 3, LTR A, LTR B, LTR C, LTR D, LTR E, LTR F, LTR G; LTR H, LTR I, LTR J, LTR K, LTR L, LTR M; LTR N, LTR O, LTR P, LTR Q, LTR R, LTR S, or LTR T. The compositions of present invention are not limited to these combinations, but include any suitable combination of gRNAs complimentary to two or more different target sites in the HIV provirus.

In certain embodiments, a target nucleic acid sequence comprises one or more nucleic acid sequences in coding and non-coding nucleic acid sequences of the retroviral genome. The target nucleic acid sequence can be located within a sequence encoding structural proteins, non-structural proteins or combinations thereof. The sequences encoding structural proteins comprise nucleic acid sequences encoding: Gag, Gag-Pol precursor, Pro (protease), Reverse Transcriptase (RT), integrase (In), Env or combinations thereof. The sequences encoding non-structural proteins comprise nucleic acid sequences encoding: regulatory proteins e.g. Tat, Rev, accessory proteins, e.g. Nef, Vpr, Vpu, Vif or combinations thereof.

In certain embodiments, a gRNA sequence has at least a 75% sequence identity to complementary target nucleic acid sequences encoding Gag, Gag-Pol precursor, Pro, Reverse Transcriptase (RT), integrase (In), Env. Tat, Rev, Nef, Vpr, Vpu, Vif or combinations thereof.

In certain embodiments, a gRNA sequence is complementary to target nucleic acid sequences encoding Gag, Gag-Pol precursor, Pro, Reverse Transcriptase (RT), integrase (In), Env. Tat, Rev, Nef, Vpr, Vpu, Vif or combinations thereof.

In certain embodiments, gRNAs in single and multiplex configurations target the retroviral genome as well as the genes encoding receptors used by the virus to infect a cell, e.g. in the case of HIV, the receptor can be CCR5.

In some embodiments, the one or more isolated nucleic acids sequences are encoded by two or more constructs with one member directed toward a first retroviral target sequence, and the other member toward a second retroviral target sequence excises or eradicates the retroviral genome from an infected cell. Accordingly, the invention features compositions for use in inactivating a proviral DNA integrated into a host cell, including an isolated nucleic acid sequence encoding a CRISPR-associated endonuclease and one or more isolated nucleic acid sequences encoding one or more gRNAs complementary to a target sequence in HIV or another retrovirus. A second isolated nucleic acid sequence encoding a CRISPR-associated endonuclease and one or more isolated nucleic acid sequences encoding one or more gRNAs complementary to a target sequence encoding a receptor used by a virus to infect a cell. The isolated nucleic acid can include one gRNA, two gRNAs, three gRNAs etc. Furthermore, the isolated nucleic acid can include one or more gRNAs complementary to target sequences in the retrovirus and a second isolated nucleic acid can include one or more gRNAs complementary to target sequences encoding receptors used by the virus to infect a cell. Alternatively each isolated nucleic acid can include at least one gRNA complementary to a target virus sequence and at least one a gRNA complementary to target sequences encoding receptors used by the virus to infect a cell. One of ordinary skill in the art would only be limited by their imagination with respect to the various combinations of gRNAs.

Modified or Mutated Nucleic Acid Sequences: In some embodiments, any of the nucleic acid sequences may be modified or derived from a native nucleic acid sequence, for example, by introduction of mutations, deletions, substitutions, modification of nucleobases, backbones and the like. The nucleic acid sequences include the vectors, gene-editing agents, gRNAs, etc. Examples of some modified nucleic acid sequences envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, modified oligonucleotides comprise those with phosphorothioate backbones and those with heteroatom backbones, $CH_2$—NH—O—$CH_2$, CH, —N($CH_3$)—O—$CH_2$ [known as a methylene(methylimino) or MMI backbone], $CH_2$—O—N($CH_3$)—$CH_2$, $CH_2$—N($CH_3$)—N ($CH_3$)—$CH_2$ and O—N($CH_3$)—$CH_2$—$CH_2$ backbones, wherein the native phosphodiester backbone is represented as O—P—O—CH). The amide backbones disclosed by De Mesmaeker et al. *Acc. Chem. Res.* 1995, 28:366-374) are also embodied herein. In some embodiments, the nucleic acid sequences having morpholino backbone structures (Summerton and Weller, U.S. Pat. No. 5,034,506), peptide nucleic acid (PNA) backbone wherein the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497). The nucleic acid sequences may also comprise one or more substituted sugar moieties. The nucleic acid sequences may also have sugar mimetics such as cyclobutyls in place of the pentofuranosyl group.

The nucleic acid sequences may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N^6$ (6-aminohexyl)adenine and 2,6-diaminopurine. Kornberg, A., DNA Replication, W. H. Freeman & Co., San Francisco, 1980, pp 75-77; Gebeyehu, G., et al. *Nucl. Acids Res.* 1987, 15:4513). A "universal" base known in the art, e.g., inosine may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278).

Another modification of the nucleic acid sequences of the invention involves chemically linking to the nucleic acid sequences one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci. USA* 1989, 86, 6553), cholic acid (Manoharan et al. *Boorg. Med. Chem. Let.* 1994, 4, 1053), a thioether, e.g., hexyl-S-tritylthiol (Manoharan et al. *Ann. N.Y. Acad. Sci.* 1992, 660, 306; Manoharan et al. *Boorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651). It is not necessary for all positions in a given nucleic acid sequence to be uniformly modified, and in fact more than one of the aforementioned modifications may be incorporated in a single nucleic acid sequence or even at within a single nucleoside within a nucleic acid sequence.

In some embodiments, the RNA molecules e.g. crRNA, tracrRNA, gRNA are engineered to comprise one or more modified nucleobases. For example, known modifications of RNA molecules can be found, for example, in Genes VI, Chapter 9 ("Interpreting the Genetic Code"), Lewis, ed. (1997, Oxford University Press, New York), and Modification and Editing of RNA, Grosjean and Benne, eds. (1998, ASM Press, Washington DC). Modified RNA components include the following: 2'-O-methylcytidine; N$^4$-methylcytidine; N$^4$-2'-O-dimethylcytidine; N$^4$-acetylcytidine; 5-methylcytidine; 5,2'-O-dimethylcytidine; 5-hydroxymethylcytidine; 5-formylcytidine; 2'-O-methyl-5-formaylcytidine; 3-methylcytidine; 2-thiocytidine; lysidine; 2'-O-methyluridine; 2-thiouridine; 2-thio-2'-O-methyluridine; 3,2'-O-dimethyluridine; 3-(3-amino-3-carboxypropyl)uridine; 4-thiouridine; ribosylthymine; 5,2'-O-dimethyluridine; 5-methyl-2-thiouridine; 5-hydroxyuridine; 5-methoxyuridine; uridine 5-oxyacetic acid; uridine 5-oxyacetic acid methyl ester; 5-carboxymethyluridine; 5-methoxycarbonylmethyluridine; 5-methoxycarbonylmethyl-2'-O-methyluridine; 5-methoxycarbonylmethyl-2'-thiouridine; 5-carbamoylmethyluridine; 5-carbamoylmethyl-2'-O-methyluridine; 5-(carboxyhydroxymethyl)uridine; 5-(carboxyhydroxymethyl) uridinemethyl ester; 5-aminomethyl-2-thiouridine; 5-methylaminomethyluridine; 5-methylaminomethyl-2-thiouridine; 5-methylaminomethyl-2-selenouridine; 5-carboxymethylaminomethyluridine; 5-carboxymethylaminomethyl-2'-O-methyl-uridine; 5-carboxymethylaminomethyl-2-thiouridine; dihydrouridine; dihydroribosylthymine; 2'-methyladenosine; 2-methyladenosine; N$^6$Nmethyladenosine; N$^6$, N$^6$-dimethyladenosine; N$^6$,2'-O-trimethyladenosine; 2 methylthio-N$^6$Nisopentenyladenosine; N$^6$-(cis-hydroxyisopentenyl)adenosine; 2-methylthio-N$^6$-(cis-hydroxyisopentenyl)adenosine; N$^6$-glycinylcarbamoyl)adenosine; N$^6$ threonylcarbamoyl adenosine; N$^6$-methyl-N$^6$-threonylcarbamoyl adenosine; 2-methylthio-N$^6$-methyl-N$^6$-threonylcarbamoyl adenosine; N$^6$-hydroxynorvalylcarbamoyl adenosine; 2-methylthio-N$^6$-hydroxnorvalylcarbamoyl adenosine; 2'-O-ribosyladenosine (phosphate); inosine; 2'O-methyl inosine; 1-methyl inosine; 1,2'-O-dimethyl inosine; 2'-O-methyl guanosine; 1-methyl guanosine; N$^2$-methyl guanosine; N$^2$, N$^2$-dimethyl guanosine; N$^2$, 2'-O-dimethyl guanosine; N$^2$, N$^2$, 2'-O-trimethyl guanosine; 2'-O-ribosyl guanosine (phosphate); 7-methyl guanosine; N$^2$, 7-dimethyl guanosine; N$^2$, N$^2$;7-trimethyl guanosine; wyosine; methyl-wyosine; under-modified hydroxywybutosine; wybutosine; hydroxywybutosine; peroxywybutosine; queuosine; epoxyqueuosine; galactosyl-queuosine; mannosyl-queuosine; 7-cyano-7-deazaguanosine; arachaeosine [also called 7-formamido-7-deazaguanosine]; and 7-aminomethyl-7-deazaguanosine.

The isolated nucleic acid molecules of the present invention can be produced by standard techniques. For example, polymerase chain reaction (PCR) techniques can be used to obtain an isolated nucleic acid containing a nucleotide sequence described herein. Various PCR methods are described in, for example, *PCR Primer: A Laboratory*

*Manual,* Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Recombinant Constructs and Delivery Vehicles

Recombinant constructs are also provided herein and can be used to transform cells in order to express the isolated nucleic acid sequences embodied herein. A recombinant nucleic acid construct comprises promoter operably linked to a regulatory region suitable for expressing at least one tRNA, ribozyme, single guide RNA (sgRNA), gene editing agent or combinations thereof.

It will be appreciated that a number of nucleic acids can encode a polypeptide having a particular amino acid sequence. The degeneracy of the genetic code is well known in the art. For many amino acids, there is more than one nucleotide triplet that serves as the codon for the amino acid. For example, codons in the coding sequence for Cas9 can be modified such that optimal expression in a particular organism is obtained, using appropriate codon bias tables for that organism.

Nucleic acids as described herein may be contained in vectors. Vectors can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). An expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or FLAG™ tag (Kodak, New Haven, CT) sequences typically are expressed as a fusion with the encoded polypeptide. Such tags can be inserted anywhere within the polypeptide, including at either the carboxyl or amino terminus.

Additional expression vectors also can include, for example, segments of chromosomal, non-chromosomal and synthetic DNA sequences. Suitable vectors include derivatives of SV40 and known bacterial plasmids, e.g., *E coli* plasmids col E1, pCR1, pBR322, pMal-C2, pET, pGEX, pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2p plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences.

Several delivery methods may be utilized for in vitro (cell cultures) and in vivo (animals and patients) systems. In one embodiment, a lentiviral gene delivery system may be utilized. Such a system offers stable, long term presence of the gene in dividing and non-dividing cells with broad tropism and the capacity for large DNA inserts. (Dull et al, *J Virol*, 72:8463-8471 1998). In an embodiment, adeno-associated virus (AAV) may be utilized as a delivery method. AAV is a non-pathogenic, single-stranded DNA virus that has been actively employed in recent years for delivering therapeutic gene in in vitro and in vivo systems (Choi et al, *Curr Gene Ther*, 5:299-310, 2005). An example non-viral delivery method may utilize nanoparticle technology. This platform has demonstrated utility as a pharmaceutical in vivo. Nanotechnology has improved transcytosis of drugs across tight epithelial and endothelial barriers. It offers targeted delivery of its payload to cells and tissues in a specific manner (Allen and Cullis, *Science*, 303:1818-1822, 1998).

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, nuclear localization signals, and introns.

The term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Vectors include, for example, viral vectors (such as adenoviruses Ad, AAV, lentivirus, and vesicular stomatitis virus (VSV) and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; *BioTechniques*, 34: 167-171 (2003). A large variety of such vectors is known in the art and are generally available. A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described (see, e.g., Curiel, D T, et al. *PNAS* 88: 8850-8854, 1991).

Additional vectors include viral vectors, fusion proteins and chemical conjugates. Retroviral vectors include Moloney murine leukemia viruses and HIV-based viruses. One HIV based viral vector comprises at least two vectors wherein the gag and pol genes are from an HIV genome and the env gene is from another virus. DNA viral vectors include pox vectors such as orthopox or avipox vectors, herpesvirus vectors such as a herpes simplex I virus (HSV) vector [Geller, A. I. et al., *J. Neurochem*, 64: 487 (1995); Lim, F., et al., in DNA Cloning: Mammalian Systems, D. Glover, Ed. (Oxford Univ. Press, Oxford England) (1995); Geller, A. I. et al., *Proc Natl. Acad. Sci.*: U.S.A.: 90 7603 (1993); Geller, A. I., et al., *Proc Natl. Acad. Sci* USA: 87:1149 (1990)], Adenovirus Vectors [LeGal LaSalle et al., *Science*, 259:988 (1993); Davidson, et al., *Nat. Genet.* 3: 219 (1993); Yang, et al., *J. Virol.* 69: 2004 (1995)] and Adeno-associated Virus Vectors [Kaplitt, M. G., et al., *Nat. Genet.* 8:148 (1994)].

The polynucleotides disclosed herein may be used with a microdelivery vehicle such as cationic liposomes and adenoviral vectors. For a review of the procedures for liposome preparation, targeting and delivery of contents, see Mannino and Gould-Fogerite, *BioTechniques*, 6:682 (1988). See also, Felgner and Holm, *Bethesda Res. Lab. Focus*, 11(2):21 (1989) and Maurer, R. A., *Bethesda Res. Lab. Focus*, 11(2): 25 (1989).

Replication-defective recombinant adenoviral vectors, can be produced in accordance with known techniques. See, Quantin, et al., *Proc. Natl. Acad. Sci.* USA, 89:2581-2584 (1992); Stratford-Perricadet, et al., *J. Clin. Invest.*, 90:626-630 (1992); and Rosenfeld, et al., *Cell*, 68:143-155 (1992).

Another delivery method is to use single stranded DNA producing vectors which can produce the expressed products intracellularly. See for example, Chen et al, *BioTechniques*, 34: 167-171 (2003), which is incorporated herein, by reference, in its entirety.

The polynucleotides disclosed herein may be used with a microdelivery vehicle such as cationic liposomes and adenoviral vectors. For a review of the procedures for liposome preparation, targeting and delivery of contents, see Mannino and Gould-Fogerite, *BioTechniques*, 6:682 (1988). See also, Felgner and Holm, *Bethesda Res. Lab. Focus,* 11(2):21 (1989) and Maurer, R. A., *Bethesda Res. Lab. Focus,* 11(2): 25 (1989).

In certain embodiments of the invention, non-viral vectors may be used to effectuate transfection. Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam and Lipofectin). Cationic and neutral lipids that are suitable for efficient receptor-recognition lipofection of polynucleotides include those described in U.S. Pat. No. 7,166,298 to Jessee or U.S. Pat. No. 6,890,554 to Jesse, the contents of each of which are incorporated by reference. Delivery can be to cells (e.g. in vitro or ex vivo administration) or target tissues (e.g. in vivo administration).

Synthetic vectors are typically based on cationic lipids or polymers which can complex with negatively charged nucleic acids to form particles with a diameter in the order of 100 nm. The complex protects nucleic acid from degradation by nuclease. Moreover, cellular and local delivery strategies have to deal with the need for internalization, release, and distribution in the proper subcellular compartment. Systemic delivery strategies encounter additional hurdles, for example, strong interaction of cationic delivery vehicles with blood components, uptake by the reticuloendothelial system, kidney filtration, toxicity and targeting ability of the carriers to the cells of interest. Modifying the surfaces of the cationic non-virals can minimize their interaction with blood components, reduce reticuloendothelial system uptake, decrease their toxicity and increase their binding affinity with the target cells. Binding of plasma proteins (also termed opsonization) is the primary mechanism for RES to recognize the circulating nanoparticles. For example, macrophages, such as the Kupffer cells in the liver, recognize the opsonized nanoparticles via the scavenger receptor.

The anti-retroviral agents and/or the isolated nucleic acid sequences of the invention can be delivered to an appropriate cell of a subject. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm). Another way to achieve uptake of the nucleic acid is using liposomes, prepared by standard methods. The nucleic acids can be incorporated alone into these delivery vehicles or co-incorporated with tissue-specific antibodies, for example antibodies that target cell types that are commonly latently infected reservoirs of HIV infections. Alternatively, one can prepare a molecular complex composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression. In the relevant polynucleotides (e.g., expression vectors) the nucleic acid sequence encoding an isolated nucleic acid sequence comprising a sequence encoding CRISPR/Cas and/or a guide RNA complementary to a target sequence of HIV, as described above.

In some embodiments, the compositions of the invention can be formulated as a nanoparticle, for example, nanoparticles comprised of a core of high molecular weight linear polyethylenimine (LPEI) complexed with DNA and surrounded by a shell of polyethyleneglycol modified (PEGylated) low molecular weight LPEI. In some embodiments, the compositions can be formulated as a nanoparticle encapsulating the compositions embodied herein. L-PEI has been used to efficiently deliver genes in vivo into a wide range of organs such as lung, brain, pancreas, retina, bladder as well as tumor. L-PEI is able to efficiently condense, stabilize and deliver nucleic acids in vitro and in vivo.

In some embodiments, delivery of vectors can also be mediated by exosomes. Exosomes are lipid nanovesicles released by many cell types. They mediate intercellular communication by transporting nucleic acids and proteins between cells. Exosomes contain RNAs, miRNAs, and proteins derived from the endocytic pathway. They may be taken up by target cells by endocytosis, fusion, or both. Exosomes can be harnessed to deliver nucleic acids to specific target cells.

The expression constructs of the present invention can also be delivered by means of nanoclews. Nanoclews are a cocoon-like DNA nanocomposites (Sun, et al., *J. Am. Chem. Soc.* 2014, 136:14722-14725). They can be loaded with nucleic acids for uptake by target cells and release in target cell cytoplasm. Methods for constructing nanoclews, loading them, and designing release molecules can be found in Sun, et al. (Sun W, et al., *J. Am. Chem. Soc.* 2014, 136: 14722-14725; Sun W, et al., *Angew. Chem. Int.* Ed. 2015: 12029-12033.)

The nucleic acids and vectors may also be applied to a surface of a device (e.g., a catheter) or contained within a pump, patch, or any other drug delivery device. The nucleic acids and vectors disclosed herein can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary).

In some embodiments of the invention, liposomes are used to effectuate transfection into a cell or tissue. The pharmacology of a liposomal formulation of nucleic acid is largely determined by the extent to which the nucleic acid is encapsulated inside the liposome bilayer. Encapsulated nucleic acid is protected from nuclease degradation, while those merely associated with the surface of the liposome is not protected. Encapsulated nucleic acid shares the extended circulation lifetime and biodistribution of the intact liposome, while those that are surface associated adopt the pharmacology of naked nucleic acid once they disassociate from the liposome. Nucleic acids may be entrapped within liposomes with conventional passive loading technologies, such as ethanol drop method (as in SALP), reverse-phase evaporation method, and ethanol dilution method (as in SNALP).

Liposomal delivery systems provide stable formulation, provide improved pharmacokinetics, and a degree of 'passive' or 'physiological' targeting to tissues. Encapsulation of hydrophilic and hydrophobic materials, such as potential chemotherapy agents, are known. See for example U.S. Pat. No. 5,466,468 to Schneider, which discloses parenterally administrable liposome formulation comprising synthetic lipids; U.S. Pat. No. 5,580,571, to Hostetler et al. which discloses nucleoside analogues conjugated to phospholipids; U.S. Pat. No. 5,626,869 to Nyqvist, which discloses pharmaceutical compositions wherein the pharmaceutically active compound is heparin or a fragment thereof contained in a defined lipid system comprising at least one amphiphatic and polar lipid component and at least one nonpolar lipid component.

Liposomes and polymerosomes can contain a plurality of solutions and compounds. In certain embodiments, the complexes of the invention are coupled to or encapsulated in polymersomes. As a class of artificial vesicles, polymersomes are tiny hollow spheres that enclose a solution, made using amphiphilic synthetic block copolymers to form the vesicle membrane. Common polymersomes contain an aqueous solution in their core and are useful for encapsulating and protecting sensitive molecules, such as drugs, enzymes, other proteins and peptides, and DNA and RNA fragments. The polymersome membrane provides a physical barrier that isolates the encapsulated material from external materials, such as those found in biological systems. Polymerosomes can be generated from double emulsions by known techniques, see Lorenceau et al., 2005, Generation of Polymerosomes from Double-Emulsions, *Langmuir* 21(20): 9183-6.

In some embodiments of the invention, non-viral vectors are modified to effectuate targeted delivery and transfection. PEGylation (i.e. modifying the surface with polyethyleneglycol) is the predominant method used to reduce the opsonization and aggregation of non-viral vectors and minimize the clearance by reticuloendothelial system, leading to a prolonged circulation lifetime after intravenous (i.v.) administration. PEGylated nanoparticles are therefore often referred as "stealth" nanoparticles. The nanoparticles that are not rapidly cleared from the circulation will have a chance to encounter infected cells.

In some embodiments of the invention, targeted controlled-release systems responding to the unique environments of tissues and external stimuli are utilized. Gold nanorods have strong absorption bands in the near-infrared region, and the absorbed light energy is then converted into heat by gold nanorods, the so-called "photothermal effect". Because the near-infrared light can penetrate deeply into tissues, the surface of gold nanorod could be modified with nucleic acids for controlled release. When the modified gold nanorods are irradiated by near-infrared light, nucleic acids are released due to thermo-denaturation induced by the photothermal effect. The amount of nucleic acids released is dependent upon the power and exposure time of light irradiation.

Regardless of whether compositions are administered as nucleic acids or polypeptides, they are formulated in such a way as to promote uptake by the mammalian cell. Useful vector systems and formulations are described above. In some embodiments the vector can deliver the compositions to a specific cell type. The invention is not so limited however, and other methods of DNA delivery such as chemical transfection, using, for example calcium phosphate, DEAE dextran, liposomes, lipoplexes, surfactants, and perfluoro chemical liquids are also contemplated, as are physical delivery methods, such as electroporation, micro injection, ballistic particles, and "gene gun" systems.

In other embodiments, the compositions comprise a cell which has been transformed or transfected with one or more vectors encoding the isolated nucleic acids embodied herein. In some embodiments, the methods of the invention can be applied ex vivo. That is, a subject's cells can be removed from the body and treated with the compositions in culture to excise, and the treated cells returned to the subject's body. The cell can be the subject's cells or they can be haplotype matched or a cell line. The cells can be irradiated to prevent replication. In some embodiments, the cells are human leukocyte antigen (HLA)-matched, autologous, cell lines, or combinations thereof. In other embodiments the cells can be a stem cell. For example, an embryonic stem cell or an artificial pluripotent stem cell (induced pluripotent stem cell (iPS cell)). Embryonic stem cells (ES cells) and artificial pluripotent stem cells (induced pluripotent stem cell, iPS cells) have been established from many animal species, including humans. These types of pluripotent stem cells would be the most useful source of cells for regenerative medicine because these cells are capable of differentiation into almost all of the organs by appropriate induction of their differentiation, with retaining their ability of actively dividing while maintaining their pluripotency. iPS cells, in particular, can be established from self-derived somatic cells, and therefore are not likely to cause ethical and social issues, in comparison with ES cells which are produced by destruction of embryos. Further, iPS cells, which are self-derived cell, make it possible to avoid rejection reactions, which are the biggest obstacle to regenerative medicine or transplantation therapy.

Transduced cells are prepared for reinfusion according to established methods. After a period of about 2-4 weeks in culture, the cells may number between $1 \times 10^6$ and $1 \times 10^{10}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent. For administration, cells of the present invention can be administered at a rate determined by the $LD_{50}$ of the cell type, and the side effects of the cell type at various concentrations, as applied to the mass and overall health of the patient. Administration can be accomplished via single or divided doses. Adult stem cells may also be mobilized using exogenously administered factors that stimulate their production and egress from tissues or spaces that may include, but are not restricted to, bone marrow or adipose tissues.

Combination or Alternation Therapy

Accordingly, the invention features compositions which include therapeutically effective amounts of at least one antiretroviral agent administered sequentially or alternately or in conjunction with a composition for inactivating a proviral DNA integrated into a host cell. This composition comprises an isolated nucleic acid sequence encoding a CRISPR-associated endonuclease and one or more isolated nucleic acid sequences encoding one or more gRNAs complementary to a target sequence in HIV or another retrovirus.

In one embodiment, the antiretroviral agent comprises viral entry inhibitors, reverse transcriptase inhibitors, protease inhibitors, and immune-based therapeutic agents.

For example, when used to treat or prevent HIV infection, the antiretroviral agent or its prodrug or pharmaceutically acceptable salt can be administered in combination or alternation with another anti-HIV agent and/or a gene-editing agent embodied herein. In general, in combination therapy, effective dosages of two or more agents are administered together, whereas during alternation therapy, an effective dosage of each agent is administered serially. The dosage will depend on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Combination therapy may be administered as (a) a single pharmaceutical composition which comprises an antiretroviral agent as described herein, at least one gene editing agent as described herein, and a pharmaceutically acceptable excipient, diluent, or carrier; or (b) two separate pharmaceutical compositions comprising (i) a first composition comprising an anti-retroviral agent as embodied herein and a pharmaceutically acceptable excipient, diluent, or carrier; and (ii) a second composition comprising at least one gene editing agents as embodied herein. The pharmaceutical compositions can be administered simultaneously or sequentially and in any order.

In use in treating or preventing viral disease, the antiretroviral(s) can be administered together with at least one gene editing agent as part of a unitary pharmaceutical composition. Alternatively, each can be administered apart from the other antiviral agents. In this embodiment, the antiretroviral(s) and the at least one at least one gene editing agent are administered substantially simultaneously, i.e. the compounds are administered at the same time or one after the other, so long as the compounds reach therapeutic levels for a period of time in the blood. In other embodiments, the antiretroviral agents are administered in one or more doses over a period of time followed by administration of the gene editing agents embodied herein.

The antiretroviral agents may be a nucleoside reverse transcriptase inhibitor, a nucleotide reverse transcriptase inhibitor, a non-nucleoside reverse transcriptase inhibitor, a protease inhibitor, an integrase inhibitor, a fusion inhibitor, a maturation inhibitor, or a combination thereof.

In certain embodiments, the at least one antiretroviral agent comprises: myristolyated dolutegravir, lamivudine, abacavir, rilpivirine or combinations thereof.

In certain embodiments, a composition comprises a therapeutically effective amount of a non-nucleoside reverse transcriptase inhibitor (NNRTI) and/or a nucleoside reverse transcriptase inhibitor (NRTI), and/or myristolyated dolutegravir, lamivudine, abacavir, rilpivirine analogs, variants or combinations thereof. In certain embodiments, an NNRTI comprises: etravirine, efavirenz, nevirapine, rilpivirine, delavirdine, or nevirapine. In embodiments, an NRTI comprises: lamivudine, zidovudine, emtricitabine, abacavir, zalcitabine, dideoxycytidine, azidothymidine, tenofovir disoproxil fumarate, didanosine (ddI EC), dideoxyinosine, stavudine, abacavir sulfate or combinations thereof.

Examples of nucleoside reverse transcriptase inhibitors include zidovudine, didanosine, stavudine, zalcitabine, abacivir, emtricitabine, and lamivudine. Examples of non-nucleoside reverse transcriptase inhibitors include efavirenz, nevirapine, and delaviradine. Examples of protease inhibitors include indinavir, ritonavir, saquinavir, lopinavir, and nelfinavir. Examples of a reverse transcriptase inhibitor, an integrase inhibitor, a fusion inhibitor, and a maturation inhibitor are tenofovir, raltegravir, mariviroc, and bevirimat, respectively. In some aspects, the antiretroviral agents present in a nanoparticle include, ritonavir, lopinavir, and efavirenz, or efavirenz, abacavir, and lamivudine, or emtricitabine, tenofovir, and raltegravir.

In certain embodiments, the composition further comprises at least one or more protease inhibitors. In certain embodiments, a protease inhibitor comprises: amprenavir, tipranavir, indinavir, saquinavir mesylate, lopinavir and ritonavir (LPV/RTV), Fosamprenavir Calcium (FOS-APV), ritonavir, darunavir, atazanavir sulfate, nelfinavir mesylate or combinations thereof.

In certain embodiments, the compositions comprise an anti-retroviral agent, used in HAART, chemotherapeutic agents, activators of HIV transcription, e.g. PMA, TSA, and the like. Antiretroviral agents may include reverse transcriptase inhibitors (e.g., nucleoside/nucleotide reverse transcriptase inhibitors, zidovudine, emtricitibine, lamivudine and tenoifvir; and non-nucleoside reverse transcriptase inhibitors such as efavarenz, nevirapine, rilpivirine); protease inhibitors, e.g., tipiravir, darunavir, indinavir; entry inhibitors, e.g., maraviroc; fusion inhibitors, e.g., enfuvirtide; or integrase inhibitors e.g., raltegrivir, dolutegravir. Antiretroviral agents may also include multi-class combination agents for example, combinations of emtricitabine, efavarenz, and tenofivir; combinations of emtricitabine; rilpivirine, and tenofivir; or combinations of elvitegravir, cobicistat, emtricitabine and tenofivir.

In addition, one or more agents which alleviate any other symptoms that may be associated with the virus infection, e.g. fever, chills, headaches, secondary infections, can be administered in concert with, or as part of the pharmaceutical composition or at separate times. These agents comprise, without limitation, an anti-pyretic agent, anti-inflammatory agent, chemotherapeutic agent, or combinations thereof.

Some antiviral agents which can be used for combination therapy include agents that interfere with the ability of a virus to infiltrate a target cell. The virus must go through a sequence of steps to do this, beginning with binding to a specific "receptor" molecule on the surface of the host cell and ending with the virus "uncoating" inside the cell and releasing its contents. Viruses that have a lipid envelope must also fuse their envelope with the target cell, or with a vesicle that transports them into the cell, before they can uncoat.

There are two types of active agents which inhibit this stage of viral replication. One type includes agents which mimic the virus-associated protein (VAP) and bind to the cellular receptors, including VAP anti-idiotypic antibodies, natural ligands of the receptor and anti-receptor antibodies, receptor anti-idiotypic antibodies, extraneous receptor and synthetic receptor mimics. The other type includes agents which inhibit viral entry, for example, when the virus attaches to and enters the host cell. For example, a number of "entry-inhibiting" or "entry-blocking" drugs are being developed to fight HIV, which targets the immune system white blood cells known as "helper T cells", and identifies these target cells through T-cell surface receptors designated "CRX4" and "CCR5". Thus, CRX4 and CCR5 receptor inhibitors such as amantadine and rimantadine, can be used to inhibit viral infection, such as HIV.

Further antiviral agents that can be used in combination with the gene-editing agents embodied herein include agents which interfere with viral processes that synthesize virus components after a virus invades a cell. Representative agents include nucleotide and nucleoside analogues that look like the building blocks of RNA or DNA, but deactivate the enzymes that synthesize the RNA or DNA once the analogue is incorporated. Acyclovir is a nucleoside analogue, and is effective against herpes virus infections. Zidovudine (AZT), 3TC, FTC, and other nucleoside reverse transcriptase inhibitors (NRTI), as well as non-nucleoside reverse transcriptase inhibitors (NNRTI), can also be used. Integrase inhibitors can also be used.

Once a virus genome becomes operational in a host cell, it then generates messenger RNA (mRNA) molecules that direct the synthesis of viral proteins. Production of mRNA is initiated by proteins known as transcription factors, and certain active agents block attachment of transcription factors to viral DNA.

Other active agents include antisense oligonucleotides and ribozymes (enzymes which cut apart viral RNA or DNA at selected sites). HIV include protease enzymes, which cut viral protein chains apart so they can be assembled into their final configuration. Protease inhibitors are another type of antiviral agent that can be used in combination with the inhibitory compounds described herein. The final stage in the life cycle of a virus is the release of completed viruses from the host cell.

Still other active agents function by stimulating the patient's immune system. Interferons, including pegylated interferons, are representative compounds of this class.

In certain embodiments, the anti-viral or antiretroviral agent comprises therapeutically effective amounts of: antibodies, aptamers, adjuvants, anti-sense oligonucleotides, chemokines, cytokines, immune stimulating agents, immune modulating molecules, B-cell modulators, T-cell modulators, NK cell modulators, antigen presenting cell modulators, enzymes, siRNA's, interferon, ribavirin, protease inhibitors, anti-sense oligonucleotides, helicase inhibitors, polymerase inhibitors, helicase inhibitors, neuraminidase inhibitors, nucleoside reverse transcriptase inhibitors, non-nucleoside reverse transcriptase inhibitors, purine nucleosides, chemokine receptor antagonists, interleukins, vaccines or combinations thereof.

The immune-modulating molecules comprise, but are not limited to cytokines, lymphokines, T cell co-stimulatory ligands, etc. An immune-modulating molecule positively and/or negatively influences the humoral and/or cellular immune system, particularly its cellular and/or non-cellular components, its functions, and/or its interactions with other physiological systems. The immune-modulating molecule may be selected from the group comprising cytokines, chemokines, macrophage migration inhibitory factor (MIF; as described, inter alia, in Bernhagen (1998), *Mol Med* 76(3-4); 151-61 or Metz (1997), *Adv Immunol* 66, 197-223), T-cell receptors or soluble MHC molecules. Such immune-modulating effector molecules are well known in the art and are described, inter alia, in Paul, "Fundamental immunology", Raven Press, New York (1989). In particular, known cytokines and chemokines are described in Meager, "The Molecular Biology of Cytokines" (1998), John Wiley & Sons, Ltd., Chichester, West Sussex, England; (Bacon (1998). Cytokine Growth Factor Rev 9(2):167-73; Oppenheim (1997). *Clin Cancer Res* 12, 2682-6; Taub, (1994) *Ther. Immunol.* 1(4), 229-46 or Michiel, (1992). *Semin Cancer Biol* 3(1), 3-15).

Immune cell activity that may be measured include, but is not limited to, (1) cell proliferation by measuring the DNA replication; (2) enhanced cytokine production, including specific measurements for cytokines, such as IFN-γ, GM-CSF, or TNF-α; (3) cell mediated target killing or lysis; (4) cell differentiation; (5) immunoglobulin production; (6) phenotypic changes; (7) production of chemotactic factors or chemotaxis, meaning the ability to respond to a chemotactin with chemotaxis; (8) immunosuppression, by inhibition of the activity of some other immune cell type; and, (9) apoptosis, which refers to fragmentation of activated immune cells under certain circumstances, as an indication of abnormal activation.

Also of interest are enzymes present in the lytic package that cytotoxic T lymphocytes or LAK cells deliver to their targets. Perforin, a pore-forming protein, and Fas ligand are major cytolytic molecules in these cells (Brandau et al., *Clin. Cancer Res.* 6:3729, 2000; Cruz et al., *Br. J. Cancer* 81:881, 1999). CTLs also express a family of at least 11 serine proteases termed granzymes, which have four primary substrate specificities (Kam et al., *Biochim. Biophys. Acta* 1477:307, 2000). Low concentrations of streptolysin O and pneumolysin facilitate granzyme B-dependent apoptosis (Browne et al., *Mol. Cell Biol.* 19:8604, 1999).

Other suitable effectors encode polypeptides having activity that is not itself toxic to a cell, but renders the cell sensitive to an otherwise nontoxic compound—either by metabolically altering the cell, or by changing a non-toxic prodrug into a lethal drug. Exemplary is thymidine kinase (tk), such as may be derived from a herpes simplex virus, and catalytically equivalent variants. The HSV tk converts the anti-herpetic agent ganciclovir (GCV) to a toxic product that interferes with DNA replication in proliferating cells.

Any of the above-mentioned compounds can be used in combination therapy with the gene editing agents embodied herein. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks. The therapeutic agents may be administered under a metronomic regimen, e.g., continuous low-doses of a therapeutic agent.

The compositions described herein are suitable for use in a variety of drug delivery systems described above. Additionally, in order to enhance the in vivo serum half-life of the administered compound, the compositions may be encapsulated, introduced into the lumen of liposomes, prepared as a colloid, or other conventional techniques may be employed which provide an extended serum half-life of the compositions. A variety of methods are available for preparing liposomes, as described in, e.g., Szoka, et al., U.S. Pat. Nos. 4,235,871, 4,501,728 and 4,837,028 each of which is incorporated herein by reference. Furthermore, one may administer the drug in a targeted drug delivery system, for example, in a liposome coated with a tissue specific antibody. The liposomes will be targeted to and taken up selectively by the organ.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating viral infections, an effective amount of the inhibitory compound is an amount sufficient to suppress the growth and proliferation of the virus. Viral infections can be prevented, either initially, or from re-occurring, by administering the compounds described herein in a prophylactic manner. Preferably, the effective amount is sufficient to obtain the desired result, but insufficient to cause appreciable side effects.

Dosage, toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage for use in humans. The dosage of such compositions lies preferably within a range of circulating concentrations that include the $ED_{50}$ with little or no toxicity. The dosage may vary within this range depending upon the dosage form employed and the route of administration utilized. For any composition used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As described, a therapeutically effective amount of a composition (i.e., an effective dosage) means an amount sufficient to produce a therapeutically (e.g., clinically) desirable result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

The effective dose can vary, depending upon factors such as the condition of the patient, the severity of the viral infection, and the manner in which the pharmaceutical composition is administered. The effective dose of compounds will of course differ from patient to patient, but in general includes amounts starting where desired therapeutic effects occur but below the amount where significant side effects are observed. For human patients, the effective dose of typical compounds generally requires administering the compound in an amount of at least about 1, often at least about 10, and frequently at least about 25 µg/24 hr/patient. The effective dose generally does not exceed about 500, often does not exceed about 400, and frequently does not exceed about 300 µg/24 hr/patient. In addition, administration of the effective dose is such that the concentration of the compound within the plasma of the patient normally does not exceed 500 ng/mL and frequently does not exceed 100 ng/mL.

The compounds, when employed in effective amounts in accordance with the method described herein, are effective at eliminating the retrovirus from the subject.

In some embodiments, the compositions may be formulated as a topical gel, for example, to treat a melanoma after excision, or an autoimmune condition expressed as a skin condition e.g. pemphigus. In some embodiments, the compositions can be formulated as a nanoparticle encapsulating a nucleic acid.

A subject is effectively treated whenever a clinically beneficial result ensues. This may mean, for example, a complete resolution of the symptoms of a disease, a decrease in the severity of the symptoms of the disease, or a slowing of the disease's progression. These methods can further include the steps of a) identifying a subject (e.g., a patient and, more specifically, a human patient) who has a certain disease to be treated; and b) providing to the subject the compositions comprising at least one anti-viral or anti-retroviral agent and/or a composition comprising the gene editing agents embodied herein.

In methods of treatment of HIV-1 infection, a subject can be identified using standard clinical tests, for example, immunoassays to detect the presence of HIV antibodies or the HIV polypeptide p24 in the subject's serum, or through HIV nucleic acid amplification assays. An amount of such a composition provided to the subject that results in a complete resolution of the symptoms of the infection, a decrease in the severity of the symptoms of the infection, or a slowing of the infection's progression is considered a therapeutically effective amount. The present methods may also include a monitoring step to help optimize dosing and scheduling as well as predict outcome. In some methods of the present invention, one can first determine whether a patient has a latent HIV infection, and then make a determination as to whether or not to treat the patient with one or more of the compositions described herein. In some embodiments, the methods can further include the step of determining the nucleic acid sequence of the particular HIV harbored by the patient and then designing the guide RNA to be complementary to those particular sequences. For example, one can determine the nucleic acid sequence of a subject's LTR U3, R or U5 region, or pol, gag, or env genes etc., and then design or select one or more gRNAs to be precisely complementary to the patient's sequences. The novel gRNAs provided by the present invention greatly enhance the chances of formulating an effective treatment. The gRNAs targeted to nucleic acid sequences encoding a receptor used by a virus to infect a cell would prevent further infection.

In methods of reducing the risk of HIV infection, a subject at risk for having an HIV infection can be, for example, any sexually active individual engaging in unprotected sex, i.e., engaging in sexual activity without the use of a condom; a sexually active individual having another sexually transmitted infection; an intravenous drug user; or an uncircumcised man. A subject at risk for having an HIV infection can be, for example, an individual whose occupation may bring him or her into contact with HIV-infected populations, e.g., healthcare workers or first responders. A subject at risk for having an HIV infection can be, for example, an inmate in a correctional setting or a sex worker, that is, an individual who uses sexual activity for income employment or non-monetary items such as food, drugs, or shelter.

The methods disclosed herein can be applied to a wide range of species, e.g., humans, non-human primates (e.g., monkeys), horses or other livestock, dogs, cats, ferrets or other mammals kept as pets, rats, mice, or other laboratory animals.

The methods of the invention can be expressed in terms of the preparation of a medicament. Accordingly, the invention encompasses the use of the agents and compositions described herein in the preparation of a medicament. The compounds described herein are useful in therapeutic compositions and regimens or for the manufacture of a medicament for use in treatment of diseases or conditions as described herein.

Any composition described herein can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

The dosage required will depend on the route of administration, the nature of the formulation, the nature of the patient's illness, the patient's size, weight, surface area, age, and sex, other drugs being administered, and the judgment of the attending clinicians. Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the compounds in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, a compound can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present compounds can be administered once (or twice, three times, etc.) daily, weekly, monthly, or yearly.

An effective amount of any composition provided herein can be administered to an individual in need of treatment. An effective amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

Any method known to those in the art can be used to determine if a particular response is induced. Clinical methods that can assess the degree of a particular disease state can be used to determine if a response is induced. The particular methods used to evaluate a response will depend upon the nature of the patient's disorder, the patient's age, and sex, other drugs being administered, and the judgment of the attending clinician.

Kits

The compositions described herein can be packaged in suitable containers labeled, for example, for use as a therapy to treat a subject having a viral infection, for example, an HIV infection or a subject at risk of contracting for example, an HIV infection. The containers can include a composition comprising at least one anti-viral or anti-retroviral agent, a gene-editing agent and one or more of a suitable stabilizer, carrier molecule, flavoring, and/or the like, as appropriate for the intended use. In other embodiments, the kit further comprises one or more therapeutic reagents that alleviate some of the symptoms or secondary bacterial infections that may be associated with an HIV infection. Accordingly, packaged products (e.g., sterile containers containing one or more of the compositions described herein and packaged for storage, shipment, or sale at concentrated or ready-to-use concentrations) and kits, including at least one composition of the invention, and instructions for use, are also within the scope of the invention. A product can include a container (e.g., a vial, jar, bottle, bag, or the like) containing one or more compositions of the invention. In addition, an article of manufacture further may include, for example, packaging materials, instructions for use, syringes, delivery devices, buffers or other control reagents for treating or monitoring the condition for which prophylaxis or treatment is required.

The product may also include a legend (e.g., a printed label or insert or other medium describing the product's use (e.g., an audio- or videotape)). The legend can be associated with the container (e.g., affixed to the container) and can describe the manner in which the compositions therein should be administered (e.g., the frequency and route of administration), indications therefor, and other uses. The compositions can be ready for administration (e.g., present in dose-appropriate units), and may include one or more additional pharmaceutically acceptable adjuvants, carriers or other diluents and/or an additional therapeutic agent. Alternatively, the compositions can be provided in a concentrated form with a diluent and instructions for dilution.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, applicants do not admit any particular reference is "prior art" to their invention.

EXAMPLES

Example 1: Combination of CRISPR-Cas9 and
Long-Acting Antiretroviral Therapy Eliminates
HIV-1 Infection in Humanized Mice A cure of HIV-1 infection has been stalled by the absence of a strategy for effective eradication of HIV-1 from the infected tissues and cells serving as viral reservoirs. As such, rebound uniformly occurs after cessation of currently used antiretroviral therapy, ART, that potently controls viral replication but does not eliminate proviral DNA.

Materials and Methods

Cell culture: TZM-bl reporter cell line (AIDS Reagent Program, Division of AIDS, NIAID, NIH, Bethesda, MD)

and HEK-293T cells were cultured in DMEM high glucose complemented with 10% FBS and gentamicin (10 μg/ml). Jurkat, Clone E6 cells were purchased from ATCC (TIB-152™) and were cultured in RPMI medium containing 10% FBS and gentamicin (10 ug/ml). Patient blood samples were obtained through the Comprehensive NeuroAIDS Center (CNAC) Clinical Core (Temple University, Philadelphia, PA, USA). PBMCs were isolated from human peripheral blood by density gradient centrifugation using Ficoll-Paque reagent. Blood sample volume was adjusted to 30 ml with HBSS buffer, gently layered on 15 ml of Ficoll-Paque cushion and centrifuged for 30 minutes at 1500 RPM. PBMCs containing layer was collected, washed 3 times in HBSS buffer and counted. Cells were incubated with PHA (5 μg/ml) for 24 h and then cultured in RPMI with 10% FBS and gentamicin (10 ug/ml) supplemented with human rIL-2 at a concentration of 30 ng/ml (STEMCELL Tech.). Fresh media was added every 2-3 days.

In vitro infection: HEK-293T cells were transfected using $CaPO_4$ precipitation method in the presence of chloroquine (50 uM) with 30 μg of $pNL_{4-3}$-EGFP-P2A-Nef plasmid (13)/$2.5 \times 10^6$ cells/100 mm dish. Next day, medium was replaced; and 24 h and 48 h later supernatants were collected, clarified at 3000 RPM for 10 minutes, filtered through 0.45 um filter, and concentrated by ultracentrifugation for 2 h with 20% sucrose cushion (25). Viral pellets were resuspended in HBSS by gentle agitation overnight, aliquoted, and tittered in Jurkat cells by FACS for GFP expression. Jurkat cells were infected by spinoculation for 1.5 h (26), 32° C. in 500 μl inoculum containing 8 μg/ml polybrene then resuspended and left for 4 h then 500 μl of growth medium was added. Next day, cells were washed 3 times with PBS and re-suspended in growth medium.

Generation of humanized NSG mice: NOD/scid-IL-2Rγc$^{null}$ (NSG) mice were obtained from the Jackson Laboratories, Bar Harbor, ME and bred under specific pathogen-free conditions in accordance with the ethical guidelines for care of laboratory animals at the University of Nebraska Medical Center (UNMC) set forth by the National Institutes of Health. CD34$^+$ cells were obtained from human cord blood and enriched using immune-magnetic beads (CD34$^+$ selection kit; Miltenyi Biotec Inc., Auburn, CA, USA). CD34$^+$ cell purity was >90% by flow cytometry. Cells were transplanted into newborn mice irradiated at 1 Gy using a C9 cobalt 60 source (Picker Corporation, Cleveland, OH, USA). Cell suspension was delivered by intrahepatic (i.h.) injection of $10^4$ cells/mouse in 20 μl phosphate-buffered saline (PBS) with a 30-gauge needle. Humanization of the animals was affirmed by flow cytometry (21, 27) for CD45 and CD3 staining of blood immune cells shown in FIGS. 8A, 8B.

Drugs and antibodies: Dolutegravir (DTG), lamivudine (3TC), and abacavir (ABC) were generous gifts from ViiV Healthcare, Research Triangle Park, NC. Rilpivirine (RPV) was purchased from Hangzhou Bingo Chemical Co., Ltd, Hangzhou, China. Poloxamer 407 (P407), HEPES buffer, ciprofloxacin, paraformaldehyde (PFA), and 3,3'-diamino-benzidine (DAB) were purchased from Sigma-Aldrich, St. Louis, MO. Diethyl ether, endotoxin-free water, gentamicin, acetonitrile (ACN), methanol, $KH_2PO_4$, bovine serum albumin (BSA), Triton X-100, LC-MS-grade water, and TRIzol reagent were purchased from Fisher Scientific, Hampton, NH, USA. FITC-conjugated mouse anti-human CD45, Alexa Fluor-conjugated 700 mouse anti-human CD3, APC-conjugated mouse anti-human CD4, and BV421-conjugated mouse anti-human CD8 antibodies were purchased from BD Biosciences, San Jose, CA. Monoclonal mouse anti-human HIV-1p24 (clone Kal-1), monoclonal mouse anti-human leukocyte antigen (HLA-DR; clone CR3/43), and the polymer-based HRP-conjugated anti-mouse EnVision+ secondary antibodies were purchased from Dako, Carpinteria, CA.

Flow cytometry: GFP expression in infected cells was quantified using Guava EasyCyte Mini flow cytometer (Guava Technologies, Hayward, CA, USA). Cells were first fixed for 10 minutes in 2% paraformaldehyde then washed 3 times in PBS and analyzed. Peripheral blood was collected from the submandibular vein into ethylenediaminetetraacetic acid (EDTA)-coated tubes or by cardiac puncture at the study end. Blood leukocytes were tested for human pan-CD45, CD3, CD4, CD8, CD14, and CD19 markers as six-color combinations using LSR-II FACS analyzer (BD Biosciences). Antibodies and isotype controls were obtained from BD Pharmingen, San Diego, CA, USA, and staining was analyzed with a FlowJo (BD Immunocytometry Systems, Mountain View, CA, USA). Results were expressed as percentages of total number of gated lymphocytes. The percentages of CD4 and CD8 positive cells were obtained from human CD3$^+$ gate set (10).

In vivo HIV-1 infection: At 18 weeks of age, 25 humanized NSG (NSG-hu) mice were infected intraperitoneally (i.p.) with HIV-1$_{NL4-3}$ (27, 28) at $10^5$ tissue culture infective dose50 ($TCID_{50}$)/ml and sacrificed at days 1, 3, 7 and 14; n=5 at each time point. Five control-uninfected animals were included in all test evaluations. Levels of viral RNA copies/ml were analyzed with the automated COBAS Ampliprep System V2.0/Taqman-48 system (Roche Molecular Diagnostics, Basel, Switzerland) (17, 29). For this assay, 100 μl of mouse serum was diluted to 1 ml with sterile filtered normal human serum. The detection limit of the assay after dilution is 200 viral RNA copies/ml.

Immunohistochemistry examinations: Spleen, lung, liver, and lymph nodes were perfused with PBS followed by 4% paraformaldehyde and then post fixed overnight and embedded in paraffin. Five-micron thick sections were cut from the paraffin blocks, mounted on glass slides and labeled with mouse monoclonal antibodies (DakoCytomation, Carpinteria, CA, USA) for HLA-DQ/DP/DR (clone CR3/43, 1:100) and HIV-1p24 (1:10). The polymer-based HRP-conjugated anti-mouse Dako EnVision system was used as a secondary detection reagent and developed with 3,3'-diaminobenzidine (DAB). All paraffin-embedded sections were counterstained with Mayer's hematoxylin. Deletion of primary antibodies or mouse IgG served as controls. Images were obtained with a Nikon DS-Fi1 camera fixed to a Nikon Eclipse E800 (Nikon Instruments, Melville, NY) using NIS-Elements F 3.0 software.

Preparation of antiretroviral nanoformulations: Antiretroviral prodrugs and their polymer encasements were performed as previously described (7, 8). Myristoylated modifications for DTG, 3TC and ABC were made (referred to as MDTG, M3TC and MABC) to enhance the incorporation into the nanoparticles and RPV was encased solely by poloxamer 407 (P407) in unmodified form using high pressure homogenization to form crystalline nanoformulated drugs. Particle size, polydispersity index, and zeta potential were determined by dynamic light scattering using a Malvern Nano-ZS (Malvern, Worcestershire, UK) (30). Final drug concentrations in the nanoformulation suspensions and injection solutions were determined by HPLC-UV/Vis and UPLC-MS/MS. A 40-50 μl volume for each nanoformulation combination (NMDTG/NRPV and NM3TC/NMABC) was administered by intramuscular (IM) injection in opposing thigh muscles of the mice.

Nucleic acid extractions and q-PCR assays: In studies presented in FIGS. 1A-1G, 3A-3E, and 4A-4G total viral nucleic acids (RNA and DNA) extracted from tissue or cells were acquired from the spleen, bone marrow, lung, GALT, liver, kidney, and brain using a Qiagen Kit (Qiagen, Hilden, Germany) according to the manufacturer's instructions. Total cellular DNA and RNA obtained from the HIV-1 infected cell line ACH2 served as a positive control, while human genomic DNA was obtained from uninfected humanized mice as negative controls. Cell-associated HIV-1 RNA and DNA were quantified by q-PCR and droplet digital PCR (ddPCR) assays. Because of extremely low numbers of latently-infected human cells in HIV-infected humanized mice after long-term ART, detection of total HIV-1 DNA, requires two rounds of PCR amplification. The first round of PCR was performed on a conventional PCR machine (T100 Thermal Cycler, Biorad, CA, USA) in 25 µl of PCR master mix containing 5 µl of template and 50 ng each of both primers annealing to HIV gag region as follows: 94° C. for 3 min, followed by 15 cycles of 94° C. for 30 s, 55° C. for 30 s, and 72° C. for 1 min. The product of the first PCR was subsequently used as a template in the second semi-nested real-time PCR amplification performed on the ABI Prism 7000 real-time PCR machine (Applied Biosystems, MA, USA) using TaqMan detection probe. A total of 2 µl of the first PCR product was diluted to 50 µl with PCR master mix containing 0.2 µM concentrations each of both primers and 0.2 µM TaqMan dual-labeled fluorescent probe. Real-time PCR settings were as follows: 50° C. for 2 min, then 95° C. for 10 min, followed by 40 cycles of 95° C. for 15 s and 60° C. for 1 min. The amplicon sizes are 221 bp for the first round of PCR and 83 bp for the second round (real-time) PCR. ACH2 cells ($8 \times 10^5$) containing one integrated copy of HIV-1 per cell were used in triplicate as standards and HIV copy numbers ranging in serial 10-fold dilutions from $10^5$ to $10^1$ DNA copies/reaction (17, 18). Integrated DNA provirus was quantified using an adapted alu-PCR assay as described by Agosto et al. (31) with modifications for the second round of PCR, following prior published methods (32). Briefly, samples underwent a first-round PCR amplification (95° C. for 2 min; 20 cycles of 95° C. for 15 s, 50° C. for 15 s, and 72° C. for 150 s) using 100 nM alu and 600 nM gag reverse primers. Five µl of the first-round product were amplified in a nested protocol using the assay for HIV-1 gag gene (second PCR primers and probe), as described above. A first-round PCR with 3 replicates using only the gag reverse primer (gag only) acted as background un-integrated control. Serially diluted integration site standards were used to construct a standard curve for each plate. Integration levels per cell were calculated by subtracting gag-only signals from the alu-gag quantification. Semi-nested real-time PCR on HIV-1 RNA was performed as described (17, 18). The eluted cellular RNA was first subjected to DNase treatment to remove HIV-1 DNA to avoid the interference with the quantitation. For reverse transcription assay, random hexamers were used as primers and SuperScript III (Invitrogen, MA, USA) to synthesize first-strand cDNA at 42° C. for 60 min. cDNA was used for the unspliced (usRNA) assay. Two rounds of PCR were performed under the same PCR conditions as described for total viral DNA. For the usRNA assay, real-time PCR was run for 45 cycles. For the usRNA assay, the same primers and fluorescent probe were used as for the total viral DNA assay. The amplicon size was 115 bps.

In studies presented in FIGS. 2A-2C, 11, 12A-12C, 13A-13M, 14A-14F, 20A-20D, 21A, 21B and 22A, 22B and, frozen tissues were homogenized using Bullet Blender homogenizer (Next Advance, Averill Park, NY, USA) using bead combinations and settings specific for every tissue according to manufacturer protocols. T1 buffer from NucleoSpin Tissue kit (Macherey-Nagel, Duren, Germany) was used for homogenization/initial lysis followed by overnight proteinase K digestion. Extraction of genomic DNA was completed according to the protocol of the manufacturer. For standard PCRs (Table 1.1), 500 ng of extracted DNA were subjected to PCR using Fail Safe PCR kit and buffer D (Epicentre, Madison, WI, USA) under the following PCR conditions: 94° C. 5 minutes, 30 cycles (94° C. 30 s, 55° C. 30 s, 72° C. 30 s), 72° C. 7 minutes using $1^{st}$ round primers followed by nested PCR using diluted $1^{st}$ round PCR reaction. Nested PCR products were subjected to Sanger sequencing directly if only one amplicon population was detected by agarose gel electrophoresis. For multiple amplicons detected, or to investigate the composition of HIV excision, each amplicon population was separated and purified from an agarose gel electrophoresis and then cloned into TA vector (Invitrogen, Carlsbad, CA, USA). Plasmid DNA containing excised HIV amplicon was purified from each bacterial colony for Sanger sequencing (Genewiz, South Plainfield, NJ, USA). HIV-1 DNA was quantified using TaqMan qPCR specific for HIV-1 pol and env genes and cellular beta-globin gene as a reference (Table 1.2). Prior to qPCR, genomic DNA was diluted to 10 ng/ul and then 5 µl (=50 ng) were taken per reaction/well. Reaction mixtures were prepared using Platinum Taq DNA Polymerase (Invitrogen) according to a simplified procedure (33) Standard was prepared from serial dilutions of U1 cells genomic DNA since it contains two single copies of HIV-1 provirus per diploid genome equal to beta-globin gene copy number. qPCR conditions: 98° C. 5 minutes, 45 cycles (98° C. 5 minutes, 45 cycles (98° C. 15 s, 60° C. 30 s with acquisition, 72° C. 1 minute). Reactions were carried out and data analyzed in a LightCycler96 (Roche, Basel, Switzerland). For RT PCR, TRIzol reagent (Ambion, Austin, TX, USA) was used for initial RNA extraction followed by clean up using RNeasy kit (Qiagen, Hilden, Germany) with DNAse I digestion in the extraction column. Total 0.5 µg of RNA was used for M-MLV reverse transcription (Invitrogen). For gRNA expression screening specific reverse primer (pX601gRNA scaffold/R, Table 1.3.) was used in RT reaction followed by standard PCR using target LTR 1 or Gag D sense oligos as forward primers (Table 1.3) and agarose gel electrophoresis. For checking saCas9 mRNA expression oligo-dT primer mix was used in RT and cDNA was subjected to PCR using saCas9 specific primer pairs and b-actin as a reference (Table 1.3).

Sequence analysis: Sanger sequencing results were analyzed using Clustal Omega (EMBL-EBI) multiple sequence alignment tool and Sequence Scanner Software 2 (Applied Biosystems).

Off-target analysis—Cell culture model. TZM-bl cells were plated in 6 well plates at $1 \times 10^5$ cells/well and co-transfected using Lipofectamine 2000 reagent (Invitrogen) with 1 ug of control pX601-AAV-CMV:NLS-SaCas9-NLS-3×HA-bGHpA; U6::Bsa1-sgRNA (Addgene #61591) or 1 µg of pX601-LTR1-GagD (16) plasmid together with 0.2 µg of pKLV-U6gRNA(Bbs1)-PGKpuro2ABFP (Addgene 50946) to provide puromycin selection marker. Next day, cells were transferred into 100-mm dishes and cultured in the presence of puromycin (Sigma) at concentration 1 µg/ml. After two weeks, surviving clones were isolated using cloning cylinders (Corning, Corning, NY, USA). Genomic DNA was prepared from each single cell clone and LTR specific PCRs followed by gel purification; TA cloning and Sanger sequencing were performed. The clones showing the presence of on target CRISPR-Cas9 induced InDel mutations at target LTR 1 site in integrated HIV-1 LTR sequence (n=6) together with two control clones were selected for further in vitro off target analysis. The list of potential OFF target sites in human genome for HIV-1 target LTR 1 and Gag D was created using Benchling CRISPR design tool (Benchling, San Francisco, CA 94103 (benchling.com) Tables 2 and 3). Total three potential OFF target sites were chosen (the top scorer plus two top gene specific potential off target sites, see Tables 2 and 3 for PCR based screening in selected single cell clones. The potential OFF target regions (Table 1.4) were PCR amplified, cloned into TA vector, and sent for Sanger sequencing (3-6 sequences/single cell clone/single OFF target).

Humanized mice model: The genetic variation analyses among the three treatments were performed through the next generation sequencing (by the Novogene NGS facility) and bioinformatics tools for four sample animals, one animal from the LASER ART, one animal from CRISPR-Cas9— and two no-rebound animals from the LASER ART+ CRISPR-Cas9 groups. The main objective was detecting the possible CRISPR/Cas9 off-target sites. Besides this, some genetic variations such as single nucleotide polymorphisms (SNP), -nsertion-deletions (InDels), structural variants (SVs) and copy number variants (CNVs) were analyzed for those four animals and the results are given in FIGS. 19A-19C, 20A-20D and Tables 4-6. After a thorough quality control step, the resulting paired-end short-reads were mapped to the human reference genome (Human_G1K_V37) utilizing Burrows-Wheeler Aligner (BWA) algorithm. For the animals #4356 (CRISPR-Cas9), #4348 and #4349 (LASER ART+CRISPR-Cas9) and #3539 (LASER ART), the coverages were reported to be 92.01%, 91.97%, 92.01% and 91.92%, while the sequencing depths were 36.08, 63.11, 45.22, and 15.41, respectively.

ddPCR for detection of HIV-1 nucleic acids: ddPCR was performed based on the water-oil emulsion droplet technology and used for viral detection using the outlined primers (Forward—5'-TCAGCCCAGAAGTAATACCCATGT-3' (SEQ ID NO: 1) and Reverse-5'-CACTGTGTTTAGC ATGGTGTTT-3' (SEQ ID NO: 2)) and a TaqMan probe. The ddPCR assay was run with the ddPCR™ SUPERMIX for Probes reagents in the QX200™ DROPLET DIGITAL™ PCR system (Bio-Rad Laboratories, Hercules, CA, USA). For quantification of integrated HIV-1 DNA, the eluted cellular DNA was PCR amplified (17, 18, 31, 32) for integrated viral DNA (iDNA) targeting the HIV-1 gag gene. Total 100 ng of each tissue DNA template were used for ddPCR amplifications and performed on the QX200™ DROPLET DIGITAL™ PCR system (Bio-Rad Laboratories, Hercules, CA, USA) using the ddPCR™ Supermix for Probes reagents following the thermal cycling conditions for TaqMan detection. Data acquisition and analysis were done using QX200 droplet reader and QUANTASOFT™ software (Bio-Rad Laboratories, Hercules, CA, USA).

RNAscope assay: Viral RNA was detected as single brown dots or cluster of dots in 10 μm thick spleen tissue sections using antisense probe V-HIV1-Clade-B (ACD cat no 416111) targeting 854-8291 bp of HIV-1$_{NL4-3}$ (34) Human peptidylprolyl Isomerase B (PPIB) was used as positive control for the spleen tissue analyzed (images were captured at 40× magnification).

Viral recovery: Phytohemaglutinin (PHA) and inter-leukin-2 (IL-2) stimulated peripheral blood mononuclear cells (PBMCs) obtained from leukopaks from HIV-1,2 sero-negative donors were co-cultured with human bone marrow (BM) or spleen cells recovered from infected and or LASER ART with and without AAV$_9$-CRISPR-Cas9 treated humanized mice. PBMCs were used in assays after 3-day treatment maintained in 10% RPMI with 30 U/ml of IL-2 then co-cultured with human BM or spleen cells at concentrations of (1:5) (35-37). Cells were harvested eight days later for HIV-1 DNA (A) and RNA (B) using semi-nested real-time PCR assay and supernatant fluids assayed for reverse transcriptase activity. Data are expressed as total HIV-1 DNA (A) or RNA (A) copies/$10^6$ human CD45 cells. One of two dual treated animals was tested and confirmed viral sterilization. Viral rescue was observed in other animals tested.

Excision efficiencies and hierarchal clustering: The excision efficiencies for each animal, tissue, and HIV-1 gene segment were calculated as the ratio of the number of the sequencing-verified PCR product to all members in each group with denoted experimental conditions (i.e. treatments, tissues, etc. shown in FIGS. 2A-2C, 11, 12A-12C, 13A-13M). Defined in such a way that the excision efficiencies can be viewed as frequentist probabilities, i.e. the ratio of the frequency of occurrence of the event of interest to the total number of experimental repeats. This interpretation of excision efficiencies provides the user with a predictive value, as they can be used to set a prior expectation on the success rate of each treatment (LASER ART, CRISPR-Cas9, and LASER ART plus CRISPR-Cas9) in excising the desired segments of HIV-1 gene in the studied tissues and further to relate that to the likelihood of cure.

Hierarchical clustering was performed on the efficiency values of truncation events under different treatments and across different animals, tissues, and HIV-1 gene segments. Once the excision efficiencies were calculated under different combinations of experimental conditions, the hierarchical clustering scheme was employed to group the efficiency values into a multilevel cluster tree represented by a dendrogram. The corresponding efficiency values were listed in heat-map table, to make the clusters visually detectable. To this end, three combinations were considered: i) excision probabilities of different HIV-1 segments in 6 different tissues of animals undergoing antiretroviral treatment, CRISPR-Cas9 mediated editing, and the combined treatments (FIG. 17A); ii) excision probabilities of different segments in different animals under the three treatments (FIG. 17B); and iii) probabilities of observing at least one positive band for each specified tissue in all animals (FIG. 17A). Clusters of FIGS. 17B and 17C also include additional conditions of "Cure" and qPCR data to identify which animals experienced complete cure and highest viral genome eradication. Note that, in all figures, S1 refers to 5' LTR to Gag excision and S2 refers to Gag to 3' LTR excision of the HIV-1 genome, respectively.

Statistical analyses: Data were analyzed by GraphPad Prism 7.0 software (La Jolla, CA, USA). Data are represented as the mean+/−the standard error of the mean (SEM). Experiments were performed using a minimum of three biologically distinct replicates. For comparisons of two groups, Student's t test was used. T cell populations, viral RNA and DNA, and viral load were analyzed by one-way ANOVA with Bonferroni correction for multiple-comparisons. For studies with multiple time points, two-way factorial ANOVA and Bonferroni's post-hoc tests for multiple comparisons were performed. Multiple comparisons were corrected for the false discovery rate (FDR) using the Benjamini-Hochberg procedure. Animal studies included a minimum of 5-7 animals per group unless otherwise noted. Extreme outliers beyond the 99% confidence interval of the mean and 3-fold greater than the SEM were excluded. Significant differences were determined at a p<0.05.

Results

A functional cure of HIV infection was documented in a single person (1). However, efforts were stalled by a combination of limited therapeutic access to viral reservoirs, rapid spread of infection, high numbers of virus susceptible cells, and complete inability to eliminate latent integrated proviral DNA. These therapeutic treatments have precluded viral eradication as rebound was seen after cessation of antiretroviral therapy (ART) (2-6).

To address each of these limitations, highly hydrophobic and lipophilic antiretroviral prodrugs termed herein "long-acting slow effective release antiretroviral therapy" (LASER ART), were produced to improve drug penetrance across cell and tissue barriers and improve control over ongoing viral infection (7-10). Further, CRISPR-Cas9 technology was employed that specifically and efficiently excised fragments of integrated HIV-1 proviral DNA from the host genome in cell cultures as well as in several tissues from small animal models (11-16). To provide proof of concept that LASER ART and CRISPR-Cas9 treatments could produce synergy towards viral elimination, gut-associated lymphoid tissue (GALT), spleen, lymph nodes, brain, lung, liver, and kidney tissues of NOD.Cg-Prkdc$^{scid}$ Il2rg$^{tm1Wjl}$/SzJ (NSG) mice were populated with human peripheral blood lymphocytes (PBLs) then infected with $10^4$ tissue culture infective dose$_{50}$ (TCID$_{50}$) of HIV-I$_{NL4-3}$ (17, 18). Three days later, animals were divided into four groups (n=7 for each group). Groups were control (uninfected) and infected animals left untreated or treated with LASER ART as defined by combinations of myristoylated dolutegravir (DTG), lamivudine (3TC) (8) and abacavir (ABC) (7) prodrugs and rilpivirine (RPV) nanoformulations with or without AAV$_9$-CRISPR-Cas9. All treatments were simultaneously administered. After two weeks, CD4$^+$ T cells and viral DNA and RNA levels were assessed in blood and tissues. No significant differences in the levels of CD4$^+$ T cells and viral DNA and RNA levels were observed between the treatment groups. However, animals treated with both LASER ART and AAV$_9$-CRISPR-Cas9 viral RNA and DNA levels were decreased more than those receiving LASER ART which by itself restored CD4$^+$ T cells and reduced plasma viral RNA to or below baseline (FIGS. 5A-5F). These results provide evidence that CRISPR-Cas9 would be most effective in HIV-1 LTR and the Gag gene excision in an ART setting. Support for this notion was realized from follow up in vitro and ex vivo studies. These investigations showed significant increases in the proficiency of CRISPR-Cas9 excision of HIV-1 proviral DNA in infected T-cells following ART-induced viral restriction (FIGS. 6A-6C, 7A-7E).

Based on these observations, an amended treatment strategy was adopted (FIG. 1A) based on the assumption that ART-induced viral suppression would improve CRISPR-Cas9 editing efficiency and facilitate viral elimination without bystander tissue toxicities (16, 19, 20). humanization of the animals was confirmed by flow cytometry for CD45 and CD3 staining of blood immune cells in animals demonstrating human cell survival in all mouse groups (FIGS. 178A and 8B). All infected animals showed marked depletion of CD4$^+$ T cells (FIGS. 1B and 1G) and plasma viral RNA levels at a median of $2.2 \times 10^5$ copies/ml (FIGS. 1C and 1F). Immunohistochemical examination for HIV-1p24 antigens in spleen, lymph node, and lung showed broad distribution of infected HLA-DR reactive human cells (FIG. 1D). Semi-nested real-time q-PCR HIV-1 nucleic acid detections confirmed viral infection in tissue (FIG. 1E). These infected animals were then divided into four groups. The first received no treatment; group 2 received a single intravenous (IV) injection of AAV$_9$-CRISPR-Cas9, and the third and fourth groups received 40-45 mg/kg LASER ART. The fourth group, in addition, received AAV$_9$-CRISPR-Cas9 after three weeks of LASER ART. After the last administration of LASER ART, animals were observed for 8 weeks for any evidence of viral rebound, which corresponded to 5 weeks of AAV$_9$-CRISPR-Cas9 treatment. Such rebound was observed in all groups with the exception of two animals in group 4 animals #4346 and #4349, which received a combination LASER ART and CRISPR-Cas9 (FIG. 1F). Restoration of CD4$^+$ T cell counts (90% f 7%) was observed in dual treated group 4 animals, which was higher than those seen in group 3 that received only LASER ART (82%+ 12%). In the absence of LASER ART, restoration of CD4$^+$ T cells with CRISPR-Cas9 treatment (group 2) remained low (15% f 6), yet slightly higher than those seen in Group 1 (no treatments, less than 6%) (FIG. 1G). Immunohistochemical evaluation of spleens from HIV-1 infected animals for the presence of CD4$^+$ T cells showed comparable increases (FIG. 9). Further, detection of human DNA sequence in spleen confirmed the presence of the human cells in the spleen of the humanized animals (FIG. 10).

Gel electrophoresis analysis of the PCR amplified DNA fragments using specific pairs of primers designed for detection of the various cleavage events (FIG. 2A) revealed robust cleavage and excision of viral DNA fragments obtained from spleen, GALT, and kidney of the group of animals treated with LASER ART and AAV$_9$-CRISPR-Cas9 (FIG. 2B). Also, it was noted that the type of excision differed in various tissues among the animals as well as in the same individual animals. Efficient excision of the predicted fragment in other tissues including lung, liver, and brain was also observed in some of the animals with dual treatments (FIG. 11). The integrity and precision of the HIV-1 DNA excision by CRISPR-Cas9 were sequence verified (FIG. 2C, and FIGS. 12A-12C, 13A-13M). In mice that received AAV$_9$-CRISPR-Cas9 without LASER ART fragmental deletion was detected. Several other DNA fragments in tissues from the experimental animals, including those that received only LASER ART, were amplified, which after sequencing were found unrelated to HIV or editing by CRISPR-Cas9 that may represent replication defective HIV-1 (highlighted by double asterisks) (FIG. 2B and FIGS. 14A-14F). Amplification of the DNA fragments corresponding to control housekeeping actin gene in the various tissues and expression of gRNAs and Cas9 are shown (FIG. 15).

Clustering analysis revealed similar excision patterns with high efficiency across the different tissues in the cohort of animals that received combination treatments in comparison to those detected in the groups that received only CRISPR-Cas9 (FIGS. 16A-16C). This hierarchical clustering heat map may offer a predictive capability for viral elimination after the interruption of LASER ART in this model. Bioinformatics analysis of human genome sequence data identified several human genome sites that may serve as targets for gRNAs that are designed for editing of HIV-1 DNA. However, results from sequencing of several selected sites with high scores of specificities and/or their locations in the exons ruled out any off-target effect on genome of human cell line (FIGS. 17A-17C and 18A-18F). Further, deep sequencing of genomic DNA from spleen of the four treated animals, including two that showed no rebound after combination treatment and one from each group with single treatment followed by bioinformatics analysis in search for somatic InDels mutation in the human genome by multiple alignments involving nucleic acids blast revealed no off target effects such as single nucleotide variations, translocation, inversion, deletion, tandem duplication, and insertion in the human genome, that can be attributed to CRISPR-Cas9 (FIGS. 19A-19C, 20A-20D and Tables 6, 7).

Next, tissue viral DNA and RNA levels were determined in tissues using ultrasensitive semi-nested real time qPCR with primers and probes designed for detection of HIV-1 gag (21, 22) DNA analysis results revealed that combination treatment was more effective than either LASER ART or CRISPR-Cas9 alone in reducing viral DNA copies. The spleen, GALT, and bone marrow of mice #4346 and #4349 showed no rebound (FIG. 3A). Similarly, results from the RNA detection assay corroborated with the data from the DNA study showed the combination of LASER ART and CRISPR-Cas9 reduced HIV-1 RNA production in select animals with complete absence of viral RNA in #4346 and #4349 (FIG. 3B). The presence of HIV-1 RNA was also examined by RNA scope using 10 μm thick spleen sections from infected animals and antisense probe V-HIV-1 Clade-B designed for targeting 854-8291 base pairs of the HIV-1$_{NL4-3}$. Mouse #4346 with no viral nucleic acid and rebound showed no evidence of viral gene expression (FIG. 4A). Results from the targeted qPCR for DNA sequence detection corresponded to the middle of HIV-1 genome and ruled out the presence of DNA corresponding to the pol and env genes (FIGS. 4B-4C). Additional evidence for the absence of HIV-1 genomes in the animals #4346 and #4349 was provided by digital droplet PCR (ddPCR) tests. This assay had a sensitivity of detection of <2 viral copies. Verifying prior results, no viral DNA was detected in spleens of mice #4346 and #4349 and examination of other tissues showed complete HIV-1 eradication (FIGS. 4D-4E). Finally, a viral rescue assay was performed by co-culturing bone marrow cells and splenocytes of representative samples with PHA/IL-2 PBMCs for an additional two weeks. Representative data (FIG. 4F) showed that while HIV-1 was rescued from 100% of samples with detectable viral DNA and RNA, despite the presence of high number of human cells, no evidence for virus recovery was observed in the samples from the two animals with eradicated HIV-1 DNA and RNA.

Accordingly, these results provide evidence that the combination of lipophilic LASER ART and AAV$_9$ delivered CRISPR-Cas9 can potentially lead to the cure of HIV-1 infection by elimination of the replication component of the virus in HIV-1 reservoirs of infected animals as evidenced by the absence of viremia for more than 8 weeks after the last ART treatment. Although the re-appearance of viremia in humans can occasionally be delayed longer (5), the rebound of HIV occurs an average of 2-4 weeks after ART interruption (4, 23) and 5-9 days in animal models (24). These results offer a realistic pathways toward an HIV-1 cure.

TABLE 1

| PCR primers and probes | | | |
|---|---|---|---|
| | primer | sequence | SEQ ID NO |
| | | 1. Standard PCRs | |
| 5'LTR-gag | 1$^{st}$ round LTR F | 5'-AATTGCGGCCGCTGGAAGGGCTAATTTGGTCCC-3' | 3 |
| | 1$^{st}$ round gag R | 5'-TGTCACTTCCCCTTGGTTCTCTC-3' | 4 |
| | nested 5'LTR F | 5'-AAAAGAATTCGTGGATCTACCACACACAAGGC-3' | 5 |
| | nested gag R | 5'-AAAAGGATCCACCATTTGCCCCTGGAGGTT-3 | 6 |
| Gag-3'LTR | 1$^{st}$ round gag F | 5'- GAAAGCGAAAGTAAAGCCAGAGGAGAT-3 | 7 |
| | 1$^{st}$ round LTR R | 5'-ACACAACAGACGGGCACACACTACTT -3' | 8 |
| | nested gag F | 5'AAAAGAATTCGACAGCTACAACCATCCCTTCA GACAG-3' | 9 |
| | nested 3'LTR R | 5'-AAAAGGATCCAGCAGTGGGTTCCCTAGTTAGCC AG-3' | 10 |
| LTRs | 1$^{st}$ round LTR −413/S | 5'-TTGGCAGAACTACACACCAGGG -3' | 11 |
| | 1$^{st}$ round LTR +43/AS | 5'-CCGAGAGCTCCCAGGCTCAGATCT-3' | 12 |
| | nested LTR −374/S | 5'-TTAGCAGAACTACACACCAGGGCC-3' | 13 |
| | nested LTR −19/AS | 5'-GCTGCTTATATGTAGCATCTGAG-3' | 14 |
| Hs beta-globin | Hs b-globin F | 5'-CCCTTGGACCCAGAGGTTCT-3' | 15 |
| | Hs b-globin R | 5'-CGAGCACTTTCTTGCCATGA-3' | 16 |
| Mm beta-globin | Mm b-globin F | 5'-CCCTTGGACCCAGCGGTACT-3' | 17 |
| | Mm b-globin R | 5'-GTTATCACCTTCTTGCCATG-3' | 18 |
| 2. Taqman qPCRs | | | |
| pol | HIV-1 pol/int F | 5'-TCCAGCAGAGACAGGGCAAG-3' | 19 |
| | HIV-1 pol/int R | 5'-TGCCAAATTCCTGCTTGATCCC-3' | 20 |
| | HIV-1 pol/int probe | 5'-HEX-CGCCCACCAACAGGCGGCCTTAACTG-ZEN-IowaBlackFQ-3' | 21 |
| env | HIV-1 Env F | 5'- TCCTTGGGATGTTGATGATCT-3' | 22 |
| | HIV-1 Env R | 5'- TGGCCCAAACATTATGTACC-3' | 23 |
| | HIV-1 Env Probe | 5'-FAM-TGGTGGTTGCTTCTTTCCACACA-ZEN-IowaBlackFQ-3' | 24 |

TABLE 1-continued

| | primer | sequence | SEQ ID NO |
|---|---|---|---|
| | PCR primers and probes | | |
| reference | Hs b-globin F | 5'-CCCTTGGACCCAGAGGTTCT-3' | 25 |
| | Hs b-globin R | 5'-CGAGCACTTTCTTGCCATGA-3' | 26 |
| | Hs b-globin probe: | 5'-FAM-GCGAGCATCTGTCCACTCCTGATGCTGTTATGGG CGCTCGC-ZEN-IowaBlackFQ-3' | 27 |

3. RT-PCRs

| | LTR1/F | 5'-GCAGAACTACACACCAGGGCC-3' | 28 |
|---|---|---|---|
| | GagD/F | 5'-GGATAGATGTAAAAGACACCA-3' | 29 |
| | pX601gRNAscaffold/R | 5'-CGCCAACAAGTTGACGAGAT-3' | 30 |
| | SaCas9/263/F | 5'-TCGACTACAACCTGCTGACC-3' | 31 |
| | SaCas9/SEQ1 | 5'-GGTGGGCTTCTTCTGCTT-3' | 32 |
| | b- actin S | 5'-CTACAATGAGCTGCGTGTGGC-3' | 33 |
| | b-actin AS | 5'-CAGGTCCAGACGCAGGATGGC-3' | 34 |

4. In vitro OFF target analysis

| | | | | |
|---|---|---|---|---|
| LTR 1 OFF targets | LTR1OFFch8/F | 5'-GAGTGACCTTCCCAAATTGC-3' | 35 | |
| | LTR1OFFch8/R | 5'-ATGGTGAGGTGAGGGATGAG-3' | 36 | |
| | TSC2/35001F | 5'-CAGACTCTGATGGGTGGCAG-3' | 37 | |
| | TSC2/35398R | 5'-GCTAAGGAGAGAGGGTGGGA-3' | 38 | |
| | TUB/66607F | 5'-CCAAGTGGCCCTCAGATTACA-3' | 39 | |
| | TUB/67015R | 5'-TCATTCACCCCAAATCCTACGG-3' | 40 | |
| Gag D OFF targets | GagDOFFch3/F | 5'-CATTAACCACCTGGGGAACA-3' | 41 | |
| | GagDOFFch3/R | 5'-TCTCAGACCCAGGAATGTCA-3' | 42 | |
| | TACC2/392F | 5'-GAGGACTCTCCAGCCAAAGG-3' | 43 | |
| | TACC2/782R | 5'-GAGCTGGGGGTCTTAGAGGA-3' | 44 | |
| | ADNP/41574F | 5'-TGCACCAGCCAAAACTTAGGA-3' | 45 | |
| | ADNP/41996R | 5'-TCTAATTAGGTGGCAGCACGTT-3' | 46 | |

TABLE 2

HIV-1 LTR 1 target (+strand)
GCAGAACTACACCAGGGCCAGGAT

| Sequence | PAM | Score | Gene | Chromosome | Strand | Position | Mismatch | On-target |
|---|---|---|---|---|---|---|---|---|
| TCTAAAC TCCACAC CAGGGCC | ATGAA | 2.6 | | chr8+22915337 | 1 | 22915337 | 4 | FALSE |
| TCAGATC TCCACAC CAGAGC C | ACGAG | 1.3 | | chr9:+38360364 | 1 | 38360364 | 4 | FALSE |
| ACAGGCC AACCCAC CAGGGCC | CAGAG | 0.9 | | chr22:-201 | -1 | 20136959 | 5 | FALSE |
| GTAGGAC TACGCAC CAGGGCA | AAGAG | 0.9 | | chr8:-92102695 | -1 | 92102695 | 4 | FALSE |
| ACAAAAG TACACAC CAGAGCC | TGGGG | 0.8 | | chr11+7562503.5 | 1 | 75625035 | 4 | FALSE |
| TGTGMCT ACGCCCC AGGGCC | TGGM | 0.0 | | chr:13:-273-41725 | -1 | 27341725 | 5 | FALSE |
| ACAGGCT GAGCACC AGGGCC | CAGGG | 0.8 | | chr11:-124217737 | 1 | 1.24E-08 | 5 | FALSE |

TABLE 2-continued

| HIV-1 LTR 1 target (+strand) GCAGAACTACACCAGGGCCAGGAT | | | | | | | | |
|---|---|---|---|---|---|---|---|---|
| Sequence | PAM | Score | Gene | Chromosome | Strand | Position | Mismatch | On-target |
| CCAGTTC TCCACCC CAGGGCC | ATGGA | 0.8 | | chr15:+28948038 | 1 | 28948038 | 5 | FALSE |
| CCAGAGC TGCTTAC CAGGGCC | ATGGA | 0.7 | | chr1:-47650696 | -1 | 47650696 | 5 | FALSE |
| ACAGCAC TCCCCAC CAGGGCT | TGGGG | 0.7 | TSC2 (ENSG000 00103197) | chr16:+2082981 | 1 | 2082981 | 5 | FALSE |
| ACAGfAC GTCACAC CAGGGTC | AGGAG | 0.7 | | chr7:-26573832 | -1 | 26573832 | 4 | FALSE |
| ACAA.AAC TAGACAG CAGGGCC | AGGAG | 0.7 | | chr19:-54347353 | 1 | 54347353 | 4 | FALSE |
| TGAGLAC TTCACAG CAGGGCC | GGGAA | 0.7 | | chr2:+43112424 | -1 | 43112424 | 5 | FALSE |
| GCAGCAC TACACAT CAGGGCT | AAGM | 07 | | chr16:-60058984 | -1 | 60058984 | 3 | FALSE |
| CCGCMCT CCACAGC ACCGCC | ACGCA | 0.7 | | chr15:-80851232 | 1 | 80851232 | 5 | FALSE |
| CTAGAGG MCACACC AGGGCC | TGGGA | 0.6 | | chrX:-10:3784275 | 1 | 1.04E+08 | 5 | FALSE |
| ACAGCCC CAGACAC GAGGGCC | TGGAG | 0.6 | | chr15:-575422584 | 1 | 575422584 | 5 | FALSE |
| CCAGGTC TACCCAG CAGGGCC | AGGAG | 0.6 | | chr11:-121718784 | 1 | 1.22E+08 | 5 | FALSE |
| ACAGGAG GGCACAC AGGGCC | CAGGA | 06 | | chr13:-47252260 | 1 | 47252260 | 5 | FALSE |
| ACAGAM TAANACC AGGGCT | TCGGG | 0.6 | | chr2:-1206433 | 1 | 12064300 | 4 | FALSE |
| GCAGTGC CACACTC CAGGGCC | TGGGG | 0.6 | | chr11:-76235199 | 1 | 76235199 | 3 | FALSE |
| CCAGAGC ACCAAAC CAGGGCC | CAGGA | 0.5 | | chr2:-238434996 | 1 | 2.38E+08 | 4 | FALSE |
| GCAGAGC TCCCCAC CAGGGGC | AGGGA | 0.5 | | chr2:-127586882 | 1 | 134E+08 | 4 | FALSE |
| TCAGGCC CACACTC CAGGGCC | CAGAA | 0.5 | | Chr5:-1342488:16 | 1 | 11048922 | 3 | FALSE |
| GCAGTGC CACACTC CAGGGCC | TTGGG | 0.5 | | chr19:-11040922 | 1 | 41442886 | 4 | FALSE |
| GCAGTGC CACACTC CAGGGCC | CTGAG | 0.5 | | chr3:-189039375 | 1 | 1.38E+08 | 4 | FALSE |

TABLE 2-continued

| HIV-1 LTR 1 target (+strand) GCAGAACTACACCAGGGCCAGGAT | | | | | | | | |
|---|---|---|---|---|---|---|---|
| Sequence | PAM | Score | Gene | Chromosome | Strand | Position | Mismatch | On-target |
| GCAGAGC TAGCCAC CAGGGCT | AGGAG | 0.5 | | chr14:-96723779 | -1 | 8105357 | 3 | FALSE |
| GCAGAGC TAGCCAC CAGGGCT | TGGA | 04 | | chr6-13760994 | 1 | 47512275 | 4 | FALSE |
| GCACAGC TCCAGCC CAGCCCC | TCGGG | 0.4 | | chr22:-49956739 | -1 | 68746690 | 4 | FALSE |
| GGGGAAA TACACAT CAGGGCC | AGGAA | 0.4 | | chr20:-43964342 | -1 | 43964342 | 4 | FALSE |
| AGAGAAT TTCACAA CAGGGCC | CTGAA | 0.4 | | chr3:-189039375 | 1 | 1.89E+08 | 5 | FALSE |
| CCTGAAC CACACCC AGGGCT | CAGGG | 0.4 | TUB(EN SGOJ00 0166402) | chr11:-8105357 | -1 | 8105357 | 5 | |
| CATGIGCT ACACACC AGGACC | AGGAG | 0.4 | | chr7:+47512275 | 1 | 47512275 | 5 | |
| GCGGCCT ACACACC AGGCCC | AAGGG | 0.4 | | chr6:-68746690 | -1 | 68746690 | 4 | |
| CCAGMCT CAGCCCC AGGGCC | CTGGG | 0.4 | | chr5:-137113375 | -1 | 1.37E+08 | 5 | |
| GCTGGCC ACACAC CAGGCCC | AGGGG | 0.4 | | chr2:-128441625 | 1 | 38015758 | 4 | |
| CCTGMCC ACACCCC AGGGCT | CAGGG | 0.3 | | chr2:-128441625 | -1 | 1.28E+08 | 5 | |
| GAATAG CTACACA TAGGGCC | AGGAA | 0.3 | | chr10:-95607480 | -1 | 95607490 | 4 | |
| GAATAGC TACACAC TAGGGCC | ATGGA | 0.3 | | chr2:-69175215 | -1 | 69175215 | | |
| GAAGMCC ACAAAAC AGGGCC | GPGAP. | 0.3 | | chrX:+4380387 | 1 | 43803871 | 4 | |
| AIAGIACT ACACICCI GGGCC | TCGAG | 0.3 | | chr5:+5184057 | 1 | 5184057 | 5 | |
| CAAGAAC AACACAG CAGGGCA | GAGAG | 0.2 | TBC1519 (ENSG000 00100680) | chr4:+26576719 | 1 | 26576719 | 4 | |
| CCAGAAA CACCCAC CAGTGCC | CGGGA | 0.2 | | chr19:-15-265258 | 1 | 15265258 | 5 | |
| CCAGAGC TGCAGAC CCGGGCC | CCGGG | 0.2 | | chr9:-1333679870 | -1 | 1.34E+08 | 5 | |

TABLE 2-continued

HIV-1 LTR 1 target (+strand)
GCAGAACTACACCAGGGCCAGGAT

| Sequence | PAM | Score | Gene | Chromosome | Strand | Position | Mismatch | On-target |
|---|---|---|---|---|---|---|---|---|
| CCAGACC GAGAGAC CAGGGGC | GGGGG | 0.2 | | chr12:-104958165 | -1 | 1.0SE+08 | 5 | |
| CCAGATC TAGACTC CAGGGCA | GTGAG | 0.2 | SLC41A2 (ENSG000 00126053) | chr1:-201423414 | 1 | 2.03E+08 | 5 | |
| TCAGIGCT AGACTCC AGGGCT | GGGGG | 0.2 | | chr19:-48393411 | -1 | 48393411 | 5 | |
| GGAGMCT TAACACC ACGTCC | CTGGG | 0.2 | | chr22:-41003477 | -1 | 41003477 | 4 | |
| CCAGCAC CACAGAG CAGGGCC | TGGGA | 0.2 | | chr11:+319276 | 1 | 319276 | 5 | |
| CCAGCAC CACAGAG CAGGGCC | TGGGA | 0.2 | | chr11:+310505 | -1 | 310505 | 5 | |

TABLE 3

HIV-1 Gag D target (+strand)
GGATAGATGTAAAAGACACCAAGGAAG

| Sequence | PAM | Score | Gene | Chromosome | Strand | Position | Mismatch | On-target |
|---|---|---|---|---|---|---|---|---|
| AGAAAAT GTAAAAG ACACCT | TGGAA | 1.7 | | chr3:-144746442 | -1 | 1.45E+08 | 4 | FALSE |
| TTATACAT TTGAAAG ACACCA | AAGAA | 1.5 | | chr1:194738918 | -1 | 195E+08 | 5 | FALSE |
| GGATAAA TGGGAAA GACACCA | GGGGA | 1.5 | | chr16:-48814755 | -1 | 48814775 | 3 | FALSE |
| TCTTAGA CTTAAAA GACACCA | TTGAA | 1 | | chr15:33069866 | -1 | 33069866 | 5 | FALSE |
| ACATTGA ATTAAAA GACACCA | AAGAG | 1 | | chrX:32002168 | -1 | 32002168 | 5 | FALSE |
| GGARAGA GCCAAAA GACACCA | AAGAG | 1 | | chr17:-51350241 | -1 | 51350241 | 3 | FALSE |
| AAATAGC TCTTAAA GACACCA | GCGAA | 0.9 | | chr2:+172764947 | 1 | 1.74E-08 | 5 | FALSE |
| AGATCAA TGTAAAA GTCACCA | TCGAA | 0.9 | | chr6:-144451168 | -1 | 1.44E+08 | 4 | FALSE |
| TTTTAGAT GTAAAAG ACATCA | GGGAG | 0.8 | | chr3:+187644948 | 1 | 1.88E+08 | 4 | FALSE |

TABLE 3-continued

| HIV-1 Gag D target (+strand) GGATAGATGTAAAAGACACCAAGGAAG | | | | | | | |
|---|---|---|---|---|---|---|---|
| Sequence | PAM | Score | Gene | Chromosome | Strand | Position | Mismatch | On-target |
| TGATAAA TGAAACA GACACCA | GAGGA | 0.8 | | chr7:-141719859 | -1 | 1.42E-08 | 4 | FALSE |
| GAAAAGA TTTAAGA GACACCA | AAGAG | 0.8 | | chr2:-213166139 | -1 | 2.13E+08 | 4 | FALSE |
| AGGGAGA TCTAAGA GACACCA | GAGAG | 0.8 | | chr19:-29842353 | -1 | 29842353 | 5 | FALSE |
| GTATGGA TGTTAAA GACTCCA | GGGAA | 0.8 | | chr1:-226725698 | -1 | 2.27E+08 | 5 | FALSE |
| GTATGGA TGTTAAA GACTCCA | TTGAG | 0.7 | | chr5:-142976527 | -1 | 1.43E+08 | 4 | FALSE |
| CGGTAGA TTTTAAAG ACTCCA | AAGAG | 0.7 | | chr9:-38648188 | -1 | 38648188 | 5 | FALSE |
| AGAGAGA TATTAAA GACCCA | GTGAA | 0.6 | | chr18:-43665283 | -1 | 43665283 | 5 | FALSE |
| GGATAAA TGTGAAA GACATCA | TAGAA | 0.6 | | chr18:-51783716 | 1 | 51783716 | 3 | FALSE |
| AGAAGGA GGAAAAA GACACCA | GGGAG | 0.6 | | chr2:+218083925 | 1 | 2.18E+08 | 5 | FALSE |
| TAATAGG TAGAAAA GACACCA | GTGAA | 0.6 | | chr12:-126150002 | -1 | 1.26E+08 | 5 | FALSE |
| CCAAAGA TGAAAAA GACAGCCC | GAGAA | 0.6 | TACC2 (ENSG0000 00139162) | chr10:+122211347 | 1 | 1.22E+08 | 5 | FALSE |
| TTATAAAT GCAAAAG ACACCC | ATGAA | 0.6 | | chr14:-46407726 | -1 | 46407726 | 5 | FALSE |
| GGCTGGG TGAAAAA GAGACCA | TGGAA | 0.6 | | chr6:+66585737 | 1 | 66585737 | 4 | FALSE |
| GGACAGA TGTGAAA GAGACCA | AAGGA | 0.5 | | chr2:+224685483 | 1 | 2.25E+08 | 3 | FALSE |
| TGATGCA AGTAACA GACACCA | TGGA | 0.5 | | chr6:-107524588 | 1 | 1.08E+08 | 5 | FALSE |
| CAATAGTT GTTCAAG ACACCA | GTGAA | 0.5 | | chr6:-156459061 | -1 | 1.56E+08 | 5 | FALSE |
| AGAAAGA TACAGAA GACACCA | GGGAG | 0.5 | | chr11:--75223569 | -1 | 75223569 | 5 | FALSE |
| TGAGACTT GTACAAG ACACCA | CGGGG | 0.5 | ADNP (ENSG000 00101126) | chr20:-50889247 | -1 | 50889247 | 5 | FALSE |
| AGATTGTT GTAAAGA CACCA | CAGAG | 0.5 | | chr7:-114527499 | -1 | 1.15+08 | 5 | FALSE |

TABLE 3-continued

| HIV-1 Gag D target (+strand) GGATAGATGTAAAAGACACCAAGGAAG | | | | | | | |
|---|---|---|---|---|---|---|---|
| Sequence | PAM | ScoreGene | Chromosome | Strand | Position | Mismatch | On-target |
| GGAAAGT TATAAAA GACACCG | GGGAA | 0.5 | chr7:+99103371 | 1 | 99103371 | 4 | FALSE |
| CCATTGAT CTAAAAG TCACCA | CTGGA | 0.5 | chr3:-65736276 | -1 | 65736276 | 5 | FALSE |
| AAATACC TGTAAGA GACACCA | CTGAG | 0.5 | chr3:-65976946 | -1 | 65976946 | 5 | FALSE |
| TGGTAGA TTATAAG ACACCG | TAGGG | 0.5 | chr10:-3117938 | -1 | 3117938 | 5 | FALSE |
| GAATGGA TGTGAAA GGCACCA | CTCCGA | 0.5 | chr5:-79875682 | -1 | 79875682 | 4 | FALSE |
| AAATAAA TGTGAAA GTCACCA | CAGAA | 0.5 | chr8:-131973280 | -1 | 1.32E+08 | 5 | FALSE |
| AGATGGA RGGCARA GACACCA | CGGGG | 0.4 | chr3:+52369345 | 1 | 52369345 | 5 | FALSE |
| THGAAAG ATCTTAA AGCCACCA | AAGGA | 0.4 | chr20:-24138791 | -1 | 24138791 | 4 | FALSE |
| GAGTAGA TCTAAAA GACAGCA | AGGAA | 0.4 | chr12:-62718609 | -1 | 62718609 | 5 | FALSE |
| TCATATGT GTAAAAG ACACAA | AGGAG | 0.4 | chr2:+3551648 | 1 | 3551648 | 4 | FALSE |
| GGTTAGC GGGAAAA GACACCA | CAGGHG | 0.4 | chrX:-141696540 | -1 | 1.42e+08 | 4 | FALSE |
| GGTTAGC GGGAAAA GACACCA | CAGGG | 0.4 | chrX:+141591639 | 1 | 1.42E+08 | 4 | FALSE |
| GGTTAGC XGGGAAA AGACACCA | CAGGG | 0.4 | chrX:-141582808 | -1 | 1.42E+08 | 4 | FALSE |
| GGTTAGC GGGAAAA GACACCA | CAGGG | 0.4 | chrX:-141240587 | -1 | 1.42E+08 | 4 | FALSE |
| GGTTAGC GGGAAAA GACACCA | CAGGG | 0.4 | chrX:+141004580 | 1 | 1.42E+08 | 4 | FALSE |
| GCATTCA TGCAAAA GACACTA | TAGGG | 0.4 | chr3:-85730118 | -1 | 85730118 | 5 | FALSE |
| AGAAATA TCTAAAA GACAACA | AAGAC | 0.4 | chr7:+122888645 | 1 | 1.23E+08 | 4 | FALSE |

TABLE 3-continued

| HIV-1 Gag D target (+strand) |
| --- |
| GGATAGATGTAAAAGACACCAAGGAAG |

| Sequence | PAM | Score | Gene | Chromosome | Strand | Position | Mismatch | On-target |
| --- | --- | --- | --- | --- | --- | --- | --- | --- |
| GGAAAGG AGCAAAA GACACCA | GAGGG | 0.4 | | chr17:-81470363 | -1 | 81470363 | 5 | FALSE |
| AGATTCA TTTAAAA GACAACA | AAGAA | 0.4 | | chr8:-109514887 | -1 | 1.1E+08 | 5 | FALSE |
| AGAGATA TGTATAA GACACAA | TAGGA | 0.3 | | chr2:+212064031 | 1 | 2.12E+08 | 5 | FALSE |
| AGATAGA AATGAAA GACACTA | GTGAA | 0.3 | | chr2:-141095548 | -1 | 1.41E+08 | 5 | FALSE |
| TGATAAA TGGGAAT GACACCA | GAGAG | 0.3 | | chr4:+146453372 | 1 | 1.46E+08 | 5 | FALSE |

TABLE 4

HIV-1 LTR1 target single cell clone off target analysis.
(Table discloses SEQ ID NOS 147-150, respectively, in order of appearance)

| OFF TARGET | Target sequence: LTR1  PAM GCAGAACTACACACCAGGGCCAGGGAT Predicted off target sequence: | Chromosome location/gene | Strand | Position | Score | Mis-matches | Single cell clone | Number of sequences analyzed | Indels detected |
| --- | --- | --- | --- | --- | --- | --- | --- | --- | --- |
| 1 | ACAGCACTCCCCACCAGGGCTTGGGGG | Ch 16/TSC2 | – | 2082981 | 0.7 | 5 | TOTAL | 26 | 0 |
| | | | | | | | CTRL1 | 5 | 0 |
| | | | | | | | CTRL2 | 3 | 0 |
| | | | | | | | ERAD1 | 3 | 0 |
| | | | | | | | ERAD2 | 3 | 0 |
| | | | | | | | ERAD3 | 3 | 0 |
| | | | | | | | ERAD4 | 3 | 0 |
| | | | | | | | ERAD5 | 3 | 0 |
| | | | | | | | ERAD6 | 3 | 0 |
| 2 | ACAAACCTACAGACCAGAGCCCAGGGT | Ch 11/TUB | —— | 8105357 | 0.4 | 5 | TOTAL | 27 | 0 |
| | | | | | | | CTRL1 | 3 | 0 |
| | | | | | | | CTRL2 | 3 | 0 |
| | | | | | | | ERAD1 | 3 | 0 |
| | | | | | | | ERAD2 | 3 | 0 |
| | | | | | | | ERAD3 | | 0 |
| | | | | | | | ERAD4 | 5 | 0 |
| | | | | | | | ERAD5 | 3 | 0 |
| | | | | | | | ERAD6 | 3 | 0 |
| 3 | CCAGACCGAGACACCAGGGGGCGGGGGA | Ch 12/SLC41A2 | + | 104958165 | 0.2 | 5 | TOTAL | 6 | 0 |
| | | | | | | | CTRL1 | | |
| | | | | | | | CTRL2 | | |
| | | | | | | | ERAD1 | | |
| | | | | | | | ERAD2 | 1 | 0 |
| | | | | | | | ERAD3 | 2 | 0 |
| | | | | | | | ERAD4 | | |
| | | | | | | | ERAD5 | 2 | 0 |
| | | | | | | | ERAD6 | 1 | 0 |

TABLE 5

HIV-1 GagD target single cell clone off target analysis
(Table discloses SEQ ID NOS 151-154, respectively, in order of appearance)

| OFF TARGET | Target sequence: gagD GGATAGATGTAAAAGACACCAAGGAAG Predicted off target sequence: PAM | Chromosome location/gene | Strand | Position | Score | Mis-matches | Single cell clone | Number of sequences analyzed | Indels detected |
|---|---|---|---|---|---|---|---|---|---|
| 1 | CCAAAGATGAAAAAGACACCCGAGAAA | Ch 10/TACC2 | + | 122211347 | 0.6 | 5 | TOTAL | 34 | 0 |
| | | | | | | | CTRL1 | 3 | 0 |
| | | | | | | | CTRL2 | 3 | 0 |
| | | | | | | | ERAD1 | 6 | 0 |
| | | | | | | | ERAD2 | 6 | 0 |
| | | | | | | | ERAD3 | 3 | 0 |
| | | | | | | | ERAD4 | 4 | 0 |
| | | | | | | | ERAD5 | 4 | 0 |
| | | | | | | | ERAD6 | 5 | 0 |
| 2 | TGAGACTTGTACAAGACACCACGGGGC | Ch 20/ADNP | − | 50889247 | 0.5 | 5 | TOTAL | 23 | 0 |
| | | | | | | | CTRL1 | 2 | 0 |
| | | | | | | | CTRL2 | 3 | 0 |
| | | | | | | | ERAD1 | 3 | 0 |
| | | | | | | | ERAD2 | 3 | 0 |
| | | | | | | | ERAD3 | 3 | 0 |
| | | | | | | | ERAD4 | 3 | 0 |
| | | | | | | | ERAD5 | 3 | 0 |
| | | | | | | | ERAD6 | 3 | 0 |
| 3 | AGAAAAATGTAAAAGACACCTTGGAAA | Ch 3/non gene | − | 144746442 | 1.7 | 4 | TOTAL | 24 | 0 |
| | | | | | | | CTRL1 | 3 | 0 |
| | | | | | | | CTRL2 | 3 | 0 |
| | | | | | | | ERAD1 | 3 | 0 |
| | | | | | | | ERAD2 | 3 | 0 |
| | | | | | | | ERAD3 | 3 | 0 |
| | | | | | | | ERAD4 | 3 | 0 |
| | | | | | | | ERAD5 | 3 | 0 |
| | | | | | | | ERAD6 | 3 | 0 |

TABLE 6

Number of somatic SNPs in different genomic regions

| Sample | #4349 | #4346 | #4356 |
|---|---|---|---|
| CDS | 6590 | 6760 | 5895 |
| Synonymous_SNP | 3003 | 3053 | 2588 |
| Missense_SNP | 3372 | 3465 | 3050 |
| Stopgain | 70 | 86 | 128 |
| Stoploss | 6 | 6 | 7 |
| Unknown | 140 | 151 | 122 |
| Intronic | 414960 | 415812 | 382465 |
| UTR3 | 8195 | 8197 | 7713 |
| UTR5 | 1905 | 1947 | 1649 |
| Splicing | 23 | 27 | 30 |
| ncRNA_exonic | 3982 | 4073 | 3509 |
| ncRNA_intronic | 65272 | 65664 | 59525 |
| ncRNA_splicing | 14 | 14 | 13 |
| Upstream | 6962 | 7052 | 6063 |
| Downstream | 7822 | 7850 | 7005 |
| Intergenic | 664364 | 669294 | 602974 |
| Total | 1180363 | 1186971 | 1077074 |

Sample: sample name

CDS: the number of somatic SNPs in coding region

Synonymous_SNP: a single nucleotide change that does not cause an amino acid change Missense_SNP: a single nucleotide change that causes an amino acid change Stopgain: a nonsynonymous SNP that leads to the immediate creation of stop codon at the variant site Stoploss: a nonsynonymous SNP that leads to the immediate elimination of stop codon at the variant site Unknown: unknown function (due to various errors in the gene structure definition in the database file)

Intronic: the number of somatic SNPs in intronic region

UTR3: the number of somatic SNPs in 3'UTR region

UTR5: the number of somatic SNPs in 5'UTR region

Splicing: the number of somatic SNPs within 2-bp of a splicing junction ncRNA_exonic: the number of somatic SNPs in exonic region of non-coding RNAs ncRNA_intronic: the number of somatic SNPs in intronic region of non-coding RNAs TABLE 6-continued Number of somatic SNPs in different genomic regions

| Sample | #4349 | #4346 | #4356 |
|---|---|---|---| ncRNA_splicing: the number of somatic SNPs within 2-bp of a splicing junction of non-coding RNAs Upstream: the number of somatic SNPs within 1 kb away from the transcription start site Downstream: the number of somatic SNPs within the 1 kb away from the transcription termination site Intergenic: the number of somatic SNPs in intergenic region Total: the total number of somatic SNPs

TABLE 7

Number of somatic InDels in different genomic regions

| Sample | #4349 | #4346 | #4356 |
|---|---|---|---|
| CDS | 103 | 124 | 59 |
| Frameshift_deletion | 31 | 34 | 21 |
| Frameshift_insertion | 14 | 16 | 10 |
| Nonframeshift_deletion | 36 | 48 | 16 |
| Nonframeshift_insertion | 18 | 22 | 9 |
| Stopgain | 2 | 2 | 1 |
| Stoploss | 0 | 0 | 0 |
| Unknown | 2 | 2 | 2 |
| Intronic | 36969 | 39727 | 25080 |
| UTR3 | 946 | 1003 | 640 |
| UTR5 | 134 | 149 | 89 |
| Splicing | 5 | 5 | 3 |
| ncRNA_exonic | 285 | 314 | 190 |
| ncRNA_intronic | 5794 | 6247 | 3971 |

TABLE 7-continued

| Number of somatic InDels in different genomic regions | | | |
|---|---|---|---|
| Sample | #4349 | #4346 | #4356 |
| ncRNA_splicing | 2 | 3 | 1 |
| Upstream | 694 | 771 | 417 |
| Downstream | 879 | 958 | 602 |
| Intergenic | 56749 | 61117 | 38406 |
| Total | 102588 | 110452 | 69477 |

Sample: sample name

CDS: the number of somatic InDels in coding region

Frameshift deletion: a deletion of one or more nucleotides that cause frameshift changes in protein coding sequence Frameshift insertion: an insertion of one or more nucleotides that cause frameshift changes in protein coding sequence Nonframeshift deletion: a deletion that does not cause frameshift changes Nonframeshift insertion: an insertion that does not cause frameshift changes Stopgain: an insertion or a deletion that leads to the immediate creation of stop codon at the variant site Stoploss: an insertion or a deletion that leads to the immediate elimination of stop codon at the variant site Unknown: unknown function (due to various errors in the gene structure definition in the database file)

Intronic: the number of somatic InDels in intronic region

UTR3: the number of somatic InDels in 3'UTR region

UTR5: the number of somatic InDels in 5'UIR region

Splicing: the number of somatic InDels within 2-bp of a splicing junction ncRNA_exonic: the number of somatic InDels inexonic region of non-coding RNAs ncRNA_intronic: the number of somatic InDels in intronic region of non-coding RNAs ncRNA_splicing: the number of somatic InDels within 2-bp of a splicing junction of non-coding RNAs Upstream: the number of somatic InDels within 1 kb away from transcription start site Downstream: the number of somatic InDels within 1 kb away from transcription termination site Intergenic: the number of somatic InDels in intergenic region Total: the total number of somatic InDels

REFERENCES

1. G. Hutter et al., Long-term control of HIV by CCR5 Delta32/Delta32 stem-cell transplantation. *The New England journal of medicine* 360, 692-698 (2009).

2. W. Xu et al., Advancements in Developing Strategies for Sterilizing and Functional HIV Cures. *BioMed research international* 2017, U.S. Pat. No. 6,096,134 (2017).

3. A. Saez-Cirion et al., Post-treatment HIV-1 controllers with a long-term virological remission after the interruption of early initiated antiretroviral therapy ANRS VISCONTI Study. *PLoS pathogens* 9, e1003211 (2013).

4. J. Z. Li et al., The size of the expressed HIV reservoir predicts timing of viral rebound after treatment interruption. *AIDS (London, England)* 30, 343-353 (2016).

5. J. D. Siliciano, R. F. Siliciano, Recent developments in the effort to cure HIV infection: going beyond N=1. *The Journal of clinical investigation* 126, 409-414 (2016).

6. A. R. Martin, R. F. Siliciano, Progress Toward HIV Eradication: Case Reports, Current Efforts, and the Challenges Associated with Cure. *Annual review of medicine* 67, 215-228 (2016).

7. D. Singh et al., Development and characterization of a long-acting nanoformulated abacavir prodrug. *Nanomedicine (London, England)* 11, 1913-1927 (2016).

8. D. Guo et al., Creation of a Long-Acting Nanoformulated 2',3'-Dideoxy-3'-Thiacytidine. *Journal of acquired immune deficiency syndromes (1999)* 74, e75-e83 (2017).

9. B. Edagwa, et al, Long-acting slow effective release antiretroviral therapy. *Expert opinion on drug delivery,* 1-11 (2017).

10. P. K. Dash et al., Long-acting nanoformulated antiretroviral therapy elicits potent antiretroviral and neuroprotective responses in HIV-1-infected humanized mice. *AIDS (London, England)* 26, 2135-2144 (2012).

11. Hu et.al, RNA-directed gene editing specifically eradicates latent and prevents new HIV-1 infection. Proc. Natl. Acad. Sci. USA 111, 11461-11466 (2014)

12. R. Kaminski et al., Elimination of HIV-1 Genomes from Human T-lymphoid Cells by CRISPR/Cas9 Gene Editing. *Scientific reports* 6, 22555 (2016).

13. R. Kaminski et al., Negative Feedback Regulation of HIV-1 by Gene Editing Strategy. *Scientfc reports* 6, 31527 (2016).

14. M. K. White, W. Hu, K. Khalili, Gene Editing Approaches against Viral Infections and Strategy to Prevent Occurrence of Viral Escape. *PLoS pathogens* 12, e1005953 (2016).

15. R. Kaminski et al., Excision of HIV-1 DNA by gene editing: a proof-of-concept in vivo study. *Gene therapy* 23, 690-695 (2016).

16. C. Yin et al., In Vivo Excision of HIV-1 Provirus by saCas9 and Multiplex Single-Guide RNAs in Animal Models. *Molecular therapy: the journal of the American Society of Gene Therapy* 25, 1168-1186 (2017).

17. M. Arainga, et al, HIV-1 cellular and tissue replication patterns in infected humanized mice. *Scientific reports* 6, 23513 (2016).

18. M. Arainga et al., A mature macrophage is a principal HIV-1 cellular reservoir in humanized mice after treatment with long acting antiretroviral therapy. *Retrovirology* 14, 17 (2017).

19. R. C. Gallo, Shock and kill with caution. *Science (New York, N.Y.)* 354, 177-178 (2016).

20. S. N. Byrareddy et al., Sustained virologic control in SIV+macaques after antiretroviral and alpha4beta7 antibody therapy. *Science (New York, N.Y.)* 354, 197-202 (2016).

21. S. Gorantla et al., Human immunodeficiency virus type 1 pathobiology studied in humanized BALB/c-Rag2−/−gammac−/−mice. *Journal of virology* 81, 2700-2712 (2007).

22. S. Gorantla et al., Links between progressive HIV-1 infection of humanized mice and viral neuropathogenesis. *Am J Pathol* 177, 2938-2949 (2010).

23. J. M. Jacobson et al., Evidence that intermittent structured interruption, but not immunization with ALVAC-HIV vCP 1452, promotes control of HIV replication: the results of AIDS Clinical Trials Group. J. Infect Dis. 194, 623-632 (2006).

24. J. B. Honeycutt et al., HIH persistence in tissue macrophages of humanized myeloid-only mice during antiretroviral therapy. *Nat. Med.* 23, 638-643 (2017).

25. R. H. Kutner et al., Production, concentration and titration of pseudotyped HIV-1-based lentiviral vectors. Nature Protocols 4, 495-505 (2009).

26 O'Doherty U et al., Human Immunodeficiency Virus Type 1 spinoculation enhances infection through virus binding. Journal of Virology 74(21), 10074-10080 (2000).

27. P. K. Dash et al., Loss of neuronal integrity during progressive HIV-1 infection of humanized mice. *J Neurosci* 31, 3148-3157 (2011).

28. Westervelt, et al, Identification of a determinant within the human immunodeficiency virus 1 surface envelope glycoprotein critical for productive infection of primary monocytes. *Proceedings of the National Academy of Sciences of the United States of America* 88, 3097-3101 (1991).

29. G. Zhang et al., The mixed lineage kinase-3 inhibitor URMC-099 improves therapeutic outcomes for long-acting antiretroviral therapy. *Nanomedicine: nanotechnology, biology, and medicine* 12, 109-122 (2016).

30. A. S. Nowacek et al., NanoART synthesis, characterization, uptake, release and toxicology for human monocyte-macrophage drug delivery. *Nanomedicine* (*London, England*) 4, 903-917 (2009).

31. L. M. Agosto et al., HIV-1 integrates into resting CD4+ T cells even at low inoculums as demonstrated with an improved assay for HIV-1 integration. *Virology* 368, 60-72 (2007).

32. A. O. Pasternak et al., Highly sensitive methods based on seminested real-time reverse transcription-PCR for quantitation of human immunodeficiency virus type 1 unspliced and multiply spliced RNA and proviral DNA. *Journal of clinical microbiology* 46, 2206-2211 (2008).

33. M. K. Liszewski, et al, Detecting HIV-1 integration by repetitive-sampling Alu-gag PCR. *Methods (San Diego, Calif)* 47, 254-260 (2009).

34. C. Deleage et al., Defining HIV and SIV Reservoirs in Lymphoid Tissues. *Pathogens* &

35. M. J. Buzon et al., Long-term antiretroviral treatment initiated at primary HIV-1 infection affects the size, composition, and decay kinetics of the reservoir of HIV-1-infected CD4 T cells. *Journal of virology* 88, 10056-10065 (2014).

36. M. J. Buzon et al., HIV-1 persistence in CD4+ T cells with stem cell-like properties. *Nature medicine* 20, 139-142 (2014).

37. G. M. Laird et al., Rapid quantification of the latent reservoir for HIV-1 using a viral outgrowth assay. *PLoS pathogens* 9, e1003398 (2013).

The invention has been described in an illustrative manner, and it is to be understood that the terminology that has been used is intended to be in the nature of words of description rather than of limitation. Obviously, many modifications and variations of the present invention are possible in light of the above teachings. It is, therefore, to be understood that within the scope of the appended claims, the invention can be practiced otherwise than as specifically described.

---

What is claimed:

1. A method of eradicating or eliminating a retrovirus in a subject, comprising administering to a patient a composition comprising a therapeutically effective amount of at least one antiretroviral agent, wherein the antiretroviral agent is formulated as a long-acting slow effective release (LASER) antiretroviral agent and a composition comprising a therapeutically effective amount of at least one gene editing agent, comprising an isolated nucleic acid sequence encoding:

(a) a Clustered Regularly Interspaced Short Palindromic Repeat (CRISPR)-associated endonuclease/Cas9 (CRISPR/Cas9), and b) two or more guide RNAs, (i) a first guide RNA of the two or more guide RNAs being complementary to a first target nucleic acid sequence within a 5'- or 3'-long terminal repeat (LTR) of a human immunodeficiency virus sequence, and (ii) a second guide RNA of the two or more guide RNAs being complementary to a second target nucleic acid sequence within a group specific antigen (Gag) region of a human immunodeficiency virus sequence, wherein the first gRNA comprises SEQ ID NO: 303 and the second gRNA comprises SEQ ID NO: 304, thereby eradicating or eliminating the retrovirus in a subject.

2. The method of claim 1, wherein the at least one antiretroviral agent is nanoformulated.

3. The method of claim 2, wherein the at least one antiretroviral agent comprises: myristolyated dolutegravir, lamivudine, abacavir, rilpivirine or combinations thereof.

4. The method of claim 1, wherein the at least one antiretroviral agent is administered to the subject prior to administering the at least one gene editing agent.

5. The method of claim 1, wherein the at least one antiretroviral agent and at least one gene-editing agent are co-administered.

6. The method of claim 1, wherein the at least one antiretroviral agent and at least one gene-editing agent are administered sequentially.

7. The method of claim 1, wherein the CRISPR/Cas fusion protein comprises catalytically deficient Cas protein (dCas), orthologs, homologs, mutants variants or fragments thereof.

8. The method of claim 1, wherein the intervening sequences between the two gRNAs are removed.

9. The method of claim 1, wherein the isolated nucleic acid is included in at least one expression vector.

10. The method of claim of claim 9, wherein the expression vector comprises a lentiviral vector, an adenoviral vector, or an adeno-associated virus vector.

11. The method of claim 1, optionally comprising a therapeutically effective amount of a non-nucleoside reverse transcriptase inhibitor (NNRTI), and/or a nucleoside reverse transcriptase inhibitor (NRTI) and/or a protease inhibitor.

12. The method of claim 11, wherein the NNRTI comprises: etravirine, efavirenz, nevirapine, rilpivirine, delavirdine, or nevirapine.

13. The method of claim 11, wherein the NRTI comprises: lamivudine, zidovudine, emtricitabine, abacavir, zalcitabine, dideoxycytidine, azidothymidine, tenofovir disoproxil fumarate, didanosine (ddI EC), dideoxyinosine, stavudine, abacavir sulfate or combinations thereof.

14. The method of claim 11, wherein a protease inhibitor comprises: amprenavir, tipranavir, indinavir, saquinavir mesylate, lopinavir and ritonavir (LPV/RTV), Fosamprenavir Calcium (FOS-APV), ritonavir, darunavir, atazanavir sulfate, nelfinavir mesylate or combinations thereof.

*    *    *    *    *